(12) United States Patent
Ohta et al.

(10) Patent No.: US 9,258,464 B2
(45) Date of Patent: Feb. 9, 2016

(54) RADIATION VIDEO PROCESSING DEVICE, RADIATION VIDEO CAPTURING DEVICE, RADIATION VIDEO CAPTURING SYSTEM, RADIATION VIDEO PROCESSING METHOD AND PROGRAM STORAGE MEDIUM

(71) Applicant: FUJIFILM Corporation, Tokyo (JP)

(72) Inventors: Yasunori Ohta, Kanagawa (JP); Naoyuki Nishino, Kanagawa (JP); Haruyasu Nakatsugawa, Kanagawa (JP); Naoto Iwakiri, Kanagawa (JP); Kouich Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 99 days.

(21) Appl. No.: 14/259,619

(22) Filed: Apr. 23, 2014

(65) Prior Publication Data

US 2014/0232841 A1 Aug. 21, 2014

Related U.S. Application Data

(63) Continuation of application No. PCT/JP2012/077612, filed on Oct. 25, 2012.

(30) Foreign Application Priority Data

Oct. 26, 2011 (JP) .................................. 2011-235321
Oct. 26, 2011 (JP) .................................. 2011-235323

(51) Int. Cl.
*H04N 5/225* (2006.01)
*H05G 1/60* (2006.01)
(Continued)

(52) U.S. Cl.
CPC ................ *H04N 5/225* (2013.01); *A61B 6/461* (2013.01); *A61B 6/487* (2013.01); *A61B 6/54* (2013.01);
(Continued)

(58) Field of Classification Search
CPC ............. H05G 1/60; H05G 1/56; H05G 1/64; H04N 5/225; H04N 5/3205; H04N 5/321; H04N 2005/2255; A61B 6/287; A61B 6/4283; A61B 6/54; A61B 6/461; A61B 6/4233; G01T 1/2018

See application file for complete search history.

(56) References Cited

U.S. PATENT DOCUMENTS 6,424,750 B1 * 7/2002 Colbeth ................... H04N 5/32
348/E5.081
8,254,523 B2 * 8/2012 Takekoshi ................ A61B 6/06
378/98.2

(Continued)

FOREIGN PATENT DOCUMENTS

EP 1 999 718 12/2008
JP 07-75632 A 3/1995

(Continued)

OTHER PUBLICATIONS

English Translation of Yoshihiro JP 2007101529 A.*

(Continued)

*Primary Examiner* — Nhon Diep
*Assistant Examiner* — Jill Sechser
(74) *Attorney, Agent, or Firm* — Birch, Stewart, Kolasch & Birch, LLP

(57) ABSTRACT

A radiographic video processing device includes: an acquisition section that acquires gradation signals expressing charges; and a control section that, if capture of a video image formed from plural frames is being performed with a radiation detector, and a number of the pixels, from which charges are combined and read by switching elements included in adjacent pixels of the radiation detector, has been increased, effects control such that, from a frame at a time of the increase up until a predetermined frame, the gradation signals distributed in a higher density range than that for frames subsequent to the predetermined frame are used as image data.

17 Claims, 29 Drawing Sheets

(51) Int. Cl.
*H05G 1/64* (2006.01)
*H05G 1/56* (2006.01)
*H04N 5/32* (2006.01)
*H04N 5/321* (2006.01)
*G01T 1/20* (2006.01)
*G03B 42/04* (2006.01)
*A61B 6/00* (2006.01)

(52) U.S. Cl.
CPC ............. *G01T 1/2018* (2013.01); *H04N 5/32* (2013.01); *H04N 5/321* (2013.01); *H04N 5/3205* (2013.01); *H05G 1/56* (2013.01); *H05G 1/60* (2013.01); *H05G 1/64* (2013.01); *A61B 6/4233* (2013.01); *A61B 6/4283* (2013.01); *A61B 6/566* (2013.01); *G03B 42/04* (2013.01); *H04N 2005/2255* (2013.01)

(56) References Cited

U.S. PATENT DOCUMENTS

| | | |
|---|---|---|
| 2005/0220270 A1 | 10/2005 | Kameshima et al. |
| 2007/0096032 A1 | 5/2007 | Yagi et al. |
| 2008/0054182 A1 | 3/2008 | Yokoyama et al. |
| 2009/0021607 A1 | 1/2009 | Takenaka et al. |
| 2009/0026379 A1 | 1/2009 | Yaegashi et al. |
| 2009/0224235 A1 | 9/2009 | Kitamura et al. |

FOREIGN PATENT DOCUMENTS

| | | |
|---|---|---|
| JP | 2005-287773 A | 10/2005 |
| JP | 2006-158728 A | 6/2006 |
| JP | 2007-068014 A | 3/2007 |
| JP | 2008-022520 A | 1/2008 |
| JP | 2008-083031 A | 4/2008 |
| JP | 2009-032854 A | 2/2009 |
| JP | 2009-212389 A | 9/2009 |
| JP | 2012-244607 | 12/2012 |
| WO | WO 2007/119495 A2 | 10/2007 |
| WO | WO 2012/056899 A1 | 5/2012 |

OTHER PUBLICATIONS

English Translation of Hiroyuki et al. JP 2007215760 A.*
International Search Report issued in PCT/JP2012/077612, mailed on Jan. 8, 2013.
Written Opinion issued in PCT/JP2012/077612, mailed on Jan. 8, 2013.

* cited by examiner

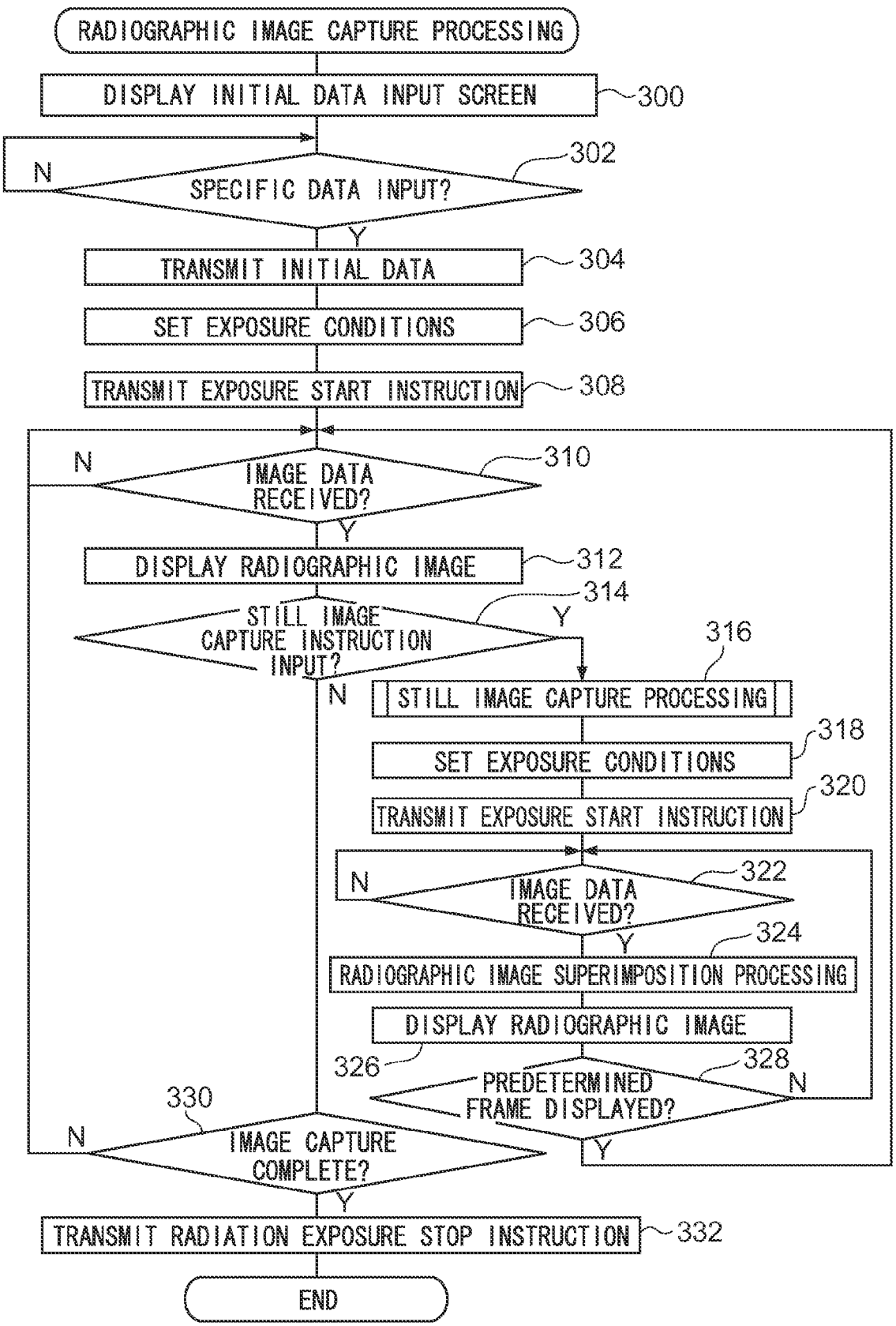

INITIAL DATA INPUT SCREEN

PLEASE INPUT NAME OF SUBJECT, IMAGING TARGET SITE, POSTURE DURING IMAGING, RADIATION EXPOSURE CONDITIONS FOR STILL IMAGE CAPTURE, AND NUMBER OF PROCESSING TARGET FRAMES.

NAME OF SUBJECT Mr/Ms

IMAGING TARGET SITE

IMAGING POSTURE

EXPOSURE CONDITIONS (FOR STILL IMAGE CAPTURE)
- TUBE VOLTAGE
- TUBE CURRENT
- EXPOSURE DURATION

NUMBER OF PROCESSING TARGET FRAMES

COMPLETE

FIG.22
(1) FIRST FRAME
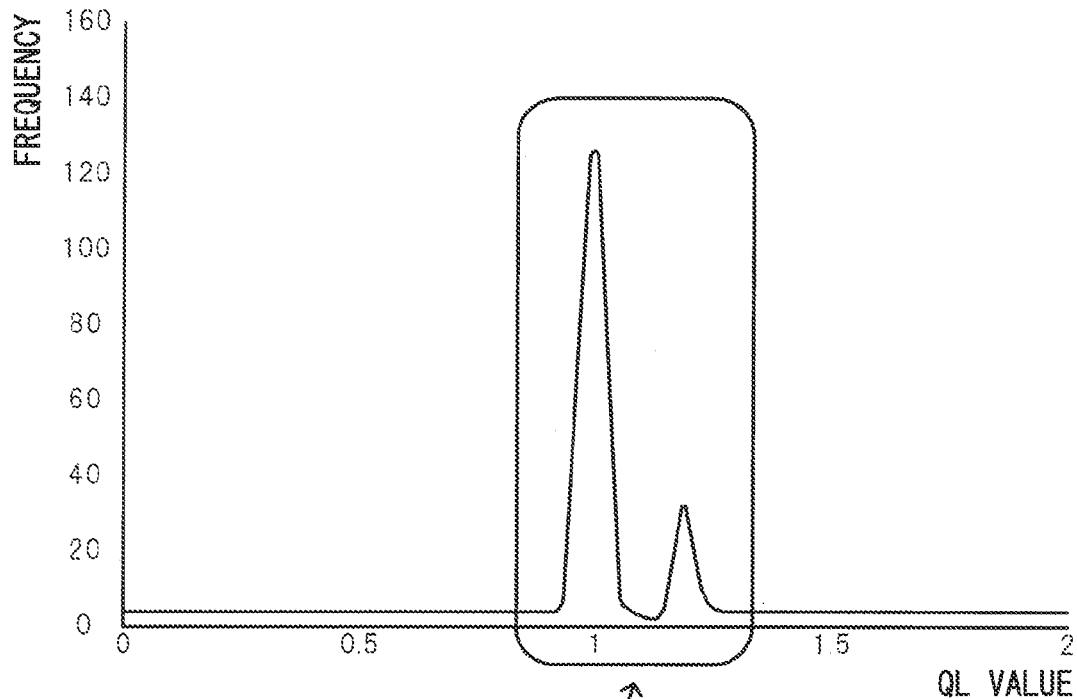
(2) AFTER SEVERAL FRAMES
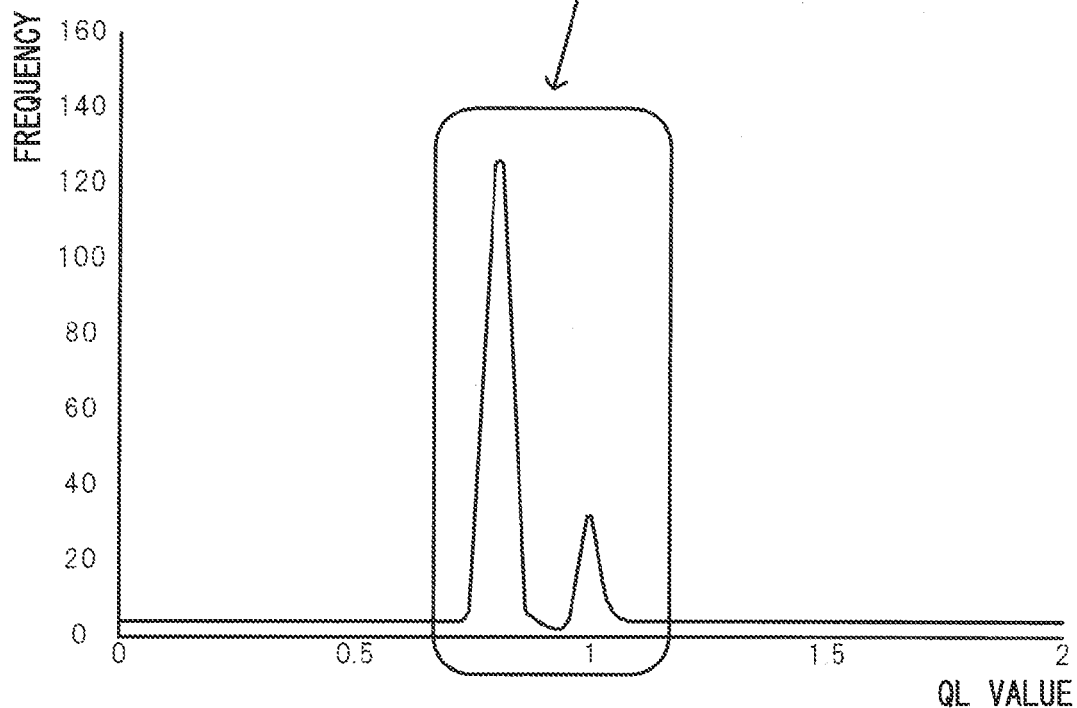

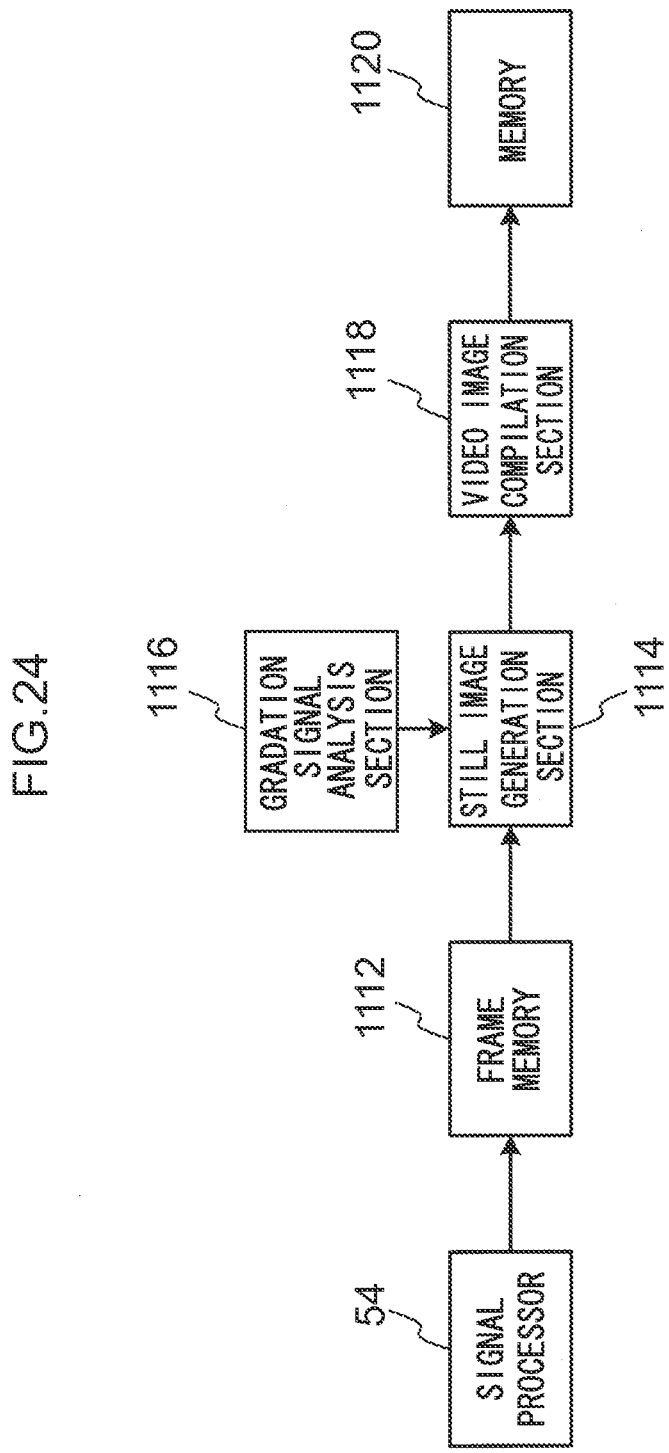

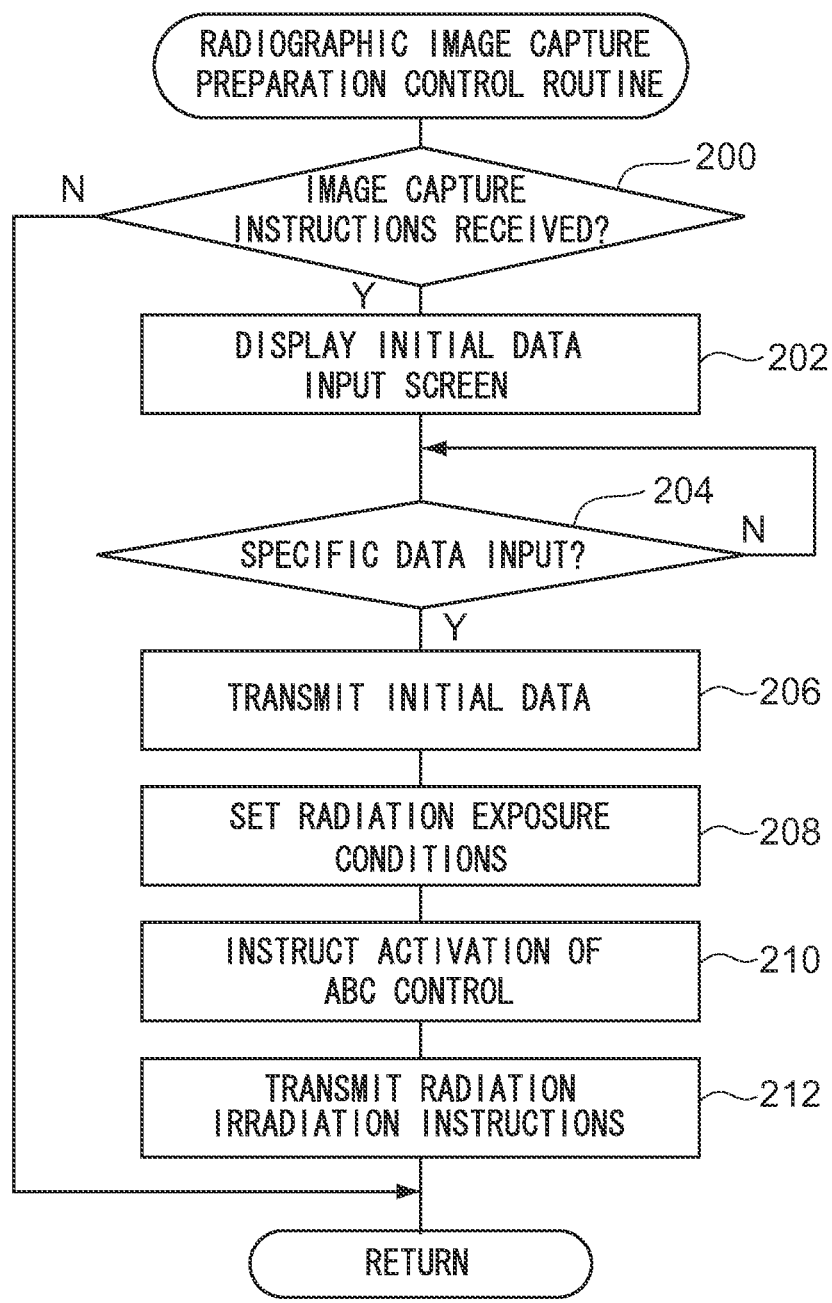

RADIATION VIDEO PROCESSING DEVICE, RADIATION VIDEO CAPTURING DEVICE, RADIATION VIDEO CAPTURING SYSTEM, RADIATION VIDEO PROCESSING METHOD AND PROGRAM STORAGE MEDIUM

CROSS-REFERENCE TO RELATED APPLICATIONS

This application is a continuation application of International Application No. PCT/JP/2012/077612, filed on Oct. 25, 2012, which is incorporated herein by reference. Further, this application claims the benefit of priority of prior Japanese Patent Application No. 2011-235321, filed on Oct. 26, 2011, and Japanese Patent Application No. 2011-235323, filed on the same date, the entire contents of which are incorporated herein by reference.

BACKGROUND OF THE INVENTION

1. Field of the Invention

The present invention relates to a radiographic video processing device, a radiographic video capturing device, a radiographic video capturing system, a radiographic video processing method, and a program storage medium.

2. Related Art

Recently, radiation detectors sometimes referred to as, for example, "electronic cassettes") such as flat panel detectors (FPDs) are being implemented, in which a radiation sensitive layer is disposed on a thin film transistor (TFT) active matrix substrate and with which radiation can be converted directly into digital data. Radiographic image capture devices that employ such radiation detectors and capture radiographic images expressing irradiated radiation are also being implemented. Radiation conversion methods used by radiation detectors employed in such radiographic image capture devices include indirect conversion methods, in which radiation is first converted into light with a scintillator and then the converted light is converted into electrical charges (charges) with a semiconductor layer, such as a photodiode, and direct conversion methods in which radiation is converted into charges with a semiconductor layer such as amorphous selenium. There are various materials that can be used in the semiconductor layer for each method.

Such radiographic image capture devices include devices capable of performing video image capture in addition to capturing still radiographic images. Utilizing such a radiographic image capture device enables displaying the state inside the body of a patient as a video image (fluoroscopic image) on a display device in real-time, thereby enabling an endoscope to be passed to an affected site while observing the video image, and performing treatment of the affected site while observing the affected site through the endoscope. Further, using such radiographic image capturing devices enable, for example, Interventional Radiology (IVR) in which the distal end of a catheter to which various instruments are attached is passed to an affected site and medical treatment is performed by manipulation of the catheter from outside of the body.

As an example of technology relating to such types of radiographic image capture devices capable of performing both still image capture and video image capture, Japanese Patent Application Laid-Open (JP-A) No. 2008-83031 discloses an electronic cassette type radiation detector provided with a sensor array including plural sensors that detect incident radiation. The electronic cassette type radiation detector includes a connection portion for a detachable additional function module, and includes a selection means for switching image capture modes in a selectable state between a still image capture and a video image capture by connecting the additional function module.

Moreover, JP-A No. 2005-287773 discloses an image capture device including: an area sensor; an image capture mode setting means that selects one image capture mode from plural predetermined image capture modes; a correction means that performs computation using image capture output from the area sensor and an offset output; and a control means that controls operation of the area sensor and the computation by the correction means according to signals from the image capture mode setting means.

Technology such as that disclosed in JP-A No. 2006-158728 is proposed as technology relating to video image capture.

JP-A No. 2006-158728 proposes technology in which an imaging subject is irradiated with radiation from a radiation irradiation section at a specific cycle, a subject image is detected by a photoelectric conversion circuit based on the irradiated radiation and offset images are also periodically acquired, and a radiation irradiation cycle of the radiation irradiation section and a read cycle of the subject image from the photoelectric conversion circuit are controlled according to changes in the periodically acquired offset images. Thereby, accurate offset correction of the imaging subject image is performed directly after the start of image capture when fluctuations in offset occur due to alternately performing the offset image capture and the imaging subject image capture, and capturing of the subject image is successively performed at a high frame rate after the offset has stabilized.

Moreover, since there is a need to shorten the reading time for videos, when charges according to radiation dose are read, the reading time can be shortened by technology in which plural lines are read at the same time using a binning read method that reads charges of plural lines at the same time, such as in the technology disclosed in JP-A No. 2007-68014. JP-A No. 2007-68014 proposes that voltage supplied from a vertical drive circuit to a transfer section is varied according to the number of pixels that are read at the same time, in order to prevent an increase in an electrical offset component and a decrease in output voltage from pixel output amplifiers.

In a radiographic image capture device of this type, plural pixels, each including a sensor portion that generates charges according to irradiated radiation, and a switching element that reads charges generated in the sensor portion, are disposed in a matrix formation. In such a radiographic image capture device, 'binning' may be performed, in which charges generated by plural adjacent pixels in the radiation detector are combined and read, in order, for example, to reading out image data obtained by image capture at high speed, or to enhance image capture sensitivity.

However, in cases in which an image captured by a radiographic image capture device capable of performing video image capture such as that described above is displayed on a display device, in situations in which the number of pixels whose charges are combined by binning (hereafter also referred to as the binning number) is increased while performing image capture in the radiographic image capture device, there is an issue that disruption may occur for several frames' worth of displayed images from the point in time of the increase.

Feed-through noise with mutually reverse polarity occurs at timings when the switching elements provided to the radiation detector of the radiographic image capture device are switched ON and when the switching elements are switched OFF.

The charges read by each of the switching elements of the radiation detector are converted to voltage while being integrated by an amplifier at a predetermined cycle, and are then converted to digital values by an analog-to-digital (A/D) converter. Consequently, the influence of feed-through noise is normally prevented since the two feed-through noises of reverse polarity to each other are integrated by the amplifier, and as a result each feed-through noise is cancelled out.

However, before and after an increase in the binning number in the radiation detector, the wiring capacity of signal wirings for outputting charges read by the switching elements suddenly changes, resulting in a sudden change in the manner in which feed-through noise occurs. It is thought that the disruption in the display image occurs as a result that cancelling out of the feed-through noises is not able to follow such change.

In the technology described in JP-A No. 2006-158728, no consideration is given to unstable video image quality when switching to increase the number of lines that are read at the same time in a binning reading method, leaving room for improvement.

In the technology described in JP-A No. 2007-68014, reduction in dynamic range and deterioration in sensitivity characteristics are prevented by varying the voltage supplied to the transfer portion from the vertical drive circuit according to the number of pixels that are read at the same time. However, as above, no consideration is given to unstable video image quality when switching to increase the binning number, leaving room for improvement.

SUMMARY

In order to address the above, the present invention provides a radiographic video processing device, a radiographic video capturing device, a radiographic video capturing system, a radiographic video processing method, and a program storage medium that are capable of preventing the occurrence of disruption in displayed images immediately after the binning number is increased, and of improving visual interpretability (visibility) of video that is unstable when image capture conditions are changed, such as when switching to increase the binning number.

A first aspect is a radiographic video processing device including: an acquisition section that acquires gradation signals expressing charges from a radiation detector in which plural pixels are disposed in a matrix formation, each pixel including a sensor portion that generates charges according to irradiated radiation and a switching element that reads charges generated at the sensor portion; and a control section that, if capture of a video image formed from plural frames is being performed with the radiation detector by switching the switching elements ON and OFF to read the charges and converting the read charges to voltage, and a number of the pixels, from which charges are combined and read by the switching elements included in adjacent pixels, has been increased, effects control such that, from a frame at a time of the increase up until a predetermined frame, the gradation signals distributed in a higher density range than that for frames subsequent to the predetermined frame are used as image data.

According to the first aspect, in the radiation detector, the pixels including the sensor portions and the switching elements are disposed in the matrix formation, charges are generated according to irradiated radiation at the sensor portions, and the charges are read by the switching elements. The acquisition section then performs acquisition of gradation signals expressing the charges that have been read.

Although the switching elements generate noise when switched ON or OFF, due to the noise being in reverse directions to each other for the noise when switched ON and the noise when switched OFF, they are cancelled out by integration processing since both types of noise are contained within the period of the conversion operation of the charge to a voltage.

However, when image capture conditions are changed, such as when switching to increase the number of pixels (binning number) from which charges are combined and read, there is a deterioration in images that may be attributable to noise.

As a result of analyzing this issue, it is suspected that the time period during which noise is generated is extended after switching to increase the binning number, and the noise due to switching the switching elements OFF may not be contained within the period of the conversion operation of the charges to voltage.

Therefore, if capture of a video image formed from plural frames is being performed with the radiation detector by switching the switching elements ON and OFF to read the charges and performing the conversion operation of the read charges to voltage, and a number of the pixels, from which charges are combined and read by the switching elements included in the adjacent pixels, has been increased, the control section effects control such that, from a frame at the time of the increase up until the predetermined frame, the gradation signals distributed in a higher density range than that for the frames subsequent to the predetermined frame, are used as image data.

The gradation signals expressing charges read by the radiation detector tend to have distribution on the higher density side immediately after the number of pixels has increased. Therefore, by using, from the frame at the time of the increase in the number of pixels up until the predetermined frame, the gradation signals distributed in a higher density range than that for the frames subsequent to the predetermined frame as image data, it is possible to improve image quality compared to a case using gradation signals over the entire density range as the image data, and also to improve the visual interpretability. Accordingly, visual interpretability of video images, which become unstable when conditions are changed, such as when the binning number is switched, may be improved.

In the first aspect, if the number of pixels has been increased, the control section may effect control such that, from the frame at the time of the increase up until the predetermined frame, dynamic range compression is performed with respect to the gradation signals distributed in the higher density range than that for the frames subsequent to the predetermined frame.

In the first aspect, the control section may further effect control such that, for the frames subsequent to the predetermined frame, a range of the gradation signals used as image data is gradually shifted to a range lower than the higher density range.

The predetermined frame the predetermined frame may be a frame at a time immediately before density fluctuations in the gradation signals, due to switching of the number of pixels, stabilize.

The detection of whether or not the number of pixels has been increased may be detection of satisfaction of a condition of: a transition from a state in which still image capture is performed by the radiation detector to a state in which video image capture is performed by the radiation detector; a frame rate of the video image capture has been increased while performing video image capture by the radiation detector; or a transition from a sequential scanning method in which charges generated in the pixels are read sequentially to a skip scanning method in which charges generated in each of the pixels are read from every other line, per every one line of odd numbered rows or even numbered rows.

A second aspect is a radiographic video capturing device including a radiation detector in which plural pixels are disposed in a matrix formation, each pixel including a sensor portion that generates charges according to irradiated radiation and a switching element that reads charges generated at the sensor portion; and the radiographic video processing device of the first aspect.

A third aspect is a radiographic video capturing system including the radiographic video image capture device of the second aspect; and a radiation irradiation section that irradiates radiation through a subject and onto the radiation detector.

An fourth aspect is a radiographic video processing method including: detecting whether or not a video image formed from plural frames is being captured using a radiation detector in which plural pixels are disposed in a matrix formation, each pixel including a sensor portion that generates charges according to irradiated radiation and a switching element that reads charges generated at the sensor portion, by switching the switching elements ON and OFF to read the charges and converting the read charges to voltage, and detecting whether or not a number of the pixels, from which charges are combined and read by the switching elements included in adjacent pixels, has been increased; and controlling such that, if it is detected that the number of pixels has been increased, the gradation signals expressing the charges distributed in a higher density range than that for frames subsequent to a predetermined frame are used as image data, from a frame at a time of the increase up until the predetermined frame.

According to the fourth aspect, the pixels of the radiation detector respectively include the sensor portions and the switching elements that are disposed in the matrix formation, charges are generated at the sensor portions according to irradiated radiation, and the charges are read by the switching elements.

As described above, it is suspected that the time period during which noise is generated is extended after switching to increase the binning number, and the noise due to switching the switching elements OFF may not be contained within the period of conversion operation from charges to voltage.

Therefore, in the detection step, detection is made as to whether or not a video image formed from plural frames is being captured using the radiation detector by switching the switching elements ON and OFF to read the charges and converting the read charges to voltage, and as to whether or not a number of the pixels, from which charges are combined and read using the switching elements that are included in adjacent pixels, has been increased. In the control step, if it is detected at the detection step that video imaging is being performed and the number of pixels has been increased, control is effected such that, from a frame at the time of the increase up until a predetermined frame, the gradation signals expressing the charges distributed in a higher density range than that for the frames subsequent to the predetermined frame are used as image data.

The gradation signals expressing charges read by the radiation detector tend to have distribution on the higher density side immediately after the number of pixels has been increased. Therefore, by controlling such that, from the frame at the time of the increase in the number of pixels up until the predetermined frame, the gradation signals distributed in a higher density range than that for the frames subsequent to the predetermined frame are used as image data, it is possible to improve image quality compared to a case of employing gradation signals over the entire density range as the image data, and also to improve visual interpretability. Thus, the visual interpretability of video images that become unstable when conditions are changed, such as when the binning number is switched, may be improved.

In the fourth aspect, if the number of pixels has been increased, the controlling may include performing dynamic range compression with respect to the gradation signals distributed in the higher density range than that for frames subsequent to the predetermined frame, from the frame at the time of the increase up until the predetermined frame.

In the fourth aspect, the controlling may further effect control such that, for the frames subsequent to the predetermined frame, a range of the gradation signals used as image data is gradually shifted to a range lower than the higher density range.

The predetermined frame may be a frame at a time immediately before density fluctuations in the gradation signals, due to switching of the number of pixels, stabilize.

The detection of whether or not the number of pixels has been increased may include detecting satisfaction of a condition of: a transition from a state in which still image capture is performed by the radiation detector to a state in which video image capture is performed by the radiation detector; or a frame rate of the video image capture has been increased while performing video image capture by the radiation detector; or a transition from a sequential scanning method in which charges generated in the pixels are read sequentially to a skip scanning method in which charges generated in each of the pixels are read from every other line, per every one line of odd numbered rows or even numbered rows.

A fifth aspect is a non-transitory storage medium storing a program that causes a computer to execute radiographic video processing, the processing including: detecting whether or not a video image formed from plural frames is being captured using a radiation detector in which plural pixels are disposed in a matrix formation, each pixel including a sensor portion that generates charges according to irradiated radiation and a switching element that reads charges generated at the sensor portion, by switching the switching elements ON and OFF to read the charges and converting the read charges to voltage, and detecting whether or not a number of the pixels, from which charges are combined and read by the switching elements included in adjacent pixels, has been increased; and controlling such that, if it is detected that the number of pixels has been increased, the gradation signals expressing the charges distributed in a higher density range than that for frames subsequent to a predetermined frame are used as image data, from a frame at a time of the increase up until the predetermined frame According to the fifth aspect, the pixels of the radiation detector respectively include the sensor portions and switching elements that are disposed in the matrix formation, charges are generated at the sensor portions according to irradiated radiation, and the charges are read by the switching elements.

As described above, it is suspected that the time period during which noise is generated is extended after switching to increase the binning number, and noise due to switching the switching elements OFF may not be contained within the period of conversion operation from charges to voltage.

Therefore, in the detection step the computer performs detection as to whether or not a video image is being captured using the radiation detector by switching the switching elements ON and OFF to read the charges and converting the read charges to voltage, and as to whether or not a number of the pixels, from which charges are combined and read on using the switching elements included in adjacent pixels, has been increased. In the control step, if it is detected at the detection step that video image capture is being performed and the number of pixels has been increased, the computer uses, from a frame at the time of the increase up until a predetermined frame, the gradation signals expressing the charges distributed in a higher density range than that for the frames subsequent to the predetermined frame, as image data.

The gradation signals expressing charges read by the radiation detector tend to have distribution on the higher density side immediately after the number of pixels has increased. Therefore, by controlling such that, from the frame at the time of the increase in the number of pixels up until the predetermined frame, the gradation signals distributed in a higher density range than that for the frames subsequent to the predetermined frame are used as image data, it is possible to improve image quality compared to a case of using gradation signals over the entire density range as the image data, and also to improve the visual interpretability. Thus, visual interpretability of video images that become unstable when conditions are changed, such as when the binning number is switched, may be improved.

In the fifth aspect, if the number of pixels has been increased, the controlling may include performing dynamic range compression with respect to the gradation signals distributed in the higher density range than that for frames subsequent to the predetermined frame, from the frame at the time of the increase up until the predetermined frame.

In the fifth aspect, the controlling may further effect control such that, for the frames subsequent to the predetermined frame, a range of the gradation signals used as image data is gradually shifted to a range lower than the higher density range.

The predetermined frame may be a frame at a time immediately before density fluctuations in the gradation signals, due to switching of the number of pixels, stabilize.

The detection of whether or not the number of pixels has been increased includes detecting satisfaction of a condition of: a transition from a state in which still image capture is performed by the radiation detector to a state in which video image capture is performed by the radiation detector; or a frame rate of the video image capture has been increased while performing video image capture by the radiation detector; or a transition from a sequential scanning method in which charges generated in the pixels are read sequentially to a skip scanning method in which charges generated in each of the pixels are read from every other line, per every one line of odd numbered rows or even numbered rows.

Another aspect is a radiographic image display system including: a radiographic image capture device equipped with a radiation detector in which plural pixels are disposed in a matrix formation, each pixel including a sensor portion that generates charges according to irradiated radiation and a switching element that reads charges generated in the sensor portion; a display section that displays an image captured by the radiographic image capture device; and a control section that, if a condition is satisfied, the condition being than successive image capture is being performed using the radiographic image capture device and a number of the pixels, from which charges are combined and read by the switching elements included in adjacent pixels in the radiographic image capture device, has been increased, controls the display section so as to display frame images up until a predetermined frame number in a state combined with a still image obtained by image capture immediately prior to the condition being satisfied.

According to the present aspect, images are captured by the radiographic image capture device equipped with the radiation detector in which plural pixels are disposed in a matrix formation, each pixel including a sensor portion that generates charges according to irradiated radiation and a switching element that reads charges generated at the sensor portion. These images are displayed on the display section.

In the present aspect, if the condition is satisfied, the condition being that successive image capture is being performed using the radiographic image capture device and a number of pixels (binning number) from which charges are combined and read by the switching elements included in the adjacent pixels in the radiographic image capture device has been increased, the control section controls the display section so as to display frame images up until the predetermined frame number in a state combined with a still image obtained by image capture immediately prior to the condition being satisfied.

Thus, according to the present aspect, if the above condition is satisfied, the frame images up until the predetermined frame number are display in a state combined with a still image obtained by image capture immediately prior to the condition being satisfied, that is a still image with which disruption of the display image does not occur. Therefore, disruption to display images immediately after the binning number has been increased may be prevented.

If the condition is satisfied, the control section may control the display section so as to display the frame images up until the predetermined frame number in state superimposed on a still image obtained by image capture immediately prior to the condition being satisfied. In this way, a smooth transition to display of images actually being captured may be achieved.

In particular, if the condition is satisfied, the control section may control the display section so as to display the frame images up until the predetermined frame number in a state combined (synthesized) with a still image obtained by image capture immediately prior to the condition being satisfied, at a predetermined ratio. In this way, an appropriate display state may be realized according to the preference or purpose of the viewer of the display images, or the type of image capture location to be the display target.

If the condition is satisfied, the control section may control the display section so as to display the frame images up until the predetermined frame number in a state combined with a still image obtained by image capture immediately prior to the condition being satisfied, such that the ratio of the still image to the frame image gradually decreases. In this way, display images may even more smoothly transition the images that are actually being captured.

If the condition is satisfied, the control section may control the display section so as to display the frame images up until the predetermined frame number in a state combined with a still image obtained by image capture immediately prior to the condition being satisfied, with 1:1 ratio of the still image to the frame image. In this way, the images that are actually being captured may also be displayed while preventing disruption of the display images.

If the condition is satisfied, the control section may control the display section so as to display a still image obtained by image capture immediately prior to the condition being satisfied until a frame image partway through the predetermined frame number by gradually fading out the still image, and to display the remaining frame images by gradually fading in the frame images. In this way, display images may even more smoothly transition to the images that are actually being captured.

If the condition is satisfied, the control section may control the display section so as to display a still image obtained by image capture immediately prior to the condition being satisfied for the frame images until a frame image partway through the predetermined frame number, and to display the remaining frame images as they are. In this way, disruption of the display images may be more certainly prevented.

The control section may perform determination as to whether or not the condition is satisfied by determining whether or not a state has been switched from a state in which still image capture is being performed by the radiographic image capture device to a state in which a video image is being captured. Or, the control section may perform determination as to whether or not the condition is satisfied by determining whether or not the frame rate for image capture by the radiographic image capture device has been increased. Or, the control section may perform determination as to whether or not the condition is satisfied by determining whether or not a state has been switched from a state in which progressive scanning is performed by the radiographic image capture device to a state in which interlaced scanning is performed. In such methods, the determination as to whether or not the binning number has been increased may be made more easily.

The present aspect may further include a reception section that receives input of the predetermined frame number. In this way, the predetermined frame number may be easily set.

Another aspect is a radiographic image display device including: a display section that displays an image captured by a radiographic image capture device equipped with a radiation detector in which plural pixels are disposed in a matrix formation, each pixel including a sensor portion that generates charges according to irradiated radiation and a switching element that reads charges generated at the sensor portion; and a control section that if a condition is satisfied, the condition being that successive image capture is being performed using the radiographic image capture device and a number of the pixels, from which charges are combined and read by the switching elements included in adjacent pixels in the radiographic image capture device, has been increased, the control section controls the display section so as to display frame images up until a predetermined frame number in a state combined with a still image obtained by image capture immediately prior to the condition being satisfied.

According to the present aspect, images are captured by the radiographic image capture device equipped with the radiation detector in which plural pixels are disposed in a matrix formation, each pixel including a sensor portion that generates charges according to irradiated radiation and a switching element that reads charges generated at the sensor portion. These images are displayed on the display section.

In the present aspect, if the condition is satisfied, the condition being that successive image capture is being performed using the radiographic image capture device, and a number of pixels (binning number) from which charges are combined and read by the switching elements included in adjacent pixels in the radiographic image capture device has been increased, the display section displays frame images up until the predetermined frame number in the combined state with the still image obtained by image capture immediately prior to the condition being satisfied.

Thus, according to the present aspect, if the above condition is satisfied, the control section effects control of displaying the frame images up until the predetermine frame number in the combined state with the still image obtained by image capture immediately prior to the condition being satisfied, that is, the still image with which disruption of the display image does not occur. Therefore, disruption of display images immediately after the binning number has been increased may be prevented.

Yet another aspect of the present invention is a radiographic image capture device including: a radiation detector in which plural pixels are disposed in a matrix formation, each pixel including a sensor portion that generates charges according to irradiated radiation and a switching element that reads charges generated in the sensor portion; and a generation section that, if a condition is satisfied, the condition being that successive image capture being performed with the radiation detector and a number of the pixels, from which charges are combined and read by the switching elements included in adjacent pixels in the radiographic image capture device, has been increased, generates image data for frame images up until a predetermined frame number by combining each frame image with a still image obtained by image capture immediately prior to the condition being satisfied.

According to the present aspect, if the condition is satisfied, the condition being that successive image capture is being performed with the radiation detector and a number of the pixels, from which charges are combined and read by the switching elements included in adjacent pixels, has been increased, the generation section generates image data for the frame images up until the predetermined frame number by combining the frame images with the still image obtained by image capture immediately prior to the condition being satisfied.

Thus, according to the present if the above condition is satisfied, image data for the frame images up until the predetermined frame number is generated by combining the frame images with the still image obtained by image capture immediately prior to the condition being satisfied, that is, the still image with which disruption in the display image does not occur. Therefore, disruption of display images immediately after the binning number has increased may be prevented.

Yet another aspect of the present invention is a non-transitory storage medium storing a program that causes a computer to execute a processing, the processing including: determining whether or not a condition is satisfied, the condition being that successive image capture is being performed using a radiographic image capture device equipped with a radiation detector in which plural pixels are disposed in a matrix formation, each pixel including a sensor portion that generates charges according to irradiated radiation and a switching element that reads charges generated at the sensor portion, and whether or not a number of the pixels, from which charges are combined and read by the switching elements included in adjacent pixels in the radiographic image capture device, has been increased; and effecting control of, if it is determined that the condition is satisfied, displaying on a display section frame images up until a predetermined frame number in a state combined with a still image obtained by image capture immediately prior to the condition being satisfied.

According to the present aspect, since the computer is able to function in the same manner to the radiographic image display device of the aspect described above, similarly to the radiographic image display device, disruption of display images immediately after the binning number has been increased may be prevented.

Moreover, yet another aspect of the present invention is a radiographic image display method including: determining whether or not a condition is satisfied, the condition being that successive image capture is being performed using a radiographic image capture device equipped with a radiation detector in which plural pixels are disposed in a matrix formation, each pixel including a sensor portion that generates charges according to irradiated radiation and a switching element that reads charges generated at the sensor portion, and whether or not a number of the pixels, from which charges are combined and read by the switching elements included in adjacent pixels in the radiographic image capture device, has been increased; and effecting control of, if it is determined that the condition is satisfied, displaying on a display section frame images up until a predetermined frame number in a state combined with a still image obtained by image capture immediately prior to the condition being satisfied.

Since the present aspect is able to operate in the same manner to the radiographic image display device of the aspect described above, similarly to the radiographic image display device, disruption of display images immediately after the binning number has increased may be prevented.

As explained above, the aspects enables an improvement in visual interpretability of video images that are unstable when conditions are changed, such as when switching to increase the binning number.

Moreover, according to the aspects, if a condition is satisfied, the condition being that successive image capture being performed by the radiographic image capture device and a number of pixels (binning number) from which charges are combined and read by the switching elements included in adjacent pixels in the radiographic image capture device has been increased, a display section is controlled so as to display frame images up until a predetermined frame number in a state combined with a still image obtained by image capture immediately prior to the condition being satisfied, that is, a still image with which disruption in the display image does not occur. Therefore, disruption of display images occurring immediately after an increase in the binning number may be prevented.

BRIEF DESCRIPTION OF THE DRAWINGS

Exemplary embodiments will described in detail based on the following figures.

FIG. 10 is a flow chart illustrating a flow of a radiographic image capture program according to a first exemplary embodiment.

FIG. 11 is a schematic diagram illustrating an example of an initial data input screen according to the exemplary embodiment.

FIG. 22 is a diagram illustrating graph (1) showing an example in which a higher density range is used as image data for a first frame after switching binning number, and graph (2) showing an example in which a lower density range is used as image data for a frame after several frames from the first frame.

FIG. 24 is a block diagram illustrating a schematic configuration of a signal processor of a radiation detector according to an exemplary embodiment.

FIG. 25 is a flow chart illustrating a radiographic image capture preparation control routine according to an exemplary embodiment.

DETAILED DESCRIPTION

Detailed explanation follows regarding exemplary embodiments of the present invention with reference to the drawings. Here, explanation is given regarding an example in which an embodiment is applied to a radiology information system, which is a system that performs overall management of information handled in a hospital radiology department.

First Exemplary Embodiment

Figure 1:
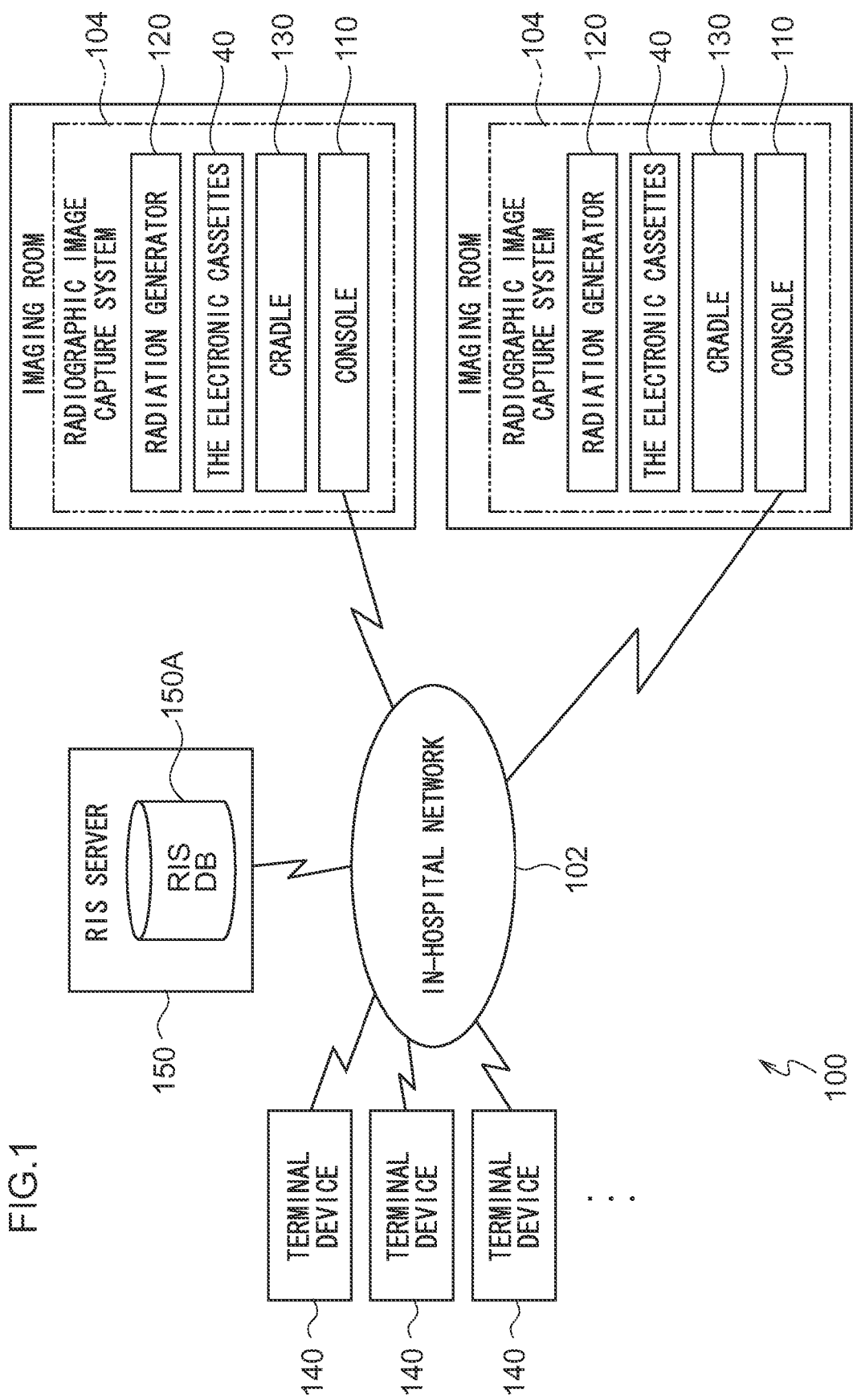
FIG. 1 is a block diagram illustrating a configuration of a radiology information system according to an exemplary embodiment.

Explanation is first given regarding configuration of a radiology information system (referred to hereafter as "RIS") 100 of the present exemplary embodiment with reference to FIG. 1. The RIS 100 is capable of capturing video images in addition to still images. A video image may be defined as still images displayed successively at high speed and thereby give the appearance of a video image, and may be realized by repeating at high speed processes of capturing a still image, converting the still image to an electrical signal, transmitting the electrical signal and reproducing the still image from the transmitted electrical signal. Therefore, depending on the degree of "high speed", video images may also include "frame-by-frame" images in which the same region (part or all) is captured plural times within a predetermined duration and the captured images are successively reproduced.

The RIS 100 is a system for managing information such as medical appointments and diagnostic records in a radiology department and configures part of a hospital information system (referred to below as "HIS").

The RIS 100 includes plural imaging request terminal devices (referred to below as "terminal devices") 140, an RIS server 150, and radiographic image capture systems (referred to below as "imaging systems") 104 that are installed in individual radiographic imaging rooms (or operating rooms) in a hospital. The RIS 100 is configured by respectively connecting the terminal devices 140, the RIS server 150, and the imaging systems 104 to an in-hospital network 102 configured by a wired or wireless local area network (LAN). The RIS 100 configures part of the HIS provided in the same hospital, and an HIS server (not illustrated in the drawings) that manages the entire HIS is also connected to the in-hospital network 102. A single imaging system 104, or three or more imaging systems 104 may be provided. Although in FIG. 1 one imaging system 104 is installed in each imaging room, two or more imaging systems 104 may be installed in a single imaging room.

The terminal devices 140 are used by doctors or radiologists to input and browse diagnostic information and facility reservations. Radiographic imaging requests and imaging reservations are also made using the terminal devices 140. Each of the terminal devices 140 includes a personal computer with a display device, and the terminal devices 140 are configured so as to be capable of intercommunicating with the RIS server 150 through the in-hospital network 102.

The RIS server 150 receives imaging requests from each of the terminal devices 140, manages radiographic imaging schedules in the imaging systems 104, and includes a database 150A.

The database 150A includes: information relating to patients such as patient (subject) attribute information (name, sex, date of birth, age, blood type, body weight, patient identification (ID) and the like), medical histories, consultation histories, radiographic images that have been captured in the past; information relating to electronic cassettes 40, described later, that are used in the imaging systems 104, such as electronic cassette 40 identification numbers (ID information), models, sizes, sensitivities, dates of first use, numbers of times used; and environment information indicating the environments in which radiographic images are captured using the electronic cassettes 40, namely, the environments in which the electronic cassettes 40 are used (such as radiographic imaging rooms or operating rooms). Past personal data of a patient (subject) may be acquired from a server outside of the hospital using, for example, a system (may be referred to as, for example, a "medical cloud") in which medical data managed by a medical institution is retained almost permanently and can be instantly retrieved whenever and wherever required.

The imaging systems 104 are operated by doctors or radiologists to capture a radiographic image in response to an instruction from the RIS server 150. Each of the imaging systems 104 is equipped with a radiation generator 120, an electronic cassette 40, a cradle 130, and a console 110. The radiation generator 120 irradiates a subject with an amount (dose) of radiation X (see also FIG. 6) from a radiation source 121 (see also FIG. 2) according to exposure conditions. The electronic cassette 40 has a built-in radiation detector 20 (see also FIG. 6) that absorbs the radiation X that has passed through an imaging target site of the subject, generates charges, and generates image data expressing a radiographic image based on the amount of generated charges. The cradle 130 charges a battery that is built into the electronic cassette 40. The console 110 controls the electronic cassette 40 and the radiation generator 120.

The console 110 acquires various data contained in the database 150A from the RIS server 150, stores the data in a HDD 116 (see FIG. 8), described later, and uses the data as needed to control the electronic cassette 40 and the radiation generator 120.

Figure 2:
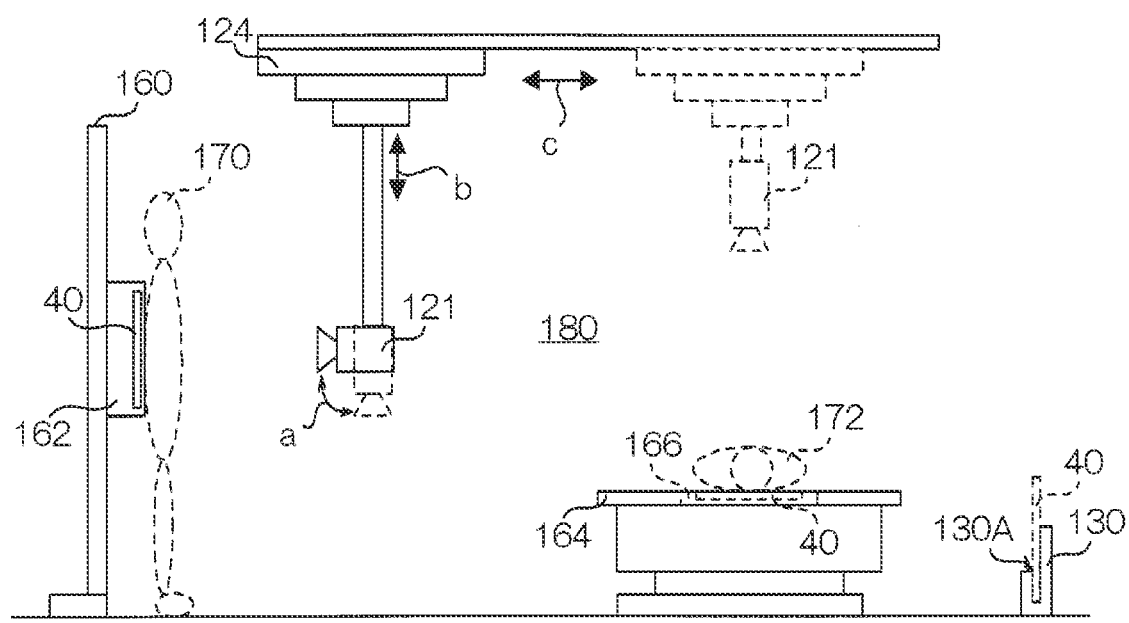
FIG. 2 is a side view illustrating an example of an arrangement in a radiographic imaging room of each device of radiographic image capture system according to an exemplary embodiment.

FIG. 2 illustrates an example of an arrangement of each device of the imaging system 104 of the present exemplary embodiment in a radiographic imaging room 180.

As illustrated in FIG. 2, a standing position stand 160 used when performing radiographic imaging in a standing position, and a recumbent position table 164 used when performing radiographic imaging in a recumbent position, are installed in the radiographic imaging room 180. The space in front of the standing position stand 160 serves as a subject imaging position 170 when performing radiographic imaging in the standing position. The space above the recumbent position table 164 serves as a subject imaging position 172 when performing radiographic imaging in the recumbent position.

A holder 162 that holds the electronic cassette 40 is provided to the standing position stand 160. The electronic cassette 40 is held by the holder 162 in a case in which a radiographic image is captured in the standing position. Similarly, a holder 166 that holds the electronic cassette 40 is provided to the recumbent position table 164. The electronic cassette 40 is held by the holder 166 in a case in which a radiographic image is captured in the recumbent position.

A supporting and moving mechanism 124 is also provided in the radiographic imaging room 180. In order to enable radiographic imaging in both the standing position and in the recumbent position using radiation from the single radiation source 121, the supporting and moving mechanism 124 supports the radiation source 121 such that the radiation source 121 is rotatable about a horizontal axis (the direction of arrow a in FIG. 2), is movable in the vertical direction (the direction of arrow b in FIG. 2), and is movable in the horizontal direction (the direction of arrow c in FIG. 2). The supporting and moving mechanism 124 includes a drive source that rotates the radiation source 121 about the horizontal axis, a drive source that moves the radiation source 121 in the vertical direction, and a drive source that moves the radiation source 121 in the horizontal direction (none of the drive sources are illustrated in the drawings).

A housing portion 130A that houses the electronic cassette 40 is formed in the cradle 130.

When the electronic cassette 40 is not in use, the electronic cassette 40 is housed in the housing portion 130A of the cradle 130, and the built-in battery of the electronic cassette 40 is charged by the cradle 130. When a radiographic image is to be captured, the electronic cassette 40 is removed from the cradle 130 by, for example, a radiologist and is held by the holder 162 of the standing position stand 160 if the imaging posture is the standing position or is held by the holder 166 of the recumbent position table 164 if the imaging posture is the recumbent position.

In the imaging system 104, various data is transmitted and received by wireless communication between the radiation generator 120 and the console 110 and between the electronic cassette 40 and the console 110.

The electronic cassette 40 is not limited to being used in a state held by the holder 162 of the standing position stand 160 or the holder 166 of the recumbent position table 164. Due to its portability the electronic cassette 40 may also be used without being held by a holder, for example, when imaging arm or leg regions.

The radiation detector, described later, is built into the electronic cassette 40. The built-in radiation detector may use an indirect conversion method in which radiation is first converted into light with a scintillator and then the light is converted into charges using a photoelectric conversion element such as a photodiode, or may use a direct conversion method in which radiation is converted into charges with a semiconductor layer such as amorphous selenium. In a radiation detector employing a direct conversion method, a photoelectric conversion layer that absorbs radiation X and converts the radiation X into charge is layered on a TFT active matrix substrate. The photoelectric conversion layer is formed with, for example, non-crystalline a-Se (amorphous selenium) containing selenium as a main component thereof (for example, at a proportion of 50% or above). When the radiation X is irradiated onto the photoelectric conversion layer, the photoelectric conversion layer converts the irradiated radiation X into charges by internally generating charges (electron-hole pairs) with a charge amount corresponding to the amount of irradiated radiation. A radiation detector employing an indirect conversion method may use a fluorescent material and a photoelectric conversion element (photodiode) to indirectly convert the radiation X into charges in place of direct radiation-charge converting materials that directly convert the radiation X into charge such as amorphous selenium. Terbium activated gadolinium oxysulfide ($Gd_2O_2S$:Tb) (abbreviated to GOS) and thallium activated cesium iodide (CsI:Tl) are widely known as fluorescent materials. In such cases conversion of the radiation X into light is performed by the fluorescent material and conversion from light into charges is performed using the photodiode of the photoelectric conversion element. In the present exemplary embodiment a radiation detector employing an indirect conversion method is built into the electronic cassette 40.

Figure 3:
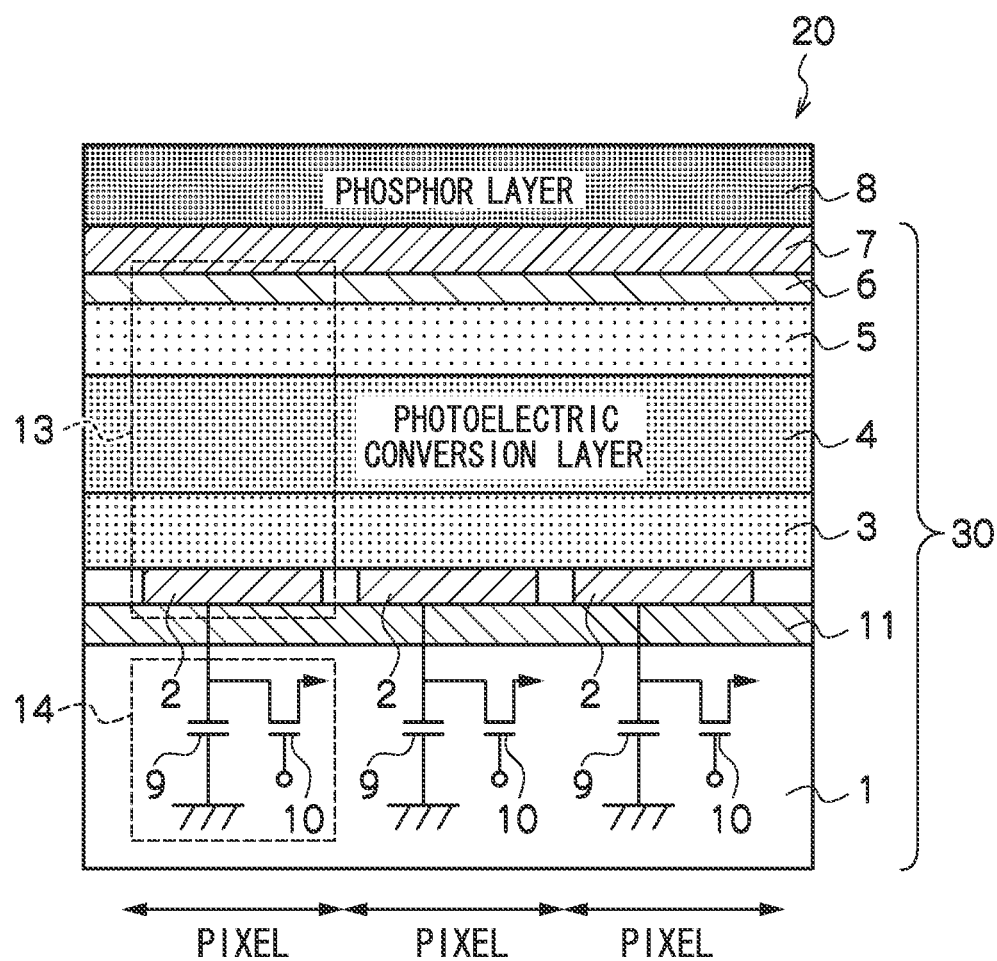
FIG. 3 is a schematic cross-sectional view illustrating a schematic configuration of a portion of a radiation detector including three pixels according to an exemplary embodiment.

Next, explanation follows regarding a configuration of the radiation detector 20 according to the present exemplary embodiment. FIG. 3 is a schematic cross-sectional view illustrating a configuration of a portion of the radiation detector 20 including three pixels according to the present exemplary embodiment.

As illustrated in FIG. 3, in the radiation detector 20, signal output portions 14, sensor portions 13 (TFT substrate 30), and a scintillator 8 are layered in this sequence on an insulating substrate 1, and pixel groups of the ITT substrate 30 are configured by the signal output portions 14 and the sensor portions 13. Namely, plural pixels are arrayed in a matrix formation on the substrate 1 with the signal output portion 14 and the sensor portion 13 overlapping each other in each of the pixels. An insulating film 11 is interposed between the signal output portions 14 and the sensor portions 13.

The scintillator 8 is formed on the sensor portions 13 with a transparent insulating film 7 interposed therebetween. The scintillator 8 is a layer formed of a phosphor material that converts radiation incident thereon from above (the apposite side of the substrate 1) or below into light, and that emits the light. By providing the scintillator 8, light is emitted as result that the scintillator 8 absorbing radiation that has passed through a subject.

It is preferable for the wavelength region of the light emitted by the scintillator 8 to be in the visible light range (a wavelength of 360 nm to 830 nm). It is more preferable for the wavelength region of the light emitted by the scintillator 8 to include a green wavelength region in order to enable monochrome imaging by the radiation detector 20.

As the phosphor used for the scintillator 8, specifically, a phosphor including cesium iodide (CsI) is preferred in cases of imaging using X-rays as the radiation. Using CsI(Tl) (thallium doped cesium iodide) with an emission spectrum of 400 nm to 700 nm when X-rays are applied is particularly preferable. The emission peak wavelength in the visible light range of CsI(Tl) is 565 nm.

The sensor portions 13 include an upper electrode 6, lower electrodes 2, and a photoelectric conversion layer 4 that is placed between the upper electrode 6 and the lower electrodes 2. The photoelectric conversion layer 4 is configured by an organic photoelectric conversion material that absorbs the light emitted by the scintillator 8 and generates charge.

It is preferable for the upper electrode 6 to be configured by a conducting material that is transparent at least with respect to the emission wavelength of the scintillator 8 since it is necessary to allow the light produced by the scintillator 8 to be made incident to the photoelectric conversion layer 4. Specifically, using a transparent conducting oxide (TCO) with high transmittance with respect to visible light and a small resistance value is preferable. A metal thin film of Au or the like may also be employed for the upper electrode 6, however, since its resistance value readily increases when trying to obtain a transmittance of 90% or more, TCO is more preferable. For example, ITO, IZO, AZO, FTO, $SnO_2$, $TiO_2$, $ZnO_2$, and the like are preferably employed. ITO is most preferable from the perspectives of ease of processing, low resistance, and transparency. The upper electrode 6 may have a single configuration common to all the pixels or may be divided per pixel.

The photoelectric conversion layer 4 includes an organic photoelectric conversion material, absorbs the light emitted from the scintillator 8, and generates charges corresponding to the absorbed light. The photoelectric conversion layer 4 containing the organic photoelectric conversion material accordingly has a sharp absorption spectrum in the visible range. Virtually no electromagnetic waves other than the light emitted by the scintillator 8 are absorbed by the photoelectric conversion layer 4, and noise generated as a result of radiation such as X-rays being absorbed by the photoelectric conversion layer 4 can be effectively reduced.

It is preferable for the absorption peak wavelength of the organic photoelectric conversion material configuring the photoelectric conversion layer 4 to be as close as possible to the emission peak wavelength of the scintillator 8 so that the organic photoelectric conversion material most efficiently absorbs the light emitted by the scintillator 8. Ideally the absorption peak wavelength of the organic photoelectric conversion material and the emission peak wavelength of the scintillator 8 are the same as each other, but as long as the difference therebetween is small, the organic photoelectric conversion material can sufficiently absorb the light emitted from the scintillator 8. Specifically, it is preferable for the difference between the absorption peak wavelength of the organic photoelectric conversion material and the emission peak wavelength of the scintillator 8 with respect to radiation to be within 10 nm. The difference is more preferably within 5 nm.

Examples of organic photoelectric conversion materials that satisfy this condition include quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material of the scintillator 8, it is possible to bring the difference between the peak wavelengths to within 5 nm, and the amount of charges generated in the photoelectric conversion layer 4 can be substantially maximized. In the present exemplary embodiment, the photoelectric conversion layer 4 containing an organic photoelectric conversion material is described by way of an example. However, embodiments are not limited thereto, and another material such as amorphous silicon may be employed for the photoelectric conversion layer 4 provided that it is a material that absorbs light and generates charge. In a case in which the photoelectric conversion layer 4 is configured by amorphous silicon, configuration may be made such that the light emitted from the scintillator is absorbed over a wide wavelength region.

Next, specific explanation follows regarding the photoelectric conversion layer 4 applicable to the radiation detector 20 according to the present exemplary embodiment.

An electromagnetic wave absorption/photoelectric conversion region in the radiation detector 20 may be configured by the pair of electrodes 2 and 6 and an organic layer that includes the organic photoelectric conversion layer 4 interposed between the electrodes 2 and 6. More specifically, the organic layer may be formed by stacking or intermingling an electromagnetic wave absorption region, a photoelectric conversion region, an electron-transporting region, a hole-transporting region, an electron-blocking region, a hole-blocking region, a crystallization preventing region, electrodes, and an interlayer contact improving region or the like.

It is preferable for the organic layer to contain an organic p-type compound or an organic n-type compound.

Organic p-type semiconductors compounds) are donor organic semiconductors (compounds) represented mainly by hole-transporting organic compounds and refer to organic compounds having a property of readily donating electrons. More specifically, organic p-type semiconductors (compounds) refer to organic compounds whose ionization potential is the smaller of the two when two organic materials are used in contact with one another. Consequently, any organic compound may be used as the donor organic compound provided that it is an electron-donating organic compound.

Organic n-type semiconductors compounds) are accepter organic semiconductors (compounds) represented mainly by electron-transporting organic compounds and refer to organic compounds having the property of readily accepting electrons. More specifically, organic n-type semiconductors (compounds) refer to organic compounds whose electron affinity is the greater of the two when two organic compounds are used in contact with one another. Consequently, any organic compound can be used as the accepter organic compound provided that it is an electron-accepting organic compound.

Materials applicable as the organic p-type semiconductor and the organic n-type semiconductor, and the configuration of the photoelectric conversion layer 4, are described in detail in JP-A No. 2009-32854, so descriptions thereof will be omitted herein. The photoelectric conversion layer 4 may also be formed so as to further contain fullerenes or carbon nanotubes.

It is preferable for the thickness of the photoelectric conversion layer 4 to be as large as possible from the perspective of absorbing light from the scintillator 8. However, above a certain thickness, the strength of an electric field generated in the photoelectric conversion layer 4 due to a bias voltage applied from both ends of the photoelectric conversion layer 4 drops and charges can no longer be collected. It is therefore preferable for the thickness of the photoelectric conversion layer 4 to be from 30 nm to 300 nm. It is more preferable for the film thickness of the photoelectric conversion layer 4 to be from 50 nm to 250 nm, and it is particularly preferable to be from 80 nm to 200 nm.

In the radiation detector 20 illustrated in FIG. 3, the photoelectric conversion layer 4 has a single configuration common to all the pixels, but the photoelectric conversion layer 4 may also be divided per pixel.

The lower electrodes 2 are configured by thin films divided per pixel. The lower electrodes 2 may be configured by a transparent or opaque electrically conductive material, preferably using, for example, aluminum, silver or the like.

The thickness of the lower electrodes 2 may be, for example, from 30 nm to 300 nm.

In the sensor portions 13, it is possible to move one type of charge (holes or electrons) generated in the photoelectric conversion layer 4 to the upper electrode 6 and the other to the lower electrodes 2 as a result of a predetermined bias voltage being applied between the upper electrode 6 and the tower electrodes 2. In the radiation detector 20, wiring is connected to the upper electrode 6, and the bias voltage is applied to the upper electrode 6 via this wiring. Polarity of the bias voltage is determined here such that the electrons generated in the photoelectric conversion layer 4 move to the upper electrode 6 and the holes move to the lower electrodes 2. However, these polarities may be reversed.

It is sufficient for the sensor portion 13 configuring each of the pixels to include at least the lower electrode 2, the photoelectric conversion layer 4, and the upper electrode 6. However, in order to prevent an increase in dark current, it is preferable to provide at least one of an electron-blocking film 3 or a hole-blocking film 5, and it is more preferable to provide both.

The electron-blocking film 3 may be provided between the lower electrodes 2 and the photoelectric conversion layer 4. The electron-blocking film 3 may suppress dark current from increasing due to electrons being injected from the lower electrodes 2 into the photoelectric conversion layer 4 when the bias voltage has been applied between the lower electrodes 2 and the upper electrode 6.

An electron-donating organic material may be used for the electron-blocking film 3.

It is sufficient for the material that is actually used for the electron-blocking film 3 to be selected in accordance with, for example, the material of the adjacent electrodes and the material of the adjacent photoelectric conversion layer 4. A material whose electron affinity (Ea) is greater by 1.3 eV or more than the work function (Wf) of the material of the adjacent electrodes and has an ionization potential (Ip) equal to or smaller than the ionization potential of the material of the adjacent photoelectric conversion layer 4 is preferred. Materials applicable as the electron-donating organic material are described in detail in JP-A No. 2009-32854, so descriptions thereof will be omitted herein.

In order for the electron-blocking film 3 to reliably exhibit a dark current suppressing effect and to prevent a drop in the photoelectric conversion efficiency of the sensor portions 13, the thickness of the electron-blocking film 3 is preferably from 10 nm to 200 nm. The thickness of the electron-blocking film 3 is more preferably from 30 nm to 150 nm, and is particularly preferably from 50 nm to 100 nm.

The hole-blocking film 5 may be disposed between the photoelectric conversion layer 4 and the upper electrode 6. The hole-blocking film 5 may suppress dark current from increasing due to holes being injected from the upper electrode 6 into the photoelectric conversion layer 4 when bias voltage has been applied between the lower electrodes 2 and the upper electrode 6.

An electron-accepting organic material may be used for the hole-blocking film 5.

In order for the hole-blocking film 5 to reliably exhibit a dark current suppressing effect and to prevent a drop in the photoelectric conversion efficiency of the sensor portions 13, the thickness of hole-blocking film 5 is preferably from 10 nm to 200 nm. The thickness of the hole-blocking film 5 is more preferably from 30 nm to 150 nm, and particularly preferably from 50 nm to 100 nm.

It is sufficient for the material that is actually used for the hole-blocking film 5 to be selected in accordance with, for example, the material of the adjacent electrode and the material of the adjacent photoelectric conversion layer 4, A material whose ionization potential (Ip) is greater by 1.3 eV or more than the work function (Wf) of the material of the adjacent electrode and has an electron affinity (Ea) equal to or greater than the electron affinity of the material of the adjacent photoelectric conversion layer 4 is preferred. Materials applicable as the electron-accepting organic material are described in detail in JP-A No. 2009-32854, so descriptions thereof will be omitted herein.

The positions of the electron-blocking film 3 and the hole-blocking film 5 may be reversed in a case in which the bias voltage is set such that, among the charges generated in the photoelectric conversion layer 4, the holes move to the upper electrode 6 and the electrons move to the lower electrode 2. Further, it is not necessary to provide both of the electron-blocking film 3 and the hole-blocking film 5, and a certain degree of a dark current suppressing effect can be obtained as long as one of them is provided.

Figure 4:
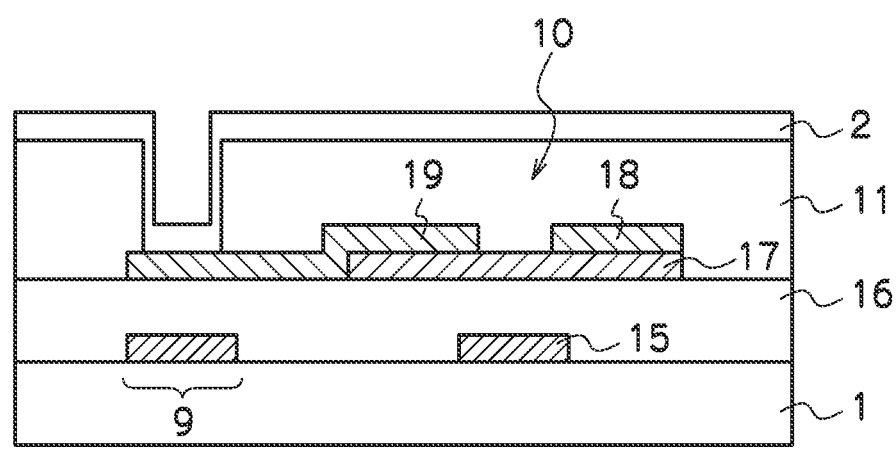
FIG. 4 is a side cross-sectional view schematically illustrating a configuration of a signal output portion of one pixel portion in a radiation detector according to an exemplary embodiment.

The signal output portions 14 are formed on the surface of the substrate 1 below the lower electrodes 2 of each of the pixels. FIG. 4 schematically illustrates the configuration of one of the signal output portions 14.

As illustrated in FIG. 4, in each of the signal output portions 14, a capacitor 9 and a field-effect thin-film transistor (also referred to below as simply "thin-film transistor") 10 are formed corresponding to the lower electrode 2. The capacitor 9 accumulates the charges that have moved to the lower electrode 2. The thin-film transistor 10 converts charges accumulated in the capacitor 9 into an electric signal and outputs the electric signal. The region in which the capacitor 9 and the thin-film transistor 10 are formed has a portion that overlaps the lower electrode 2 in plan view. Due to this configuration, the signal output portion 14 and the sensor portion 13 in each of the pixels overlap with each other in the thickness direction. In order to minimize the plane surface area of the radiation detector 20 (the pixels), it is preferable for the region in which the capacitor 9 and the thin-film transistor 10 are formed to be completely covered by the lower electrode 2.

The capacitor 9 is electrically connected to the corresponding lower electrode 2 by a wire of an electrically conductive material that is formed penetrating the insulating film 11 disposed between the substrate 1 and the lower electrode 2. This enables charges trapped in the lower electrode 2 to move to the capacitor 9.

A gate electrode 15, a gate insulating film 16, and an active layer (channel layer) 17 are layered in the thin-film transistor 10. A source electrode 18 and a drain electrode 19 are formed with a specific spacing from each other on the active layer 17.

The active layer 17 may be formed, for example, by amorphous silicon, an amorphous oxide, an organic semiconductor material, carbon nanotubes, or the like. However, the material configuring the active layer 17 is not limited thereto.

In a case in which the active layer 17 is configured by an amorphous oxide, oxides including at least one of Ga, and Zn (such as In—O amorphous oxides) are preferred, oxides including at least two of In, Ga, and Zn (such as In—Zn—O amorphous oxides, In—Ga—O amorphous oxides, or Ga—Zn—O amorphous oxides) are more preferred, and oxides including In, Ga, and Zn are particularly preferred. As an In—Ga—Zn—O amorphous oxide, an amorphous oxide whose composition in a crystalline state would be expressed by $InGaO_3(ZnO)_m$ (where m is a positive integer less than 6) is preferred, and particularly $InGaZnO_4$ is preferred.

Examples of organic semiconductor materials capable of configuring the active layer 17 include phthalocyanine compounds, pentacene, and vanadyl phthalocyanine, but are not limited to these. Configurations of phthalocyanine compounds are described in detail in JP-A No. 2009-212389, so descriptions thereof will be omitted herein.

By forming the active layer 17 of the thin-film transistor 10 from an amorphous oxide, an organic semiconductor material or carbon nanotubes, the active layer 17 does not absorb radiation such as X-rays, or if it does absorb any radiation the radiation is an extremely minute amount, on the generation of noise in the signal output portion 14 can be effectively reduced.

Further, in a case in which the active layer 17 is formed with carbon nanotubes, the switching speed of the thin-film transistor 10 may be increased, and the thin-film transistor 10 may be formed having a low degree of absorption of light in the visible light range. In cases of forming the active layer 17 with carbon nanotubes, since the performance of the thin-film transistor 10 drops significantly even a tiny amount of a metal impurity is mixed into the active layer 17, it is necessary to separate, extract, and form extremely high-purity carbon nanotubes using centrifugal separation or the like.

The amorphous oxide, organic semiconductor material or carbon nanotubes configuring the active layer 17 of the thin-film transistor 10 and the organic photoelectric conversion material configuring the photoelectric conversion layer 4 are all capable of being formed into films at a low temperature. Consequently, the substrate 1 is not limited to a substrate with high heat resistance, such as a semiconductor substrate, a quartz substrate, or a glass substrate, and aplastic or other flexible substrate, aramids, or bionanofibers can also be used. Specifically, polyester such as polyethylene terephthalate, polybutylene phthalate and polyethylene naphthalate, polystyrene, polycarbonate, polyethersulphone, polyarylate, polyimide, polycyclic olefin, norbornene resin, and poly (chloro-trifluoro-ethylene) or other flexible substrates may be used. By using a flexible substrate made of plastic, the radiation detector can be made lightweight, which is advantageous for portability, for example.

Further, an insulating layer for securing insulation, a gas barrier layer for preventing the transmission of moisture and/ or oxygen, an undercoat layer for improving flatness or adhesion to the electrodes or the like, or other layers may also be disposed on the substrate 1.

Regarding aramids, since high-temperature processes of 200 degrees or higher can be applied, a transparent electrode material can be hardened at a high temperature and given a low resistance. Aramids can also accommodate automatic packaging of driver ICs including solder reflow processes. Aramids have little warping after manufacture and do not break easily since they have a thermal expansion coefficient that is close to that of indium tin oxide (ITO) or a glass substrate. Further, aramids can also form a thinner substrate than a glass substrate or the like. An ultrathin glass substrate and an aramid may be layered to form a substrate.

Bionanofibers are composites of cellulose microfibril bundles (bacterial cellulose) that a bacterium (*Acetobacter xylinum*) produces and a transparent resin. Cellulose microfibril bundles have a width of 50 nm, which is a size that is ⅒ with respect to visible wavelengths, and have high strength, high elasticity, and low thermal expansion. By impregnating and hardening a transparent resin such as an acrylic resin or an epoxy resin in bacterial cellulose, bionanofibers exhibiting a light transmittance of about 90% at a wavelength of 500 nm while including fibers at 60 to 70% can be obtained. Bionanofibers have a low thermal expansion coefficient (3 to 7 ppm) comparable to that of silicon crystal, a strength comparable to steel (460 MPa), high elasticity (30 GPa), and are flexible, therefore enabling the substrate 1 to be formed thinner than a glass substrate or the like.

In the present exemplary embodiment, the TFT substrate 30 is formed by sequentially forming the signal output portions 14, the sensor portions 13, and the transparent insulating film 7 on the substrate 1, and the radiation detector 20 is formed by adhering the scintillator 8 onto the TFT substrate 30 using, for example, an adhesive resin whose light absorbance is low.

Figure 5:
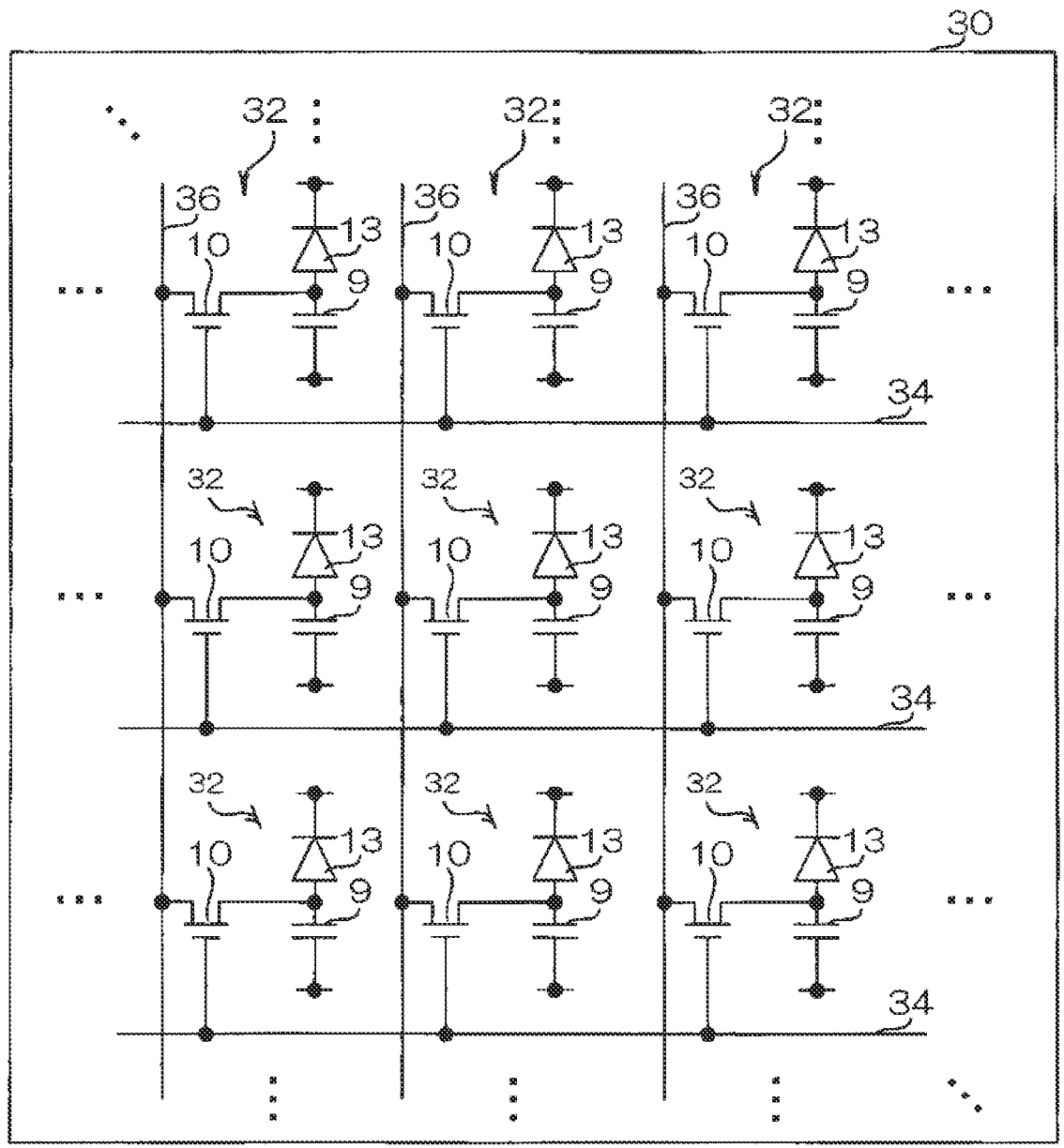
FIG. 5 is a plan view illustrating a configuration of pixels of a radiation detector according to an exemplary embodiment.

FIG. 5 is a diagram illustrating an electrical configuration of the pixels of the radiation detector 20. As illustrated in FIG. 5, on the TFT substrate 30, plural sensor portions 13, the capacitors 9, and pixels 32 configuring the thin-film transistors 10 are disposed two-dimensionally, in one direction (a gate line direction in FIG. 5, which is described later) and in a direction intersecting the one direction (a data line direction in FIG. 5, which is described later).

Moreover, plural gate lines 34 that extend in the one direction and that switch the thin-film transistors 10 ON and OFF, and plural data lines 36 that extend in the intersecting direction and read out charges through the thin-film transistors 10 in an ON state, are provided in the radiation detector 20.

The radiation detector 20 is formed in a tabular quadrilateral shape having four sides on its outer edges in plan view; more specifically, the radiation detector 20 is formed in a rectangular shape.

Figure 6:
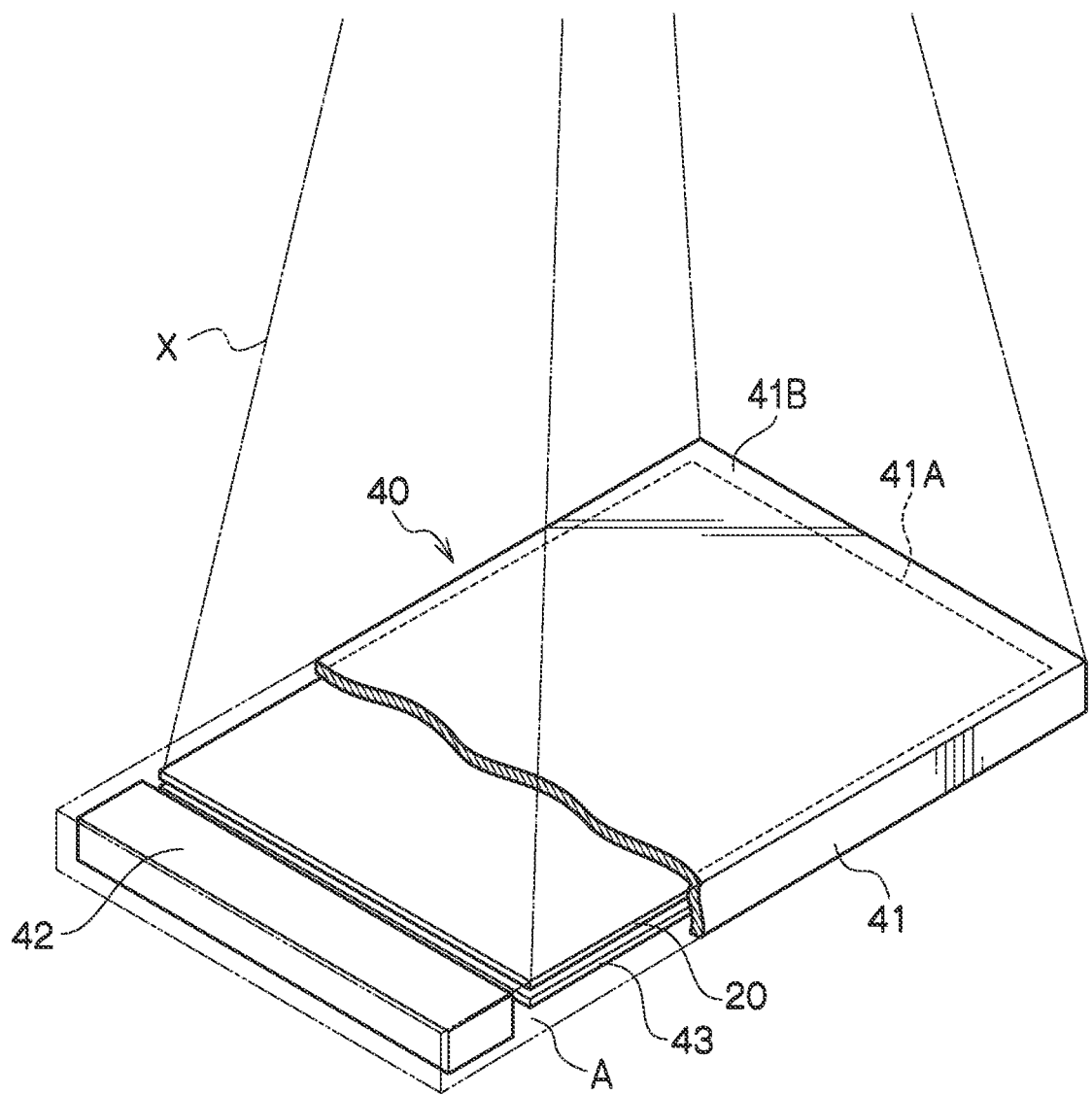
FIG. 6 is a perspective view illustrating a configuration of an electronic cassette according to the exemplary embodiment.

Next, explanation follows regarding a configuration of the electronic cassette 40 according to the present exemplary embodiment. FIG. 6 is a perspective view illustrating the configuration of the electronic cassette 40 according to the present exemplary embodiment.

As illustrated in FIG. 6, the electronic cassette 40 is equipped with a casing 41 that is formed from a material that allows radiation to pass through, and the electronic cassette 40 is configured with a waterproof and airtight structure. When the electronic cassette 40 is used in an operating room or the like, there is the concern that blood or other contaminants may adhere to the electronic cassette 40. Therefore, by configuring the electronic cassette 40 with a waterproof and airtight structure and disinfecting the electronic cassette 40 as needed, the single electronic cassette 40 can be used repeatedly.

A space A that houses various components is formed inside the casing 41. The radiation detector 20, which detects the radiation X that has passed through the subject, and a lead plate 43, which absorbs backscattered rays of the radiation X, are disposed in this order inside the space A from an irradiated surface side of the casing 41 on which the radiation X is irradiated.

In the electronic cassette 40, a region corresponding to the disposed position of the radiation detector 20 on one face of the tabular shape of the casing 41 is configured as a quadrilateral imaging region 41A that is capable of detecting radiation. The face with the imaging region 41A of the casing 41 is configured as a top plate 41B of the electronic cassette 40. In the electronic cassette 40, the radiation detector 20 is disposed such that the TFT substrate 30 is at the top plate 41B side, and the radiation detector 20 is adhered to an inner face of the top plate 41B (the face of the top plate 41B on the opposite side of the face on which the radiation is made incident) in the casing 41.

As illustrated in FIG. 6, a case 42 that houses a cassette controller 58 and a power source section 70, which are described later (see FIG. 8 for both), is placed at one end side of the interior of the casing 41 in a position that does not overlap with the radiation detector 20 (outside the range of the imaging region 41A).

The case 41 is configured by carbon fiber, aluminum, magnesium, bionanofibers (cellulose microfibrils), or a composite material, for example, in order to make the overall electronic cassette 40 lightweight.

As the composite material, for example, a material including reinforced fiber resin is used, and carbon, cellulose, or the like is included in the reinforced fiber resin. Specifically, as the composite material, carbon fiber reinforced plastic (CFRP), a composite material with a structure where a foam material is sandwiched by CFRP, or a composite material in which the surface of a foam material is coated with CFRP may be used. In the present exemplary embodiment, a composite material with a structure where a foam material is sandwiched by CFRP is used. Thereby, the strength (rigidity) of the casing 41 can be raised compared to a case in which the casing 41 is configured by a carbon alone.

Figure 7:
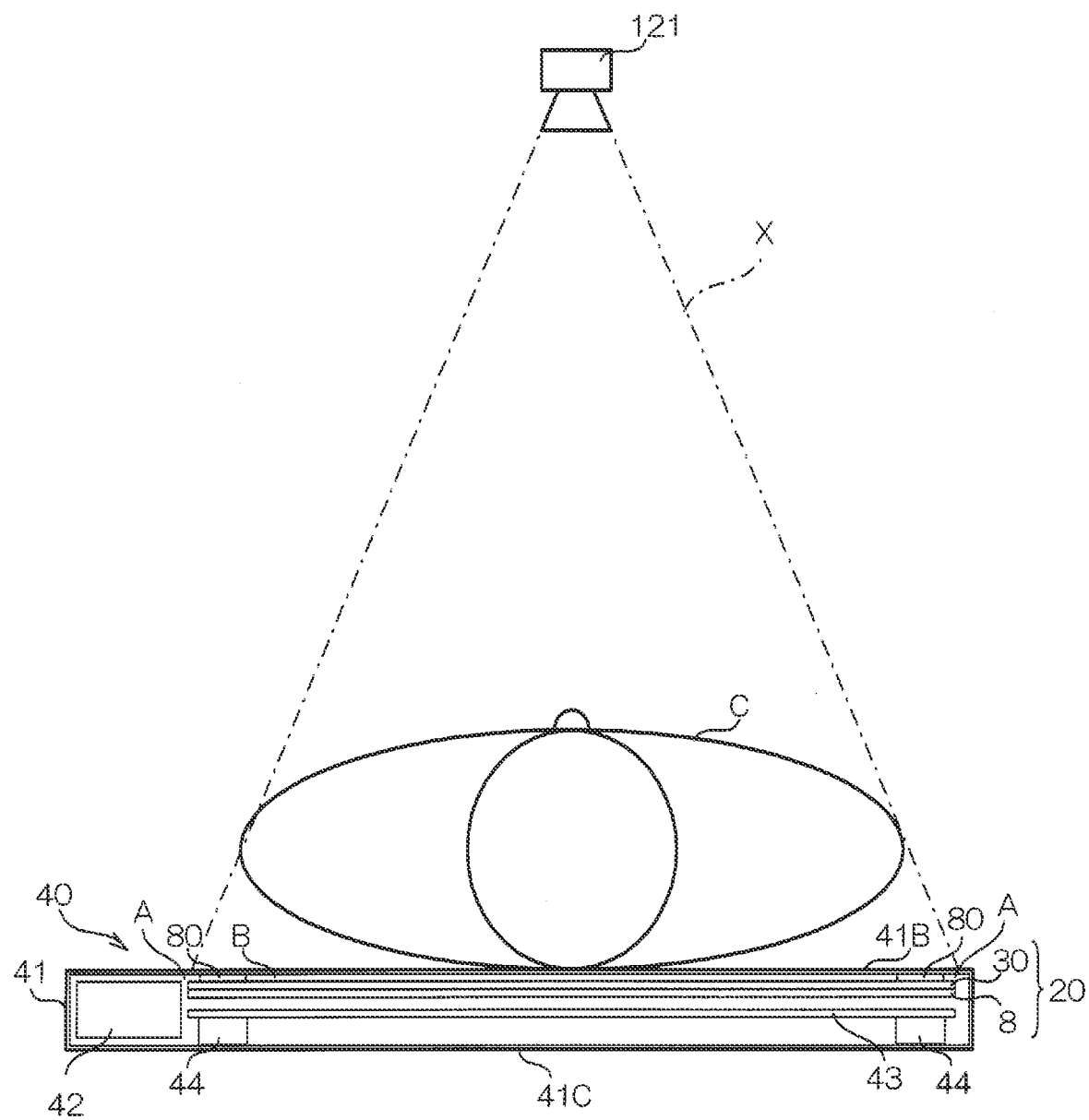
FIG. 7 is a side cross-sectional view illustrating a configuration of an electronic cassette according to an exemplary embodiment.

As illustrated in FIG. 7, inside the casing 41, support bodies 44 are disposed at the inner face of a back face 41C that opposes the top plate 41B. The radiation detector 20 and the lead plate 43 are placed in this order in the irradiation direction of the radiation X between the support bodies 44 and the top plate 41B. The support bodies 44 are configured by a foam material, for example, from the perspective of reducing weight and of absorbing dimensional variation, and the support bodies 44 support the lead plate 43.

As illustrated in FIG. 7, adhesive members 80 that detachably adhere the TFT substrate 30 of the radiation detector 20 are provided at the inner face of the top plate 41B. Double-sided tape, for example, may be used as the adhesive members 80. In this case, the double-sided tape is formed such that the adhesive force of one adhesive surface is stronger than that of the other adhesive surface.

Specifically, the surface having a weak adhesive force weak adhesive surface is set to have a 180-degree peel strength equal to or less than 1.0 N/cm. The surface having a strong adhesive force (strong adhesive surface) contacts the top plate 41B, and the weak adhesive surface contacts the TFT substrate 30. This thereby enables the thickness of the electronic cassette 40 to be made thinner than a case in which the radiation detector 20 is fixed to the top plate 41B by, for example, fixing members such as screws. Further, even if the top plate 41B deforms due to shock or load, since the radiation detector 20 follows the deformation of the top plate 41B, which has high rigidity, only deformation of large curvature (a gentle curve) arises and the potential for the radiation detector 20 to break due to localized low curvature deformation is low. Moreover, the radiation detector 20 contributes to improving the rigidity of the top plate 41B.

In this way, in the electronic cassette 40, since the radiation detector 20 is adhered to the inside of the top plate 41B of the casing 41, the casing 41 can be separated into two between the top plate 41B side and the back face 41C side. The casing 41 may be separated into the two sides of the top plate 41B side and the back face 41C side when the radiation detector 20 is adhered to the top plate 41B or when the radiation detector 20 is detached from the top plate 41B.

In the present exemplary embodiment, the adhesion of the radiation detector 20 to the top plate 41B does not have to be performed in a clean room or the like. This is since even if foreign objects such as metal fragments that absorb radiation have been incorporated between the radiation detector 20 and the top plate 41B, the foreign objects can be removed by detaching the radiation detector 20 from the top plate 41B.

Figure 8:
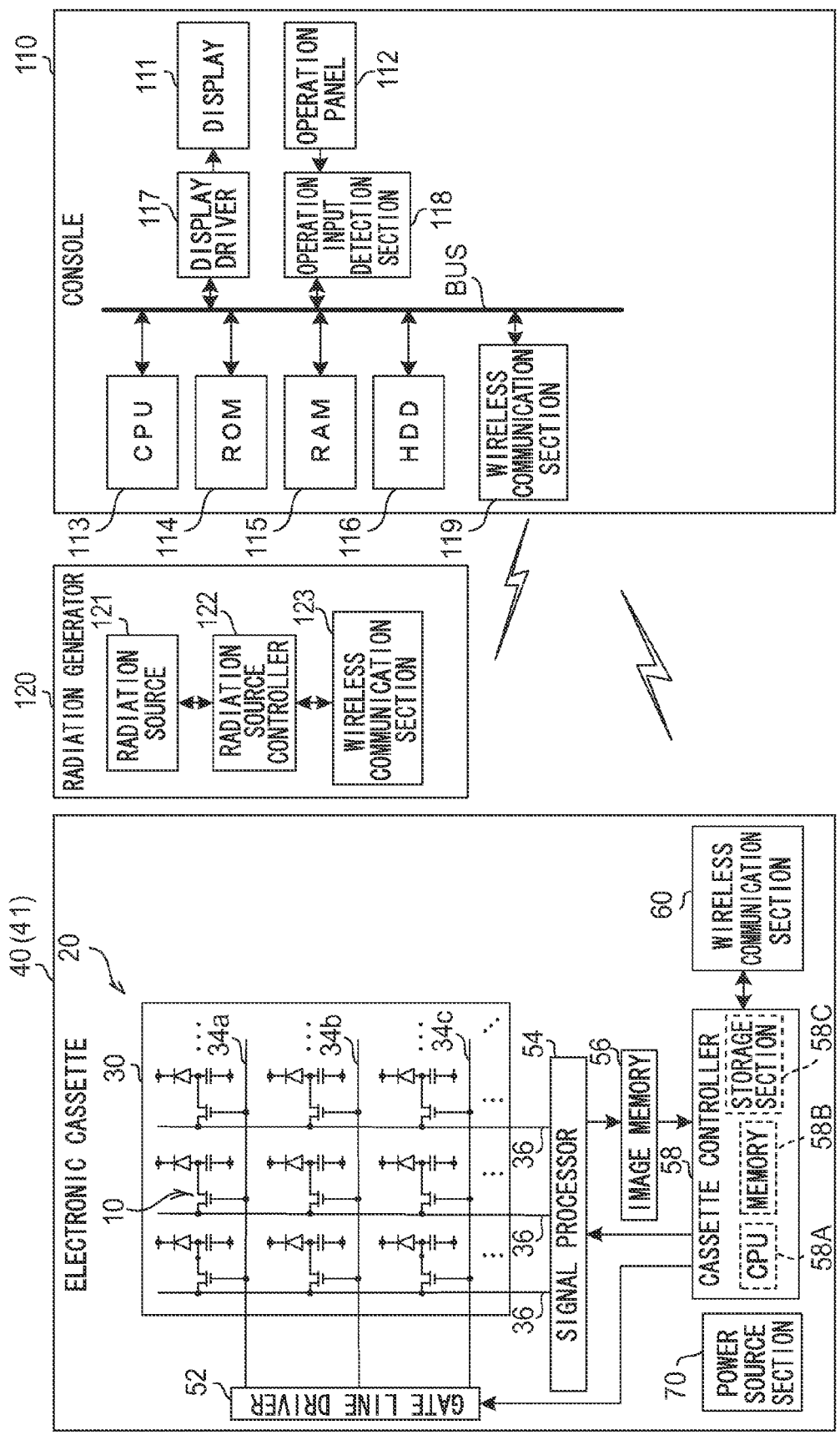
FIG. 8 is a block diagram illustrating relevant configuration in an electrical system of a radiographic image capture system according to an exemplary embodiment.

Next, explanation follows regarding a configuration of relevant portions of an electrical system of the imaging system 104 according to the present exemplary embodiment, with reference to FIG. 8.

As illustrated in FIG. 8, in the radiation detector 20 built into the electronic cassette 40, a gate line driver 52 is placed at one side of two adjacent sides, and a signal processor 54 is placed at the other side. The individual gate lines 34 (in FIG. 8, individually labelled as gate lines 34a, 34b, and so on, with these reference numerals being employed as necessary) of the TFT substrate 30 are connected to the gate line driver 52, and the individual data lines 36 of the TFT substrate 30 are connected to the signal processor 54.

An image memory 56, a cassette controller 58, and a wireless communication unit 60 are also provided inside the casing 41.

A signal supplied from the gate line driver 52 through the gate lines 34 switches ON each of the thin-film transistors 10 in the TFT substrate 30 in sequence in row units, and the charges accumulated in the capacitor 9 of each pixel in which the thin-film transistor 10 has been switched ON are transmitted along the data lines 36 as analogue electrical signals and input to the signal processor 54. The charges accumulated in the capacitors 9 of the individual pixels are thereby read in sequence in row units, enabling a two-dimensional radiographic image to be acquired.

In addition to a sequential scanning method (also referred to as a progressive scanning method) in which, for a single image read operation, the gate line driver 52 outputs an ON signal to each of the gate lines 34 in sequence one line at a time and reads the charges accumulated in the capacitors 9 of each of the pixels one line at a time, a binning read method is also possible. In the binning read method, for a single image read operation, the gate line driver 52 outputs an ON signal to plural gate lines 34 in sequence (for example, two lines or four lines) at a time, and reads the charges accumulated in the capacitors 9 of each of the pixels of the plural lines at a time (combining and reading the charges of the pixels read at the same time). The image read method may be switched between the sequential read method and the binning read method.

The image read method may also be switched between the sequential scanning method and a skipping scanning method (also referred to as an interlace scanning method), in which the gate lines 34 are separated into odd numbered rows and even numbered rows, and for each image read operation, ON signals are respectively output to the gate lines 34 of the odd numbered rows or of the even numbered rows, and charges accumulated in the pixels therein are read from one alternating line.

The cassette controller 58 is connected to the signal processor 54 and the gate line driver 52, and the cassette controller 58 controls the gate line driver 52 and the signal processor 54. The cassette controller 58 is configured as a microcomputer including, for example, a CPU, ROM, RAM, a HDD and flash memory.

Figure 9:
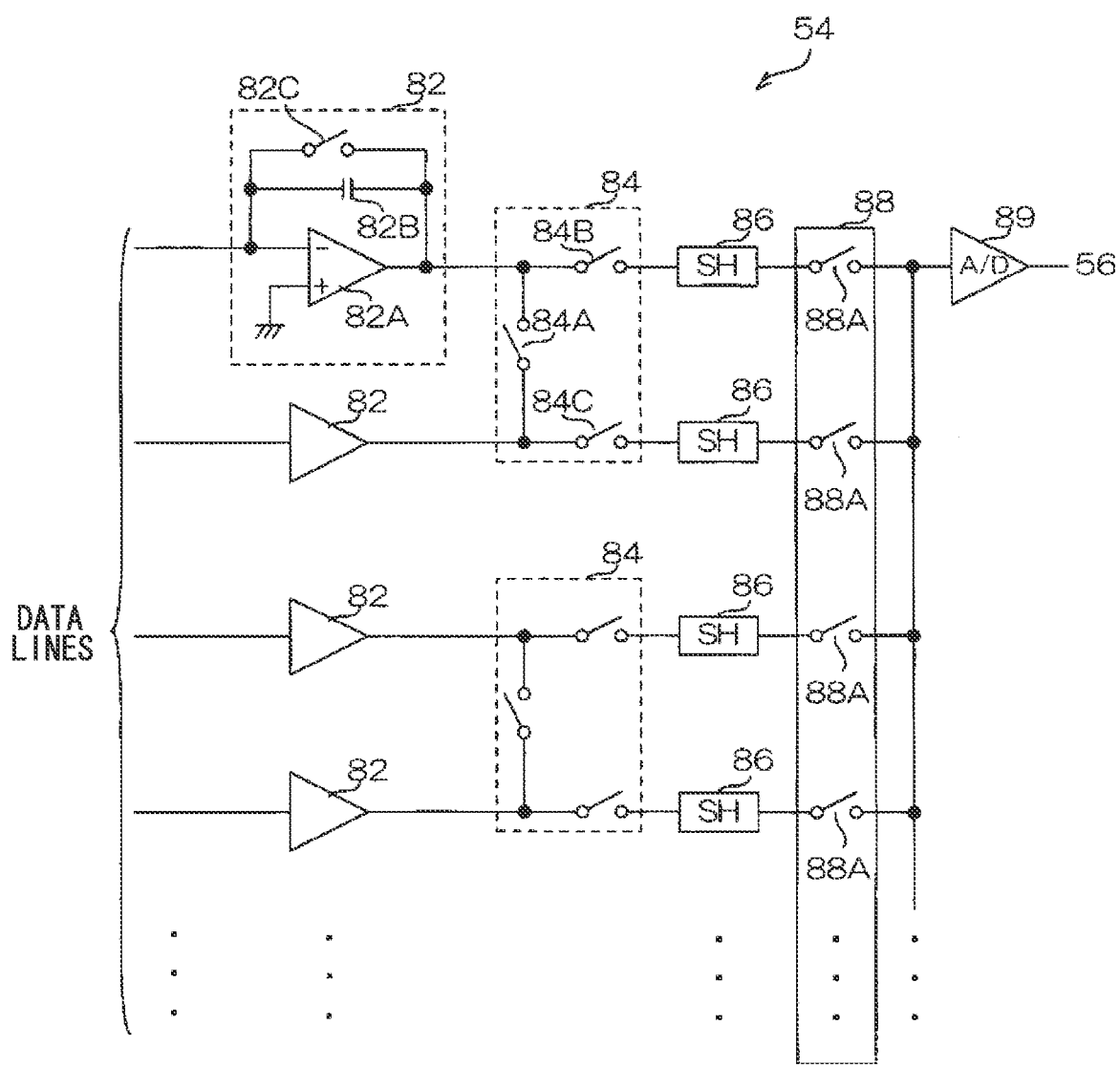
FIG. 9 is a circuit diagram illustrating a configuration of a signal processor according to the exemplary embodiment.

Explanation follows regarding a configuration of the signal processor 54 according to the present exemplary embodiment. FIG. 9 is a circuit diagram illustrating a configuration of the signal processor 54 according to the present exemplary embodiment.

As illustrated in FIG. 9, the signal processor 54 includes variable gain pre-amplifiers (charge amplifiers) 82, binning sections 84, and sample/hold circuits 86 corresponding to each of the data lines 36.

The variable gain (pre-amplifiers 82 are each configured including an operational amplifier 82A that is grounded on the positive input side, a capacitor 82B that is connected in parallel between the negative input side and the output side of the operational amplifier 82A, and a reset switch 82C. The reset switch 82C is switched by the cassette controller 58.

The binning section 84 includes a switch 84A connected between adjacent communication lines, and switches 84B, 84C connected partway along their respective communication lines. Each of the switches 84A, 84B, 84C is also switched by the cassette controller 58. In the present exemplary embodiment, a binning connection state is established by switching ON the switch 84A and the switch 84B, and switching OFF the switch 84C. A normal connection state is established by switching ON the switch 84B and the switch 84C, and switching OFF the switch 84A.

The signal processor 54 is further provided with a multiplexer 88 and an analogue/digital (A/D) converter 89. A sample timing of the sample/hold circuit 86, and the selective output by a switch 88A provided to the multiplexer 88 are switched by the cassette controller 58.

Each of the data lines 36 are individually connected to an input terminal of the multiplexer 88, via the variable gain preamp 82, the binning section 84, and the sample/hold circuit 86 in this sequence. The output terminals of the multiplexer 88 are connected to the input terminal of the A/D converter 89 of which the output terminal is connected to the image memory 56.

During detection of a radiographic image, the cassette controller 58 first switches ON the reset switches 82C of the variable gain preamps 82 for a specific duration, and discharges (resets) the charges accumulated in the capacitors 82B.

Next, the cassette controller 58 switches OFF the reset switches 82C of the variable gain preamps 82, and establishes a binning connection state or a normal connection state by setting the ON/OFF states of the switches 84A to 84C of the binning section 84.

Charges accumulated in the respective capacitors 9 of each of the pixels 32 due to irradiation with the radiation X are transmitted along the connected data lines 36 as electrical signals by switching ON the connected thin-film transistors 10. The electrical signals transmitted along the data lines 36 are amplified by a predetermined amplification ratio by the corresponding variable gain pre-amplifiers 82, and then combined as required by the binning section 84.

After discharging the capacitors 82B and setting the binning sections 84 as described above, the cassette controller 58 drives the sample/hold circuits 86 for a specific duration, thereby causing the sample/hold circuits 86 to hold signal levels of the electrical signals that have been amplified by the variable gain pre-amplifiers 82 and binned (combined as required).

The signal levels held in each of the sample/hold circuits 86 are selected in sequence by the multiplexer 88 according to control by the cassette controller 58, A/D converted by the A/D converter 89, and image data expressing a captured radiographic image is thereby generated.

Figure 17:
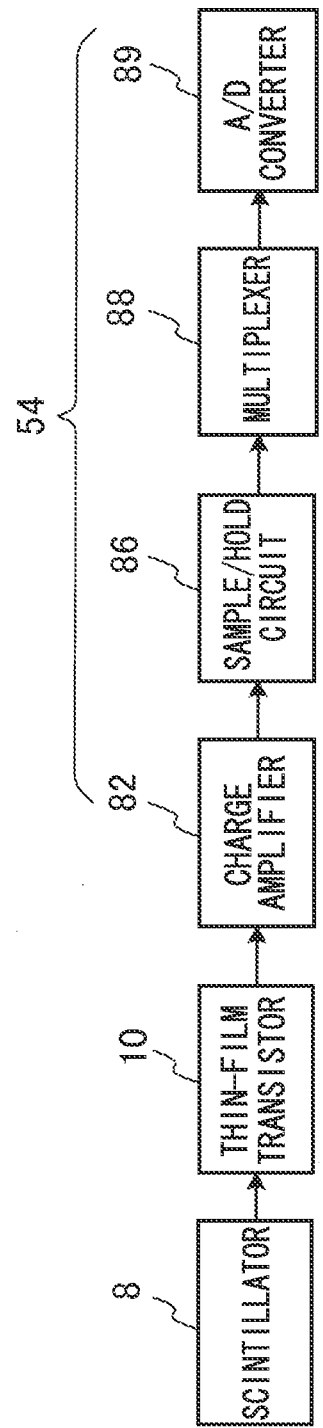
FIG. 17 is a block diagram illustrating a schematic configuration of a signal processor of a radiation detector according to an exemplary embodiment.
Figure 18:
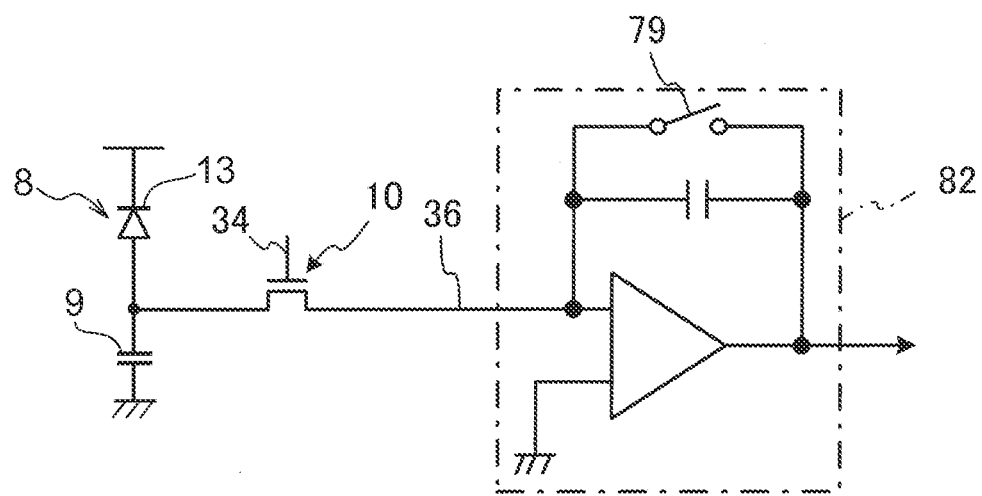
FIG. 18 is a diagram illustrating an equivalent circuit focusing on a single pixel of radiation detector according to an exemplary embodiment.

FIG. 17 is a block diagram illustrating a schematic configuration of the signal processor 54 of the radiation detector 20 according to the present exemplary embodiment. FIG. 18 is a diagram illustrating an equivalent circuit focusing on a single pixel of the radiation detector 20 according to the present exemplary embodiment. Note that the binning section 84 is omitted from illustration FIG. 17.

As illustrated in FIG. 17, charges that have undergone photoelectric conversion by the scintillator 8 are read and output to the signal processor 54 by switching ON the thin-film transistors 10.

As illustrated in FIG. 17, the signal processor 54 is provided with the charge amplifiers 82, the sample/hold circuits 86, the multiplexer 88, and the A/D converter 89.

The charges read from the thin-film transistors 10 are integrated by the charge amplifiers 82, held by the sample/hold circuits 86, and output through the multiplexer 88 to the A/D converter 89. Analogue signals are converted to digital signals by the A/D converter 89 on as to enable image processing.

More specifically, as illustrated in FIG. 18, the sources of the thin-film transistors 10 are connected to the data lines 36, and the data lines 36 are connected to the charge amplifiers 82. The drains of the thin-film transistors 10 are connected to the capacitors 9, and the gates of the thin-film transistors 10 are connected to the gate lines 34.

The electrical signals transmitted along the respective data lines 36 are subjected to integration processing by the charge amplifiers 82 and held in the sample/hold circuits 86. The charge amplifiers 82 are provided with a reset switch 79. The charges are read and the electrical signals are held in the sample/hold circuits 86 while the reset switches 79 are switched OFF.

The electrical signals held in the sample/hold circuits 86 are converted into analogue voltages and input in sequence (serially) to the multiplexer 88, and are converted into digital image data by the A/D converter 89.

The ON/OFF switching of the thin-film transistors 10 and ON/OFF switching of the reset switches 79 of the charge amplifiers 82 are controlled by the cassette controller 58.

The image memory 56 is connected to the signal processor 54, and the image data output from the A/D converter 89 of the signal processor 54 is stored in sequence in the image memory 56. The image memory 56 has sufficient storage capacity to store image data for a specific number of frames, and each time a radiographic image is captured, image data obtained by imaging is sequentially stored in the image memory 56.

The image memory 56 is connected to the cassette controller 58. The cassette controller 58 includes a microcomputer, and is provided with a central processor unit (CPU) 58A, memory 58B including read only memory (ROM) and random access memory (RAM), and a non-volatile storage section 58C configured by for example flash memory. The cassette controller 58 controls overall operation of the electronic cassette 40.

The wireless communication section 60 is also connected to the cassette controller 58. The wireless communication section 60 conforms to a wireless local area network (LAN) standard, typically, for example, the Institute of Electrical and Electronics Engineers (IEEE) standards 802.11 a/b/g/n, and controls transmission of various data via wireless communication to and from an external device. The cassette control section 58 is capable of wireless communication through the wireless communication section 60 with an external device such as the console 110 that controls radiographic image capture, such that it is possible to transmit and receive various data to and from the console 110, for example.

The power source section 70 is provided to the electronic cassette 40, and each of the circuits and each of the elements described above (such as, for example, a microcomputer that functions as the gate line driver 52, the signal processor 54, the image memory 56, the wireless communication section 60, and the cassette controller 58) are operated by power supplied from the power source section 70. The power source section 70 has a built-in battery (a rechargeable secondary battery) so that the portability of the electronic cassette 40 is not compromised, and power is supplied from the charged battery to the various circuits and elements. Wiring connecting the power source section 70 to the various circuits and various elements is omitted from illustration in FIG. 8.

As illustrated in FIG. 8, the console 110 is configured as a server computer, and is provided with a display 111 that displays, for example, an operation menu and captured radiographic images, and an operation panel 112 including plural keys through which various information and operation instructions are input.

The console 110 includes a CPU 113 that controls the operation of the device as a whole, ROM 114 that stores in advance various programs including a control program, and RAM 115 that temporarily stores various data, the hard disk drive (HDD) 116 that stores and holds various data, a display driver 117 that controls display of various information on the display 111, and an operation input detection section 118 that detects an operational state to the operation panel 112. The console 110 transmits and receives various data such as exposure conditions, described later, to and from the radiation generator 120 by wireless communication, and is provided with a wireless communication section 119 that performs transmission and reception of various data such as image data to and from the electronic cassette 40.

The CPU 113, the ROM 114, the RAM 115 the HDD 116, the display driver 117, the operation input detection section 118 and the wireless communication section 119 are mutually connected together through a system bus BUS. The CPU 113 can thereby access the ROM 114, the RAM 115, and the HDD 116, and the CPU 113 can control the display of various information on the display 111 through the display driver 117, and can control the transmission and reception of various data to and from the radiation generator 120 and the electronic cassette 40 through the wireless communication section 119. Through the operation input detection section 118, the CPU 113 can also ascertain an operational state of the operation panel 112 by a user.

The radiation generator 120 is provided with the radiation source 121, a wireless communication section 123 that transmits and receives various data such as exposure conditions to and from the console 110, and a radiation source controller 122 that controls radiation source 121 based on received exposure conditions.

The radiation source controller 122 also includes a microcomputer, and stores received exposure conditions and the like. The exposure conditions received from the console 110 include data relating to tube voltage and tube current. The radiation source controller 122 irradiates the radiation X from the radiation source 121 based on the received exposure conditions.

The imaging system 104 has a fluoroscopic image capture function in which a video image (fluoroscopic image) obtained through image capture is displayed on the display 111 of the console 110 in real time while performing video image capture by the electronic cassette 40, and still image capture is performed by the electronic cassette 40 in response to performance of a predetermined operation (referred to below as a "still image capture instruction operation") by an imaging operator (user), such as operation of the operation panel 112 or press operation of an exposure button that is not illustrated in the drawings.

In the imaging system 104, during video image capture by the electronic cassette 40, the binning sections 84 are set in the binning connection state, and the amount of the radiation from the radiation generator 120 is reduced in comparison to when performing still image capture. In contrast, during still image capture by the electronic cassette 40, the binning sections 84 are set in the normal connection state, and image capture is performed in a state in which radiation is irradiated using exposure conditions set by the user according to the imaging target site.

After still image capture has been performed using the fluoroscopic image capture function, the imaging system 104 returns to video image capture. In a conventional image capture systems, disruption occurs in several frames of displayed video images immediately following this return.

Therefore, the imaging system 104 has a combination display function, in which a preset number of frames (referred to below as "processing target frame number") of the displayed images immediately after returning to video image capture are displayed in a state in which the displayed images are combined with the still image obtained by the immediately prior still image capture.

Next, explanation follows regarding the operation of the imaging system 104 according to the present exemplary embodiment, with reference to FIG. 10. FIG. 10 is a flow chart illustrating a processing flow in a radiographic image capture program executed by the CPU 113 of the console 110 upon input of an instruction to execute the fluoroscopic image capture function through the operation panel 112. The program is stored in advance in a specific region of the ROM 114. In order to avoid complication, explanation is given regarding an example in which the radiation exposure conditions (in the present exemplary embodiment, the tube voltage and tube current during radiation X exposure) during video image capture by the electronic cassette 40 are set in advance.

At step 300 in FIG. 10, the display driver 117 is controlled so as to display a predetermined initial data input screen on the display 111, and at the next step 302 the console 110 stands by for specific data input.

FIG. 11 illustrates an example of the initial data input screen displayed by the display 111 by the processing of step 300. As illustrated in FIG. 11, the initial data input screen displays messages prompting input of the name of the subject for radiographic image capture, imaging target site, posture during imaging, radiation X exposure conditions for still image capture (tube voltage, tube current, and exposure duration during radiation X exposure in the present exemplary embodiment), and the processing target frame number described above, and displays input fields for such information.

After the initial data input screen illustrated in FIG. 11 has been displayed by the display 111, the user may input the name of the subject for image capture, the imaging target site, the posture for image capture, the exposure conditions, and the processing target frame number to each corresponding input field using the operation panel 112.

In a case in which the posture during imaging is a standing posture or a recumbent posture, the user may place the electronic cassette 40 on the corresponding holder 162 of the standing position stand 160 or the holder 166 of the recumbent position table 164, position the radiation source 121 at a corresponding position, and then position the subject at a specific imaging position. However, in a case in which the imaging target site is, for example, an arm portion or a leg portion and radiographic image capture is performed in a state in which the electronic cassette 40 is not held on a holder, the user may position the subject, the electronic cassette 40 and the radiation source 121 into a state that enables imaging of the imaging target site. Then, the user may designate a COMPLETE button displayed in the vicinity of the lower edge of the initial data input screen using the operation panel 112. Affirmative determination is made at step 302 in response to the COMPLETE button being designated the user, and processing transitions to step 304.

At step 304, the data that has been input in the initial data input screen (referred to below as "initial data") is transmitted to the electronic cassette 40 using the wireless communication section 119. Then at the next step 306 the preset exposure conditions for video image capture are transmitted to the radiation generator 120 using the wireless communication section 119 to set the exposure conditions in the radiation generator 120. In response, the radiation source controller 122 of the radiation generator 120 prepares for exposure with the received exposure conditions.

At the next step 308, instruction data instructing initiation of exposure is transmitted to the radiation generator 120, and instruction data instructing initiation of video image capture is transmitted to the electronic cassette 40. In response, the radiation source 121 generates the radiation X at a tube voltage and tube current corresponding to the exposure conditions received by the radiation generator 120 from the console 110 and performs irradiation of the radiation X.

The radiation X irradiation from the radiation source 121 arrives at the electronic cassette 40 after passing through the subject. Charges are accordingly accumulated in the capacitors 9 of each of the pixels 32 of the radiation detector 20 that is built into the electronic cassette 40.

Upon receipt of instruction data instructing initiation of video image capture, the cassette controller 58 of the electronic cassette 40 places the binning section 84 in the binning connection state. Then, after a predetermined duration that is until charge accumulation in the capacitors 9 of each of the pixels 32 of the radiation detector 20 is completed, the cassette controller 58 controls the gate line driver 52 such that an ON signal is output from the gate line driver 52 to each of the gate lines 34 in sequence one line at a time, thereby switching ON each of the thin-film transistors 10 connected to each of the gate lines 34 in sequence one line at a time.

In the radiation detector 20, in response to each of the thin-film transistors 10 connected to each of the gate lines 34 being switched ON in sequence one line at a time, the charges accumulated in each of the capacitors 9 flow out in sequence into each of the data tines 36 as electrical signals one line at a time. The electrical signals that flow out into each of the data lines 36 are converted into digital image data by the signal processor 54, and stored in the image memory 56.

After performing predetermined image correction processing on the image data stored in the image memory 56, the cassette controller 58 then transmits the image data stored in the image memory 56 to the console 110 using the wireless communication section 60.

The cassette controller 58 performs video image capture by executing the above operation at a (predetermined rate that is a video image capture rate at 30 frames/second in the present exemplary embodiment).

At the next step 310, the console 110 stands by until one frame worth of image data has been received from the electronic cassette 40, and at the next step 312, controls the display driver 117 such that a radiographic image expressed by the received image data is displayed on the display 111.

Figure 12:
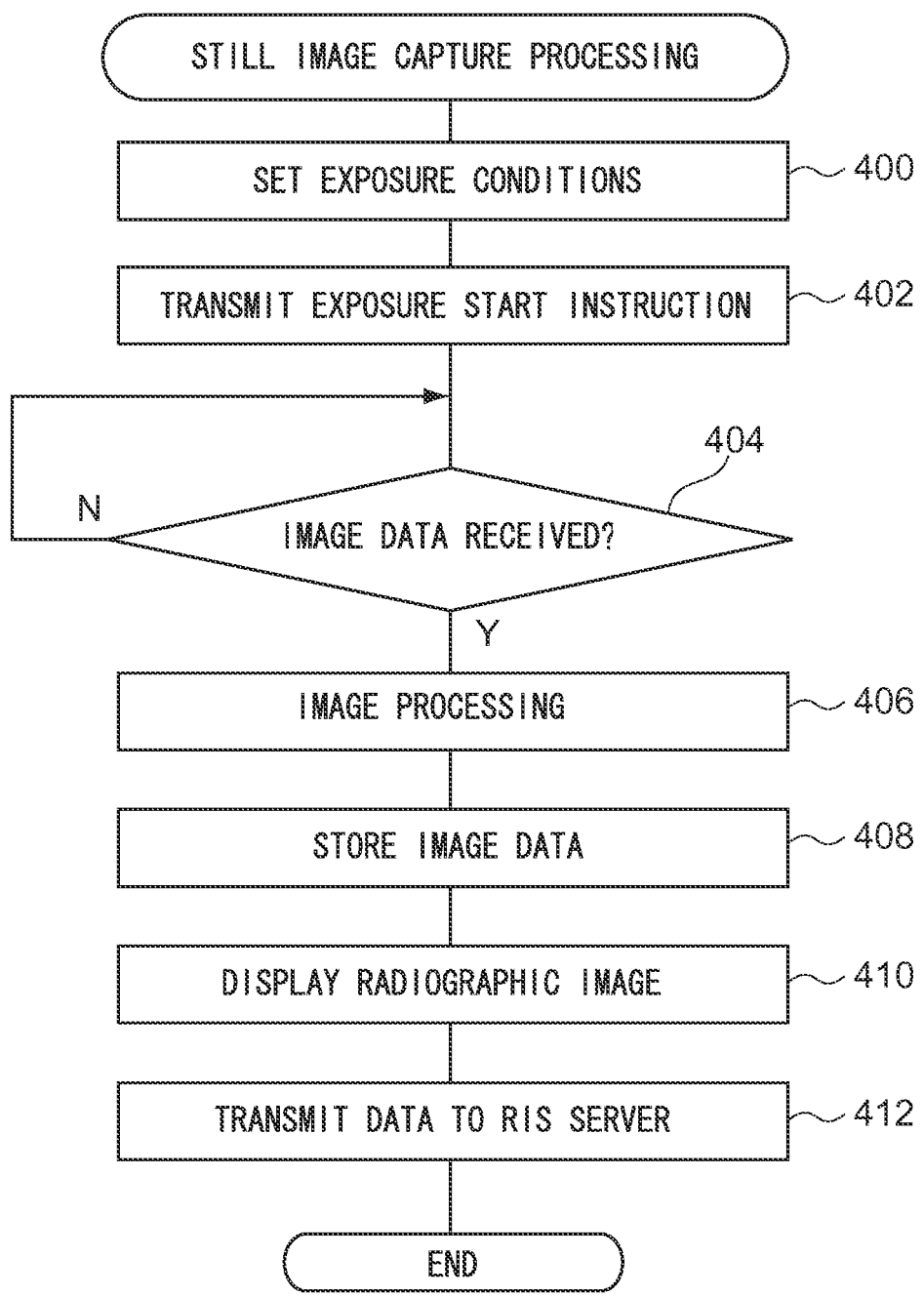
FIG. 12 is a flow chart illustrating a flow of a still image capture routine program according to an exemplary embodiment.

At the next step 314, determination is made as to whether or not the still image capture instruction operation described above has been performed. If the determination is affirmative, processing transitions to step 316, and a still image capture routine program is executed. Explanation follows regarding the still image capture routine program according to the present exemplary embodiment, with reference to FIG. 12. FIG. 12 is a flow chart of a processing flow of the still image capture routine program, and this program is stored in advance in a specific region of the ROM 114.

At step 400 illustrated in FIG. 12, the exposure conditions contained in the initial data are transmitted to the radiation generator 120 through the wireless communication section 119, thereby setting the exposure conditions to the radiation generator 120. In response, the radiation source controller 122 of the radiation generator 120 prepares for exposure with the received exposure conditions.

At the next step 402, instruction data instructing initiation of exposure with the set exposure conditions is transmitted to the radiation generator 120, and instruction data instructing initiation of still image capture is transmitted to the electronic cassette 40.

In response, the radiation source 121 starts irradiation of the radiation X with the tube voltage, tube current and exposure duration corresponding to the exposure conditions received by the radiation generator 120 from the console 110. The radiation X irradiation from the radiation source 121 arrives at the electronic cassette 40 after passing through the subject.

Upon receipt of the instruction data instructing initiation of still image capture, the cassette controller 58 of the electronic cassette 40 places the binning section 84 in the normal connection state, and then performs still image capture through substantially the same operation as that described above for video image capture. The image data obtained thereby is subjected to predetermined image correction processing, after which it is transmitted to the console 110 using the wireless communication section 60.

Then, at the next step 404, the console 110 stands by until the image data is received from the electronic cassette 40, and at the next step 406 executes image processing to perform various corrections such as shading correction on the received image data.

At the next step 408, the image data on which the above processing has been performed (referred to below as "still image data") is stored in the HDD 116, and at the next step 410, the console 110 controls the display driver 117 to display a radiographic image expressed by the still image data on the display 111 for a specific duration for checking, for example.

At the next step 412, the still image data is transmitted to the RIS server 150 through the in-hospital network 102, after which the current still image capture routine program is ended. The still image data transmitted to the RIS server 150 is stored in a database 15A, and the captured radiographic image may be used by a medical professional to perform, for example, interpretation or diagnosis.

After completion of the still image capture routine program, processing transitions to step 318 of the main program, the radiographic image capture program (FIG. 10). Similarly to step 306 described above, exposure conditions are set to the radiation generator 120 by transmitting the preset exposure conditions for video image capture to the radiation generator 120 using the wireless communication section 119. In response, the radiation source controller 122 of the radiation generator 120 prepares for exposure with the received exposure conditions.

At the next step 320, instruction data instructing initiation of exposure is transmitted to the radiation generator 120, and instruction data instructing initiation of video image capture is transmitted to the electronic cassette 40. In response, the radiation source 121 generates radiation with the tube voltage and tube current corresponding to the exposure conditions received by the radiation generator 120 from the console 110, and performs irradiation of the radiation. When the instruction data instructing initiation of video image capture is transmitted to the electronic cassette 40 in the processing of step 320, the CPU 113 determines that the electronic cassette 40 has been switched from the state of performing still image capture to the state of performing video image capture, and thereafter executes the combination display function described above.

Upon receipt of the instruction data instructing initiation of video image capture, the electronic cassette 40 operates similarly to during the video image capture described above, and successively transmits the image data obtained by the video image capture to the console 110 using the wireless communication section 60.

At the next step 322, the console 110 stands by until one frame worth of image data is received from the electronic cassette 40. At the next step 324, the console 110 generates synthesized image data by superimposing on the received image data (referred to below as "video image data") the stored still image data that has been received from the electronic cassette 40 during the still image capture routine program performed immediately beforehand.

In the imaging system 104, at step 324 the video image data and the still image data are superimposed by computing weighted average values for the pixel data of their corresponding pixels, such that the ratio of the still image data to the video image data be a predetermined ratio (60% in the present exemplary embodiment).

At the next step 326, the console 110 controls the display driver 117 so as to display on the display 111a radiographic image expressed by the synthesized image data obtained by the processing of step 324.

At the next step 328, determination is made as to whether or not the number of frames of radiographic images displayed by the processing of step 322 to step 326 has reached the processing target frame number included in the initial data. If the determination is negative, processing returns to step 322, and if the determination is affirmative, processing returns to step 310.

If the determination is negative at step 314, processing transitions to step 330, and determination is made as to whether or not a timing for ending execution of the fluoroscopic image capture function has been reached. If the determination is negative, processing returns to step 310, and if the determination is affirmative, processing transitions to step 332. In the imaging system 104, the determination in step 330 as to whether or not the timing for ending execution of the fluoroscopic image capture function has been reached is performed by determining whether or not the user has performed an operation through the operation panel 112 of the console 110 to instruct the fluoroscopic image capture function to be terminated. However, embodiments are obviously not limited thereto.

At step 332, the console 110 transmits instruction data instructing termination of radiation exposure to the radiation generator 120, and then the current radiographic image capture program is ended.

As illustrated in FIG. 7, the radiation detector 20 is built into the electronic cassette 40 such that the radiation X is irradiated from the TFT substrate 30 side.

Figure 13:
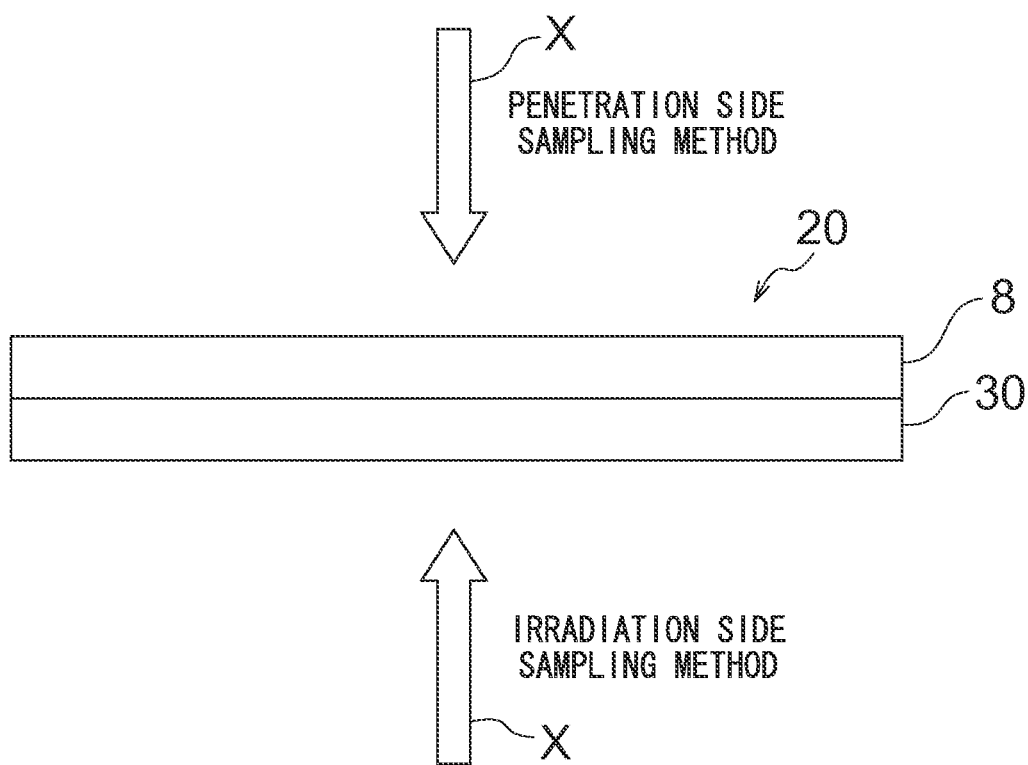
FIG. 13 is a side cross-sectional view for explaining irradiation side sampling methods and penetration side sampling methods for radiographic images.

In cases in which the radiation detector 20 adopts a penetration side sampling method, in which the radiation detector 20 is irradiated with radiation from the side where the scintillator 8 is formed as illustrated in FIG. 13, and radiographic images are read by the TFT substrate 30 provided at the back side with respect to the radiation incident face, the scintillator 8 emits light with higher intensity at the upper side in FIG. 13 (the side opposite to the TFT substrate 30). However, in cases in which the radiation detector 20 adopts an irradiation side sampling method, in which the radiation detector 20 is irradiated with radiation from the TFT substrate 30 side, and radiographic images are read by the TFT substrate 30 provided at the front side of the radiation incident face, since radiation that has passed through the TFT 30 is incident to the scintillator 8, the scintillator emits light with higher intensity at the TFT substrate 30 side. Each of the sensor portions 13 provided to the TFT substrate 30 generates charges due to the light generated by the scintillator 8. The radiation detector 20 therefore gives a higher resolution of captured radiographic images in cases of adopting an irradiation side sampling method than adopting a penetration side sampling method, since the light emission position of the scintillator 8 is closer to the TFT substrate 30.

The radiation detector 20 is configured with the photoelectric conversion layer 4 formed from an organic photoelectric conversion material and, therefore, radiation is barely absorbed by the photoelectric conversion layer 4. Accordingly, in the radiation detector 20, the amount of radiation absorbed by the photoelectric conversion layer 4 is low even if an irradiation side sampling method is adopted and radiation passes through the TFT substrate 30. Any drop in sensitivity to radiation can hence be suppressed. In an irradiation side sampling method, radiation reaches the scintillator 8 after passing through the TFT substrate 30. However, configuring the photoelectric conversion layer 4 of the TFT substrate 30 by an organic photoelectric conversion material is suitable for an irradiation side sampling method since hardly any radiation is absorbed in the photoelectric conversion layer 4 and radiation attenuation can be suppressed to a small amount.

Further, both the amorphous oxide material configuring the active layer 17 of the thin-film transistors 10 and the organic photoelectric conversion material configuring the photoelectric conversion layer 4 can be formed into a film at low temperature. Therefore, the substrate 1 can be formed from a plastic resin, aramids or bionanofibers, which have low absorptivity to radiation. Since the amount of radiation absorbed by the thus formed substrate 1 is small, it is possible to prevent drop in sensitivity to radiation even if an irradiation side sampling method is adopted and radiation passes through the TFT substrate 30.

In the present exemplary embodiment, as illustrated in FIG. 7, the radiation detector 20 is affixed to the top plate 41B inside the casing 41 such that the TFT substrate 30 is disposed at the top plate 41B side. In cases in which the substrate 1 is formed from a high rigidity plastic resin, aramids or bionanofibers, the top plate 41B of the casing 41 can be formed thinner since the rigidity of the radiation detector 20 itself is high. Further, in cases in which the substrate 1 is formed from a high rigidity plastic resin, aramids or bionanofibers, the radiation detector 20 is not readily damaged even if shock is imparted to the imaging region 41A since the radiation detector 20 itself is flexible.

As explained in detail above, according to the present exemplary embodiment, if a condition is satisfied, the condition being that successive image capture is being performed by the radiographic image capture device (by the electronic cassette 40 in the present exemplary embodiment), and a number of pixels (binning number) from which charges are combined and read by the switching elements included in adjacent pixels in the radiographic image capture device has been increased, frame images up until a predetermined frame number (the processing target frame number in the present exemplary embodiment) are displayed in a state combined with a still image obtained by image capture immediately prior to the condition being satisfied, namely, a still image with which disruption in the display image does not occur. Thereby, disruption of display images immediately after an increase in the binning number may be prevented.

In particular, in the present exemplary embodiment, if the condition has been satisfied, the frame images up until the predetermined frame number are displayed in a state in which the still image obtained by image capture immediately prior to the condition being satisfied is superimposed thereon. Thereby, a smooth transition to a display of the actual images being captured may be achieved.

Moreover, in the present exemplary embodiment, if the condition has been satisfied, the frame images until the predetermined frame number are displayed by being combined with the still image obtained by image capture immediately prior to the condition being satisfied at a predetermined ratio. Therefore, a suitable display may be achieved by setting the ratio according to the preference of the user, the purpose, or the type of the image capture target site that is a display target.

In the present exemplary embodiment, determination as to whether or not the condition has been satisfied is made by determining whether or not there has been a switch from a state in which still image capture is performed by the radiographic image capture device to a state in which video image capture is performed by the radiographic image capture device. Therefore, determination as to whether or not the binning number has been increased can be made easily.

In the present exemplary embodiment, the predetermined frame number may be set easily by receiving input of the predetermined frame number.

Although explanation has been given regarding a case in which determination as to whether or not the condition has been satisfied is performed by determining whether or not there has been a switch from the state of in which still image capture is performed by the electronic cassette 40 to the state in which video image capture is performed by the electronic cassette 40, embodiments are not limited thereto. This determination may be made by determining whether or not the frame rate of image capture by the electronic cassette 40 has been increased. Or, the electronic cassette 40 may be configured to read image data by progressive scanning during still image capture and to read image data by interlaced scanning during video image capture, and the determination as to whether or not the condition has been satisfied may be made by determining whether or not the state in which progressive scanning is performed by the electronic cassette 40 has been switched to the state in which interlaced scanning is performed by the electronic cassette 40. These configurations also enable easy determination of whether or not the binning number has been increased.

In the present exemplary embodiment, explanation has been given regarding a case in which proportions of the still image data and the video image data are different for all of the displayed images of the processing target frame number (in the present exemplary embodiment, the ratio of still image data to video image data is 60%). However, embodiments are not limited thereto, and the proportions may be the same (i.e., the ratio of still image data to video image data may be 50%). Similar effects to that in the present exemplary embodiment may also be achieved by this configuration.

Second Exemplary Embodiment

Next, detailed explanation is given regarding a second exemplary embodiment. Since configurations of a RIS 100, a radiographic imaging room, an electronic cassette 40 and an imaging system 104 according to the second exemplary embodiment are the similar to those of the first exemplary embodiment, explanation thereof is omitted herein.

Figure 14:
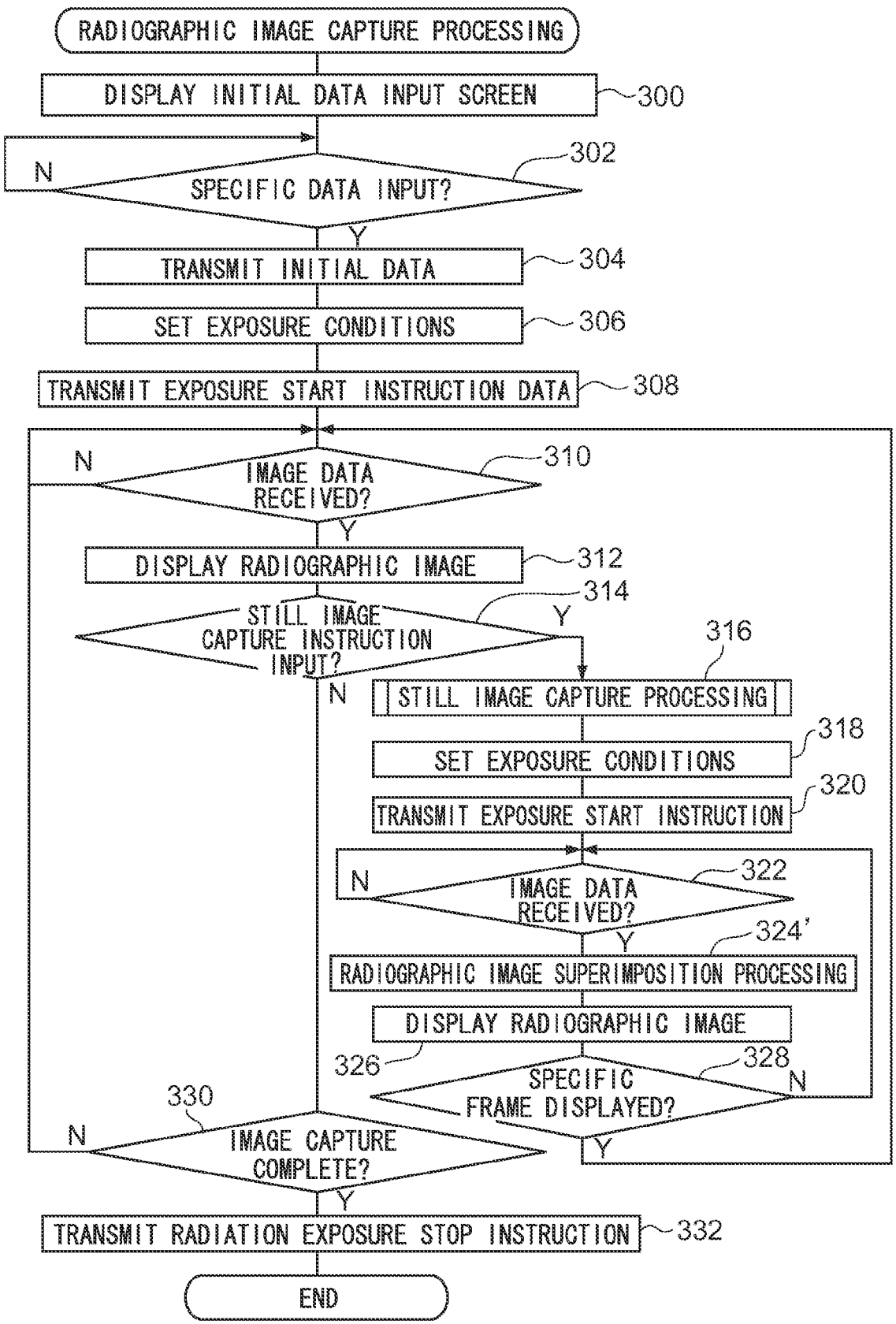
FIG. 14 is a flow chart illustrating a flow of a radiographic image capture program according to a second exemplary embodiment.

Explanation follows regarding the operation of the imaging system 104 according to the present exemplary embodiment, with reference to FIG. 14. FIG. 14 is a flow chart illustrating a processing flow of a radiographic image capture program according to the second exemplary embodiment that is performed by the CPU 113 of the console 110 upon input of an instruction to execute the fluoroscopic image capture function through the operation panel 112. The program is stored in advance in a specific region of the ROM 114. In FIG. 14, steps in which similar processing is performed to that illustrated in FIG. 10 are allocated the same step numbers as in FIG. 10, and explanation thereof is omitted.

At step 324' in FIG. 14, still image data that has been received from the electronic cassette 40 during the still image capture routine program performed immediately prior and that has been stored is superimposed on image data (video image data) received from the electronic cassette 40 to generate synthesized image data.

In the imaging system 104, the video image data and the still image data are superimposed at step 324' by computing weighted average values of pixel data of corresponding pixels such that the ratio of the still image data to the video image data is gradually decreased each time the processing of step 322 to step 328 is repeated.

For example, in a case in which the processing target frame number set by the user is 5, the ratio is gradually decreased by, for example, 90%, 70%, 50%, 30%, 10% from the first time of the processing of step 324' to the fifth time of processing of step 324'.

The second exemplary embodiment achieves substantially the same effects as the first exemplary embodiment. Further, since frame images until the predetermined frame number (processing target frame number) is reached are displayed by being synthesized with the still image obtained by immediately-prior (last) image capture such that the ratio of the still image to the frame image gradually decreases, display images may even more smoothly transition to the images that are actually being captured.

Third Exemplary Embodiment

Next, detailed explanation is given regarding a third exemplary embodiment. Since configurations of a RIS 100, a radiographic imaging room, an electronic cassette 40 and an imaging system 104 according to the third exemplary embodiment are the same as those of the first exemplary embodiment, explanation thereof is omitted herein.

Figure 15:
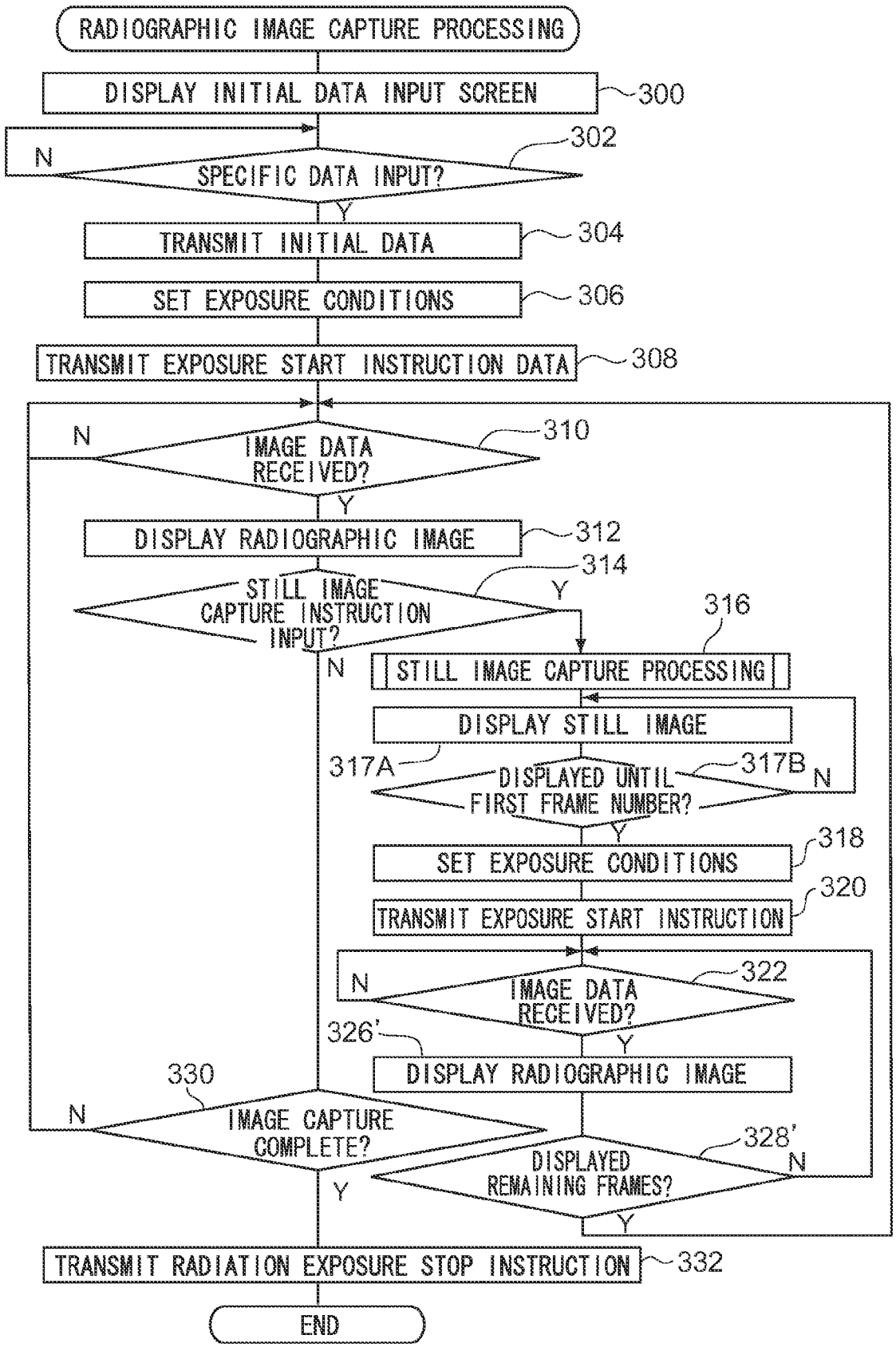
FIG. 15 is a flow chart illustrating a flow of a radiographic image capture program according to a third exemplary embodiment.

Explanation follows regarding the operation of the imaging system 104 according to the present exemplary embodiment, with reference to FIG. 15. FIG. 15 is a flow chart illustrating a processing flow of a radiographic image capture program according to the third exemplary embodiment that is performed by the CPU 113 of the console 110 upon input of an instruction to execute the fluoroscopic image capture function through the operation panel 112. This program is stored in advance in a specific region of the ROM 114. In FIG. 15, steps in which similar processing is performed to that illustrated in FIG. 10 are allocated the same step numbers as in FIG. 10, and explanation thereof is omitted.

At step 317A in FIG. 15, the display driver 117 is controlled such that the display 111 displays a radiographic image expressed by the still image data that has been received from the electronic cassette 40 and stored during the still image capture routine program performed immediately beforehand.

Then, at the next step 317B, determination is made as to whether or not the display 111 has displayed a predetermined first frame number of radiographic images, where the first frame number is a smaller number than the processing target frame number. If the determination is negative, processing returns to step 317A, and is the determination is affirmative, processing transitions to step 318. In the present exemplary embodiment, a number of half the processing target frame number is applied as the first frame number; however, embodiments are not limited thereto.

The processing of step 317A and step 317B is repeatedly executed such that the display rate of the still image at step 317A is the same as the display rate of each frame image of the video image in the radiographic image capture program (30 frames/second in the present exemplary embodiment). Further, during the repeated execution of the processing of step 317A to step 317B, control is effected such that the still image displayed on the display 111 by the processing of step 317A is gradually faded out.

Next, at step 326' the display driver 117 is controlled such that the display 111 displays a radiographic image expressed by the video image data received from the electronic cassette 40 during the prior processing of step 322.

Then, at step 328', determination is made as to whether or not the total of the number of frames of radiographic images displayed by the processing of step 322 to step 326' and the number of frames of the still image displayed by the processing of step 317A to step 317B has reached the processing target frame number contained in the initial data. If the determination is negative, processing returns to step 322, and if the determination is affirmative, processing returns to step 310.

During the repeated execution of the processing of step 322 to step 328', control is effected such that the image displayed on the display 111 by the processing of step 326' is gradually faded in.

The third exemplary embodiment achieves substantially the same effects as the first exemplary embodiment. Further, since the still image obtained by the immediately-prior (last) image capture is displayed until a frame image partway through the predetermined frame number (the processing target frame number) by gradually fading out the still image, and the remaining frame images are displayed by being gradually faded in, display images may even more smoothly transition to the images that are actually being captured.

Fourth Exemplary Embodiment

Next, detailed explanation is given regarding a fourth exemplary embodiment of the present invention. Since configurations of a RIS 100, a radiographic imaging room, an electronic cassette 40 and an imaging system 104 according to the fourth exemplary embodiment are the same as to those of the first exemplary embodiment, explanation thereof is omitted herein.

Figure 16:
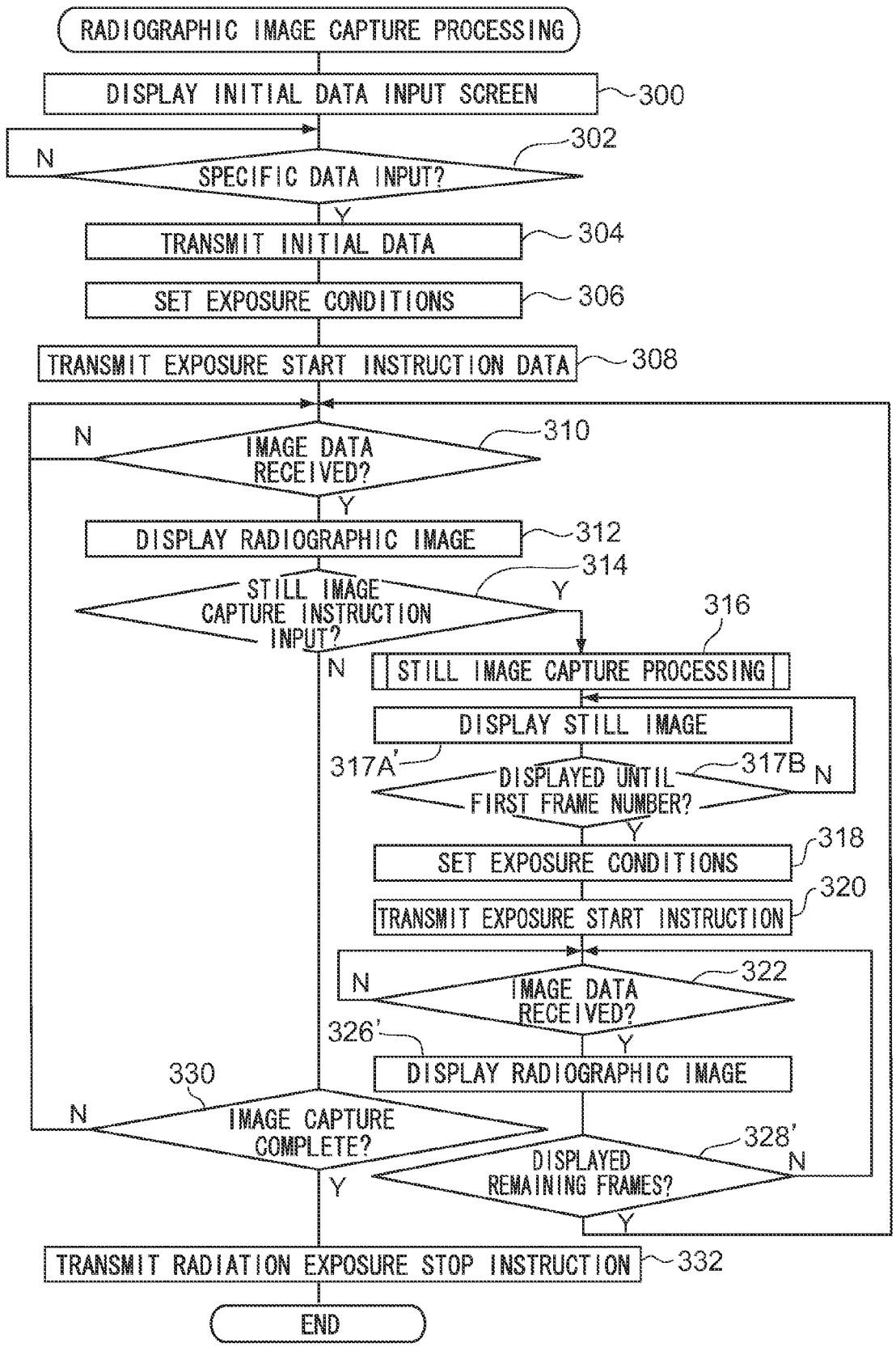
FIG. 16 is a flow chart illustrating a flow of a radiographic image capture program according to a fourth exemplary embodiment.

Explanation follows regarding operation of the imaging system 104 according to the present exemplary embodiment, with reference to FIG. 16. FIG. 16 is a flow chart illustrating a processing flow of a radiographic image capture program according to the fourth exemplary embodiment that is performed by the CPU 113 of the console 110 upon input of an instruction to execute the fluoroscopic image capture function through the operation panel 112. The program is stored in advance in a specific region of the ROM 114. In FIG. 16, steps in which similar processing is performed to that illustrated in FIG. 15 are allocated the same step numbers as in FIG. 15, and explanation thereof is omitted.

At step 317A' in FIG. 16, the display driver 117 is controlled such that the display 111 displays a radiographic image expressed by still image data that has been received from the electronic cassette 40 and stored during the still image capture routine program performed immediately beforehand.

Then, at the next step 317B, determination is made as to whether or not the display 111 has displayed a predetermined first frame number of radiographic images, where the first frame number is a smaller number than the processing target frame number. If the determination is negative, processing returns to step 317A', and if the determination is affirmative, processing transitions to step 318. In the present exemplary embodiment, a number of half the processing target frame number is applied as the first frame number; however, embodiments are not limited thereto.

The processing of step 317A' to step 317B is repeatedly executed such that the display rate of the still image at step 317A' is the same as the display rate of each frame image of the video image in the radiographic image capture program (30 frames/second in the present exemplary embodiment). Further, during the repeated execution of the processing of step 317A' to step 317B, control is effected such that the image displayed on the display 111 by the processing of step 317A is the same image (the image expressed by the still image data).

Then, at step 326", the display driver 117 is controlled such that the display 111 displays a radiographic image expressed by the video image data received from the electronic cassette 40 during the prior processing of step 322.

Then, at step 328', determination is made as to whether or not the total of the number of frames of radiographic images displayed by the processing of step 322 to step 326" and the number of frames of the still image displayed by the processing of step 317A' to step 317B has reached the processing target frame number contained in the initial data. If the determination is negative, processing returns to step 322, and if the determination is affirmative, processing returns to step 310.

The fourth exemplary embodiment achieves substantially the same effects as the first exemplary embodiment. Further, since the still image obtained by the immediately-prior (last) mage capture is displayed for frame images until a frame partway through the predetermined frame number (the pro-cessing target frame number), and the remaining frame images are displayed as they are, disruption in displayed images may be even more reliably prevented.

Fifth Exemplary Embodiment

Figure 19:
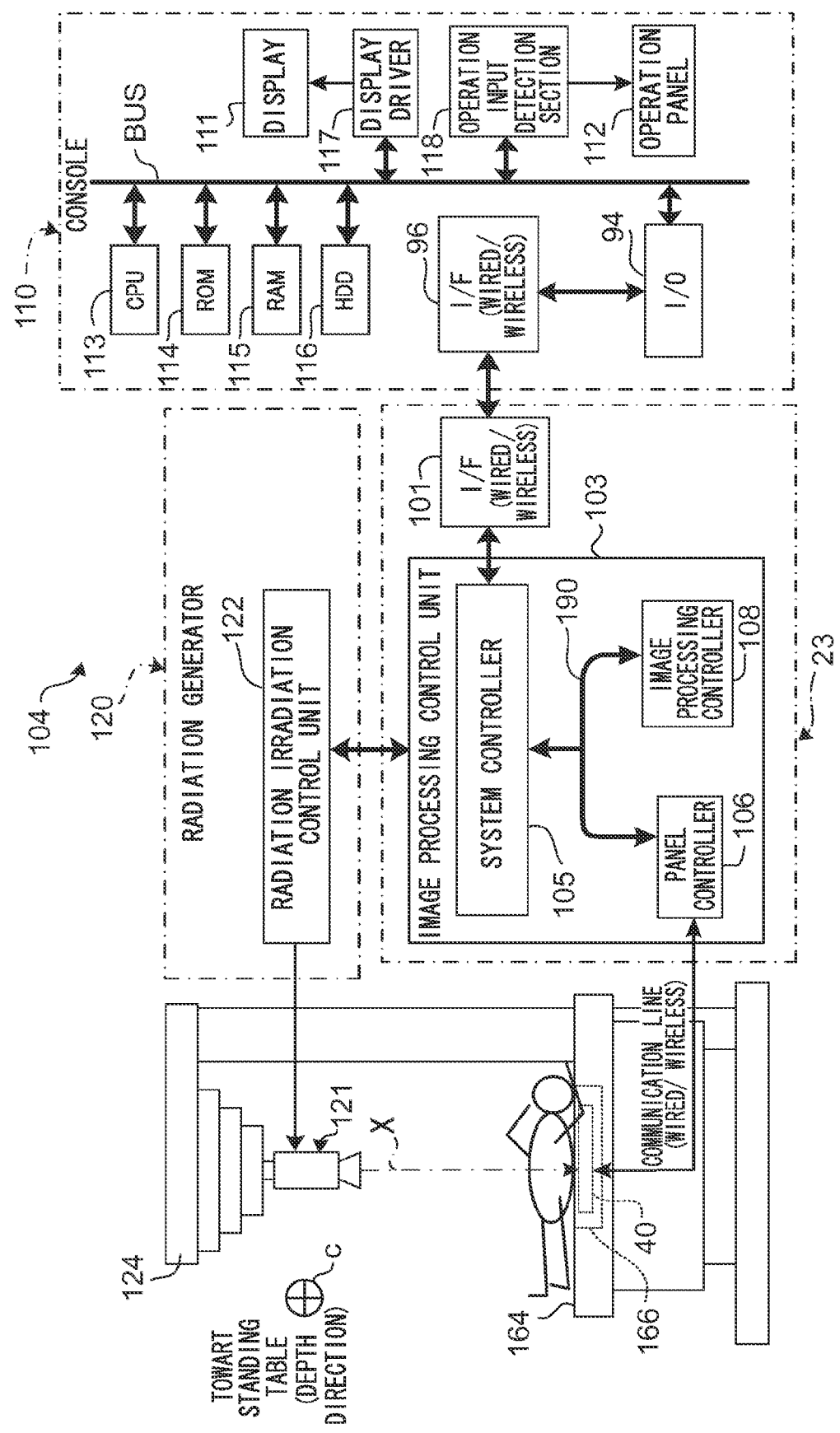
FIG. 19 is a control block diagram of an image capture system according to an exemplary embodiment.

FIG. 19 is a control block diagram of an imaging system 104 according to the present exemplary embodiment. The configuration of the imaging system 104 of the fifth exemplary embodiment is similar to that of the first exemplary embodiment except that it further includes an image processing device 23. Therefore, explanation is only given regarding points that differ to the first exemplary embodiment.

The console 110 uses wireless communication to perform transmission and reception of various data, such as irradiation conditions, described later, to and from the image processing device 23 and the radiation generator 120. The console 110 is provided with an I/F (such as a wireless communication section) 96 and an I/O 94 that perform transmission and reception of various data such as image data to and from the electronic cassette 40.

The image processing device 23 includes an I/F (such as a wireless communication section) 101 that performs transmission and reception of various data such as irradiation conditions to and from the console 110, and an image processing control unit 103 that controls the electronic cassette 40 and the radiation generator 120 based on the irradiation conditions. The radiation generator 120 further includes a radiation irradiation control unit (radiation source controller) 122 that controls radiation irradiation from the radiation irradiation source (radiation source) 121.

The image processing control unit 103 includes a system controller 105, a panel controller 106, and an image processing controller 108, which mutually communicate data through a bus 190. The panel controller 106 receives data through a wireless or wired connection from the electronic cassette 40, and the data is subjected to image processing by the image processing controller 108.

The system controller 105 receives, for example, tube voltage and tube current data as the irradiation conditions from the console 110, and effects control the radiation irradiation source 121 of the radiation irradiation control unit 122 to perform irradiation of the radiation X based on the received irradiation conditions.

Figure 20:
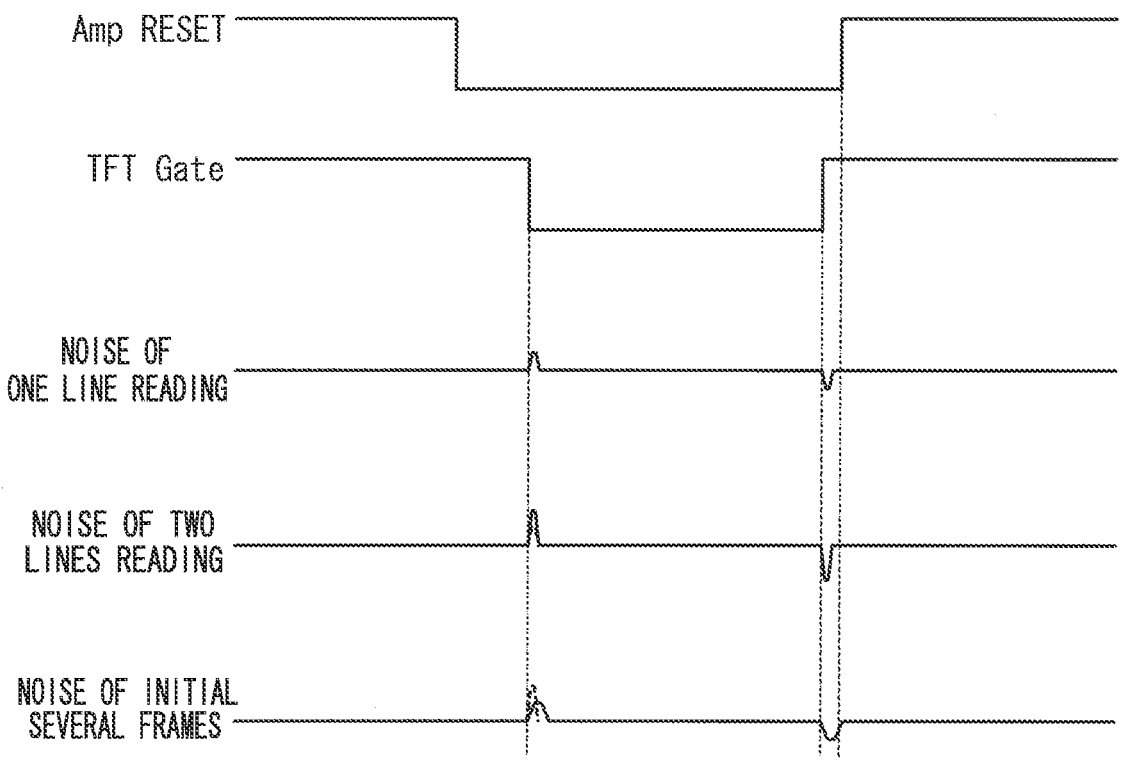
FIG. 20 is a diagram for explaining feed-through noise due to switching thin film transistors ON or OFF.

In the radiation detector 20, as illustrated in FIG. 20, it is known that noise (also referred to below as feed-through noise) occurs when the thin-film transistors 10 are switched ON and OFF in order to read charges accumulated in the capacitors 9.

However, the noise when the thin-film transistors 10 are switched ON is noise in the opposite direction (with reverse polarity) to the noise when the thin-film transistors 10 are switched OFF. Accordingly, the feed-through noise is canceled out by integration processing performed by the charge amplifiers 82 during the reading duration in which the reset switches 79 of the charge amplifiers 82 are switched OFF.

Further, during video image capture, the read rate is increased by reading the charges using a binning read method in which plural lines are read at the same time although the resolution decreases. As illustrated in the plot of two-line reading in FIG. 20, since plural lines are read at the same time in a binning read method, the feed-through noise described above increases by the amount of the plural lines (since two lines are read in FIG. 20, the feed-through noise is substantially doubled).

As described above, there is normally no problem since the noise when the thin-film transistors 10 are switched ON and switched OFF is cancelled out. However, in cases in which there is a change in image capture conditions, such as immediately after switching from a sequential read method to a binning read method or immediately after switching to increase the number of lines that are binned, a deterioration in image quality that could be attributable to noise may occur over several frames.

Figure 21:
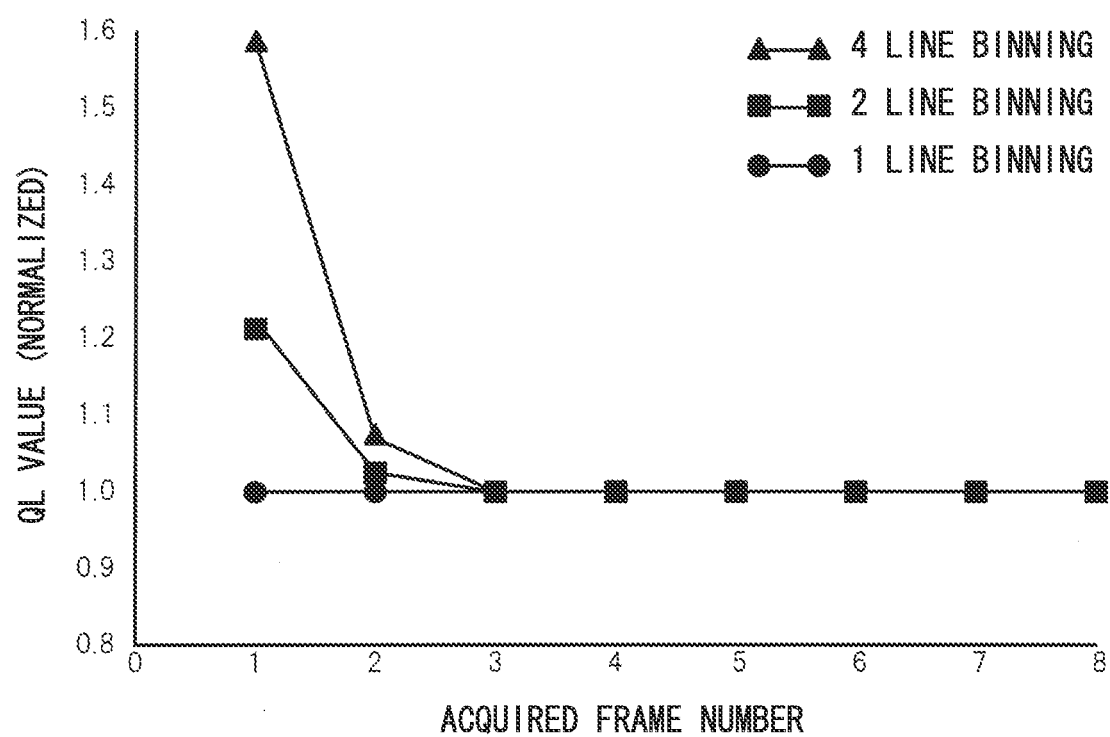
FIG. 21 is a diagram illustrating changes in QL values for each acquired frame.

Specifically, as illustrated in FIG. 21, QL values are unstable between the first frame and the third frame, and are stable after the third frame. Note that a QL value is a value corresponding to film density in radiographic images obtained by radiation irradiation, and may be a gradation signal, or may be a signal obtained by subjecting a gradation signal to specific processing. The QL values illustrated in FIG. 21 are normalized values based on a specific value.

Analysis of factors causing instability of QL values has revealed that after switching the read method or the binning number, the absolute value of the teed-through noise does not increase, but, as illustrated in the bottom line of FIG. 20, the length of time for which noise occurs increases and overlaps with the amplifier reset timing. Therefore, the noise due to switching OFF the thin-film transistors 10 may not be integrated by the charge amplifiers 82, and may not be cancelled out.

Therefore, in the present exemplary embodiment, in order to improve the visual interpretability quality of the images that become unstable when the binning number is switched to a higher number, different density ranges are selected as image data between a predetermined number of frames after switching and the subsequent frames.

Namely, after performing histogram analysis on each frame, for example, a range at the higher density side illustrated in (1) of FIG. 22 is used as image data from the first frame until the predetermined frame after a binning number switch, and a density range at the a lower density side than that illustrated in (1) of FIG. 22 is used as image data for subsequent frames, as illustrated in (2) of FIG. 22. Since the image data other than that within the selected density range is discarded, noise during display is reduced and visual interpretability qualities may be improved even when the image quality becomes unstable.

A method for selecting different density ranges as image data for the predetermined number of frames after switching binning number and for subsequent frames may include selecting different ranges for ranges on which dynamic range compression is performed.

Figure 23A:
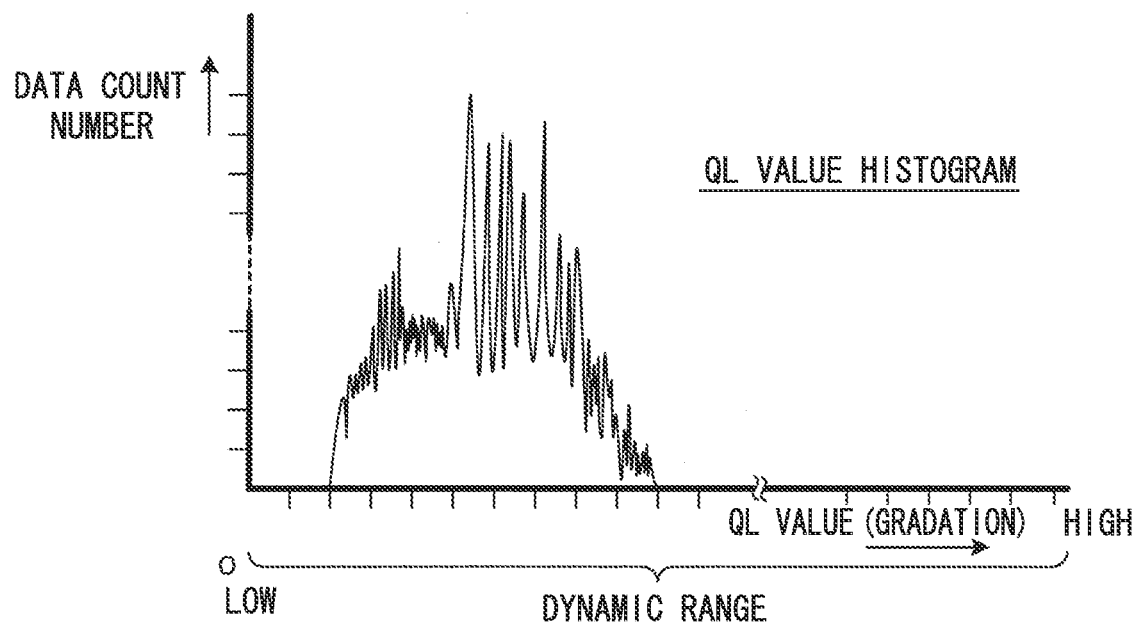
FIG. 23A is a graph illustrating a dynamic range after histogram analysis is performed on QL values of each frame.
Figure 23B:
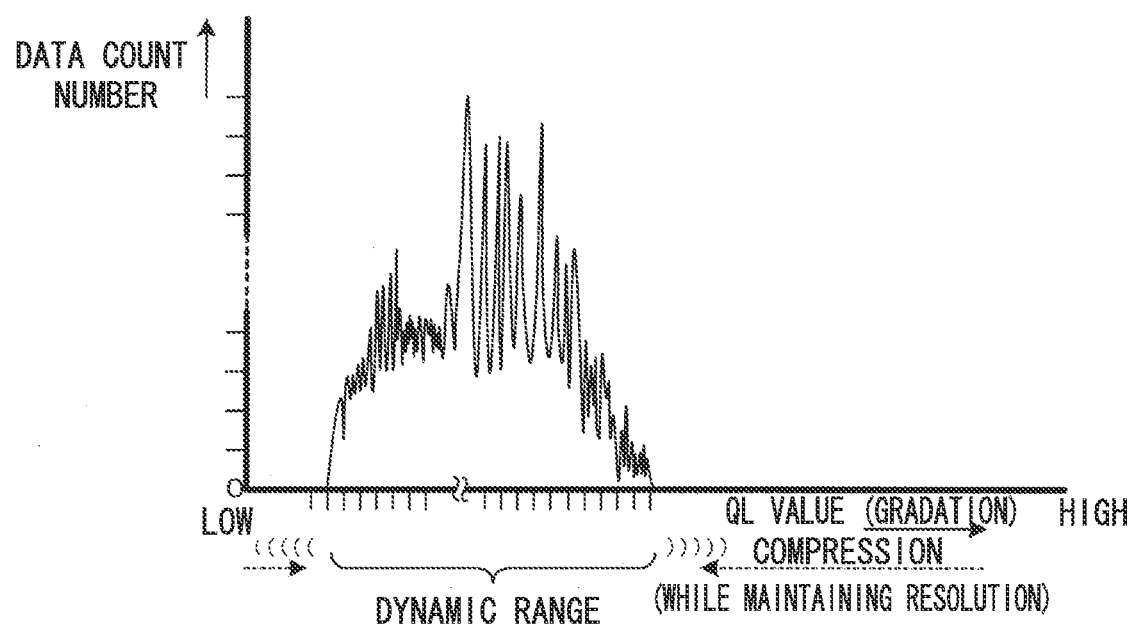
FIG. 23B is a diagram for explaining dynamic range compression of QL values.

For example, as illustrated in FIG. 23A and FIG. 23B, histogram analysis is performed on each frame and the dynamic range is compressed to a specific range in which data count values distribute. In this case, similarly to as described above, from the first frame after binning number switching until the predetermined frame, dynamic range compression is performed to a higher density range than that for subsequent frames, and the dynamic range compression range for the subsequent frames is shifted towards the lower density range. Thereby, visual interpretability of images may be improved even when image quality becomes unstable.

Explanation follows regarding a configuration for performing the above processing during binning number switching. FIG. 24 is a block diagram illustrating a schematic configuration downstream of the signal processor 54. In the present exemplary embodiment, the configuration downstream of the signal processor 54 onwards may be provided in the radiation detector 20, may be provided in the image processing control unit 103 side, or may be provided in the console 110.

As illustrated in FIG. 24, digital gradation signals output from the signal processor 54 (A/D converter 89) are temporarily stored in a frame memory 1112.

After gradation signals for one frame have been stored in the frame memory 1112, the gradation signals are output to a still image generation section 1114 and a still image is generated.

In the still image generation section 1114, the gradation signals for one frame are used to generate image data of a still image, and the image date is output to a video image compilation section 1118. In this processing, histogram analysis is performed by a gradation signal analysis section 1116, and different processings are performed for the first frame at the time of binning number switching until the predetermined frame, and for the subsequent frames.

Namely, the gradation signal analysis section 1116 performs histogram analysis on the gradation signals and, as described above and illustrated in (1) and (2) of FIG. 22, only image data at a higher density range than that employed for subsequent frames is employed for the first frame at the time of binning number switching until the predetermined frame, and only image data at a lower density range than that employed for the predetermined frame is employed for the subsequent frames. Alternatively, for the first frame at the time of binning number switching until the predetermined frame, dynamic range compression is performed on a higher density range than that for the subsequent frames, and for the subsequent frames, a range subject to dynamic range compression is shifted to a lower density range.

In the video image compilation section 1118, the still images generated by the still image generation section 1114 are combined as frame images to generate a video image, and the generated video image data is stored in a memory 1120. Thus, under control of the display driver 117, the video image can be displayed on the display 111 based on the video image data stored in the memory 1120.

Next, explanation follows regarding the operation of the present exemplary embodiment using the flow charts of FIG. 25 to FIG. 28.

FIG. 25 is a flow chart illustrating a radiographic image capture preparation control routine.

At step 200, determination is made as to whether or not there has been an image capture instruction. If the determination is negative, the routine is ended, and if the determination is affirmative, processing transitions to step 202.

At step 202, the initial data input screen is displayed on the display 111 and processing transitions to step 204. Namely, the display driver 117 is controlled to display the predetermined initial data input screen on the display 111.

At step 204, determination is made as to whether or not specific data has been input, and the processing stands by until the determination is affirmative and processing transitions to step 206. The initial data input screen displays messages to prompt input of the name of a subject for radiographic image capture, imaging target site, posture during imaging, and radiation X irradiation conditions during imaging (in the present exemplary embodiment, tube voltage and tube current during radiation X irradiation), and displays input fields for such data.

After the initial data input screen has been displayed by the display 111, the user may input the name of the subject for image capture, the imaging target site, the posture for image capture and the irradiation conditions to each corresponding input field using the operation panel 112.

The user may enter the radiographic imaging room 180 together with the subject, and if the posture is the recumbent position, after placing the electronic cassette 40 on the corresponding holder 166 of the recumbent position table 164 and positioning the radiation irradiation source 121 in a corresponding position, the user may position the subject in a specific imaging position. If a radiographic image is to be captured for an imaging target site such as an arm region or leg region without retaining the electronic cassette 40 with a holder, the user may position the subject, the electronic cassette 40 and the radiation irradiation source 121 in a state in which image capture is possible.

The user may then exit the radiographic imaging room 180, and may designate the COMPLETE button displayed, for example, in the vicinity of the lower edge of the initial data input screen via the operation panel 112. After the user has designated the COMPLETE button, affirmative determination is made at step 204 and processing transitions to step 206. Although in the flow chart of FIG. 25, step 204 is configured as an infinite loop, configuration may be made such that the processing is forcibly terminated by operation of a CANCEL button provided to the operation panel 112.

At step 206, the data input to the initial data input screen (referred to below as "initial data") is transmitted to the electronic cassette 40 using the wireless communication section 96, and thereafter processing transitions to the next step 208, at which the irradiation conditions contained in the initial data are transmitted to the radiation generator 120 using the wireless communication section 96 and are set in the radiation generator 120. In response, the radiation irradiation control unit 122 of the radiation generator 120 prepares for irradiation with the received irradiation conditions.

At the next step 210, instruction to activate ABC control is issued, and then processing transitions to step 212, at which instruction data instructing initiation of radiation irradiation is transmitted to the radiation generator 120 using the wireless communication section 96. Then, the current routine is ended.

Figure 26:
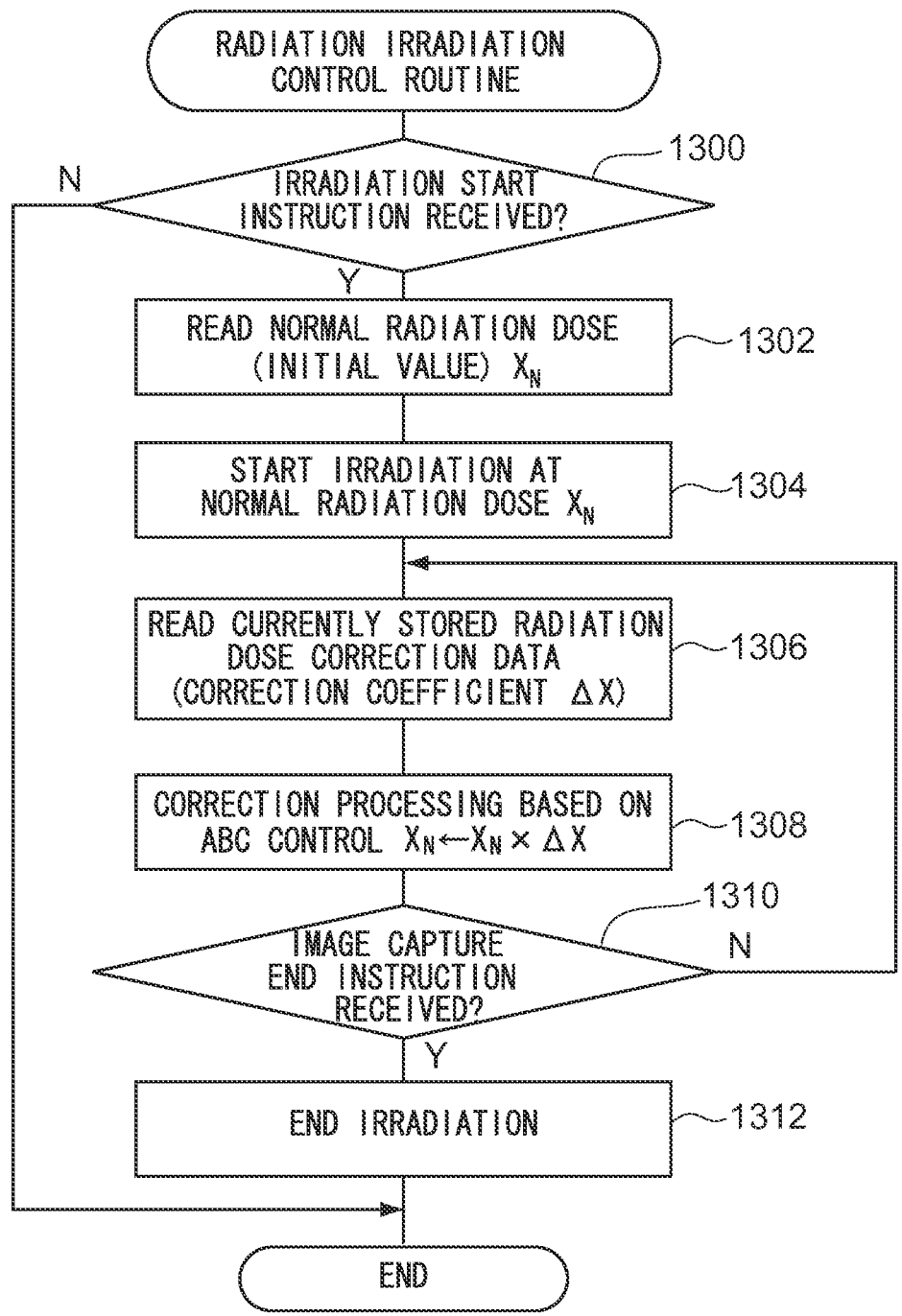
FIG. 26 is a flow chart illustrating a radiation irradiation control routine according to an exemplary embodiment.

Next, explanation is given regarding a flow of radiation irradiation control, with reference to the flow chart of FIG. 26. FIG. 26 is a flow chart illustrating a radiation irradiation control routine.

At step 1300, determination is made as to whether or not there has been an instruction to initiate irradiation. If the determination is negative, the current routine is ended, and if determination is affirmative, processing transitions to step 1302.

At step 1302, a normal radiation dose (initial value) $X_N$ is read, and processing transitions to step 1304.

At step 1304, irradiation is started at the normal radiation dose, and processing transitions to step 1306. Namely, irradiation of radiation from the radiation irradiation source 121 is started by applying the tube voltage and tube current corresponding to the irradiation conditions received from the console 110 to the radiation generator 120. The irradiated radiation X from the radiation irradiation source 121 reaches the electronic cassette 40 after passing through the subject.

At step 1306, currently stored radiation dose correction data is read and processing transitions to step 1308. This radiation dose correction data is generated by the ABC control, and is stored as a correction coefficient $\Delta X$.

At the next step 1308, correction processing based on the ABC control is executed and processing transitions to step 1310. Namely, an average value of QL values is computed for an image region of interest based on the gradation signals (QL values) obtained from the electronic cassette 40. The average value of the QL values is compared with a predetermined threshold value, and the radiation dose is feedback controlled so that the average value of the QL values converges on the threshold value.

At step 1310, determination is made as to whether or not there has been an instruction to terminate the image capture. If the determination is affirmative, processing transitions to step 1312, and if the determination is negative, processing returns to step 1306 and the above processing is repeated.

At step 1312, irradiation is terminated, and radiographic image capture control is ended.

Figure 27:
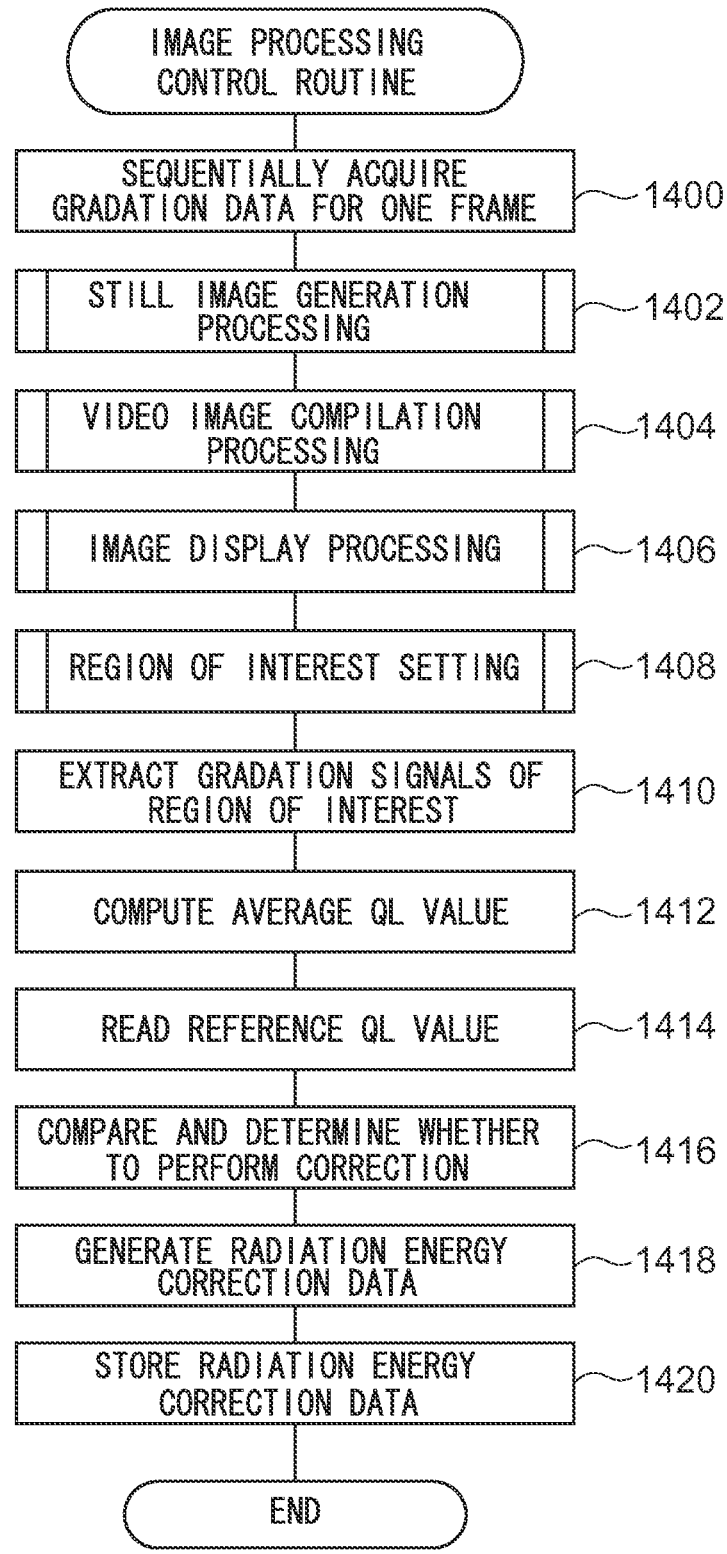
FIG. 27 is a flow chart illustrating an image processing control routine according to an exemplary embodiment.

Next, explanation follows regarding a flow of image processing control with reference to the flow chart of FIG. 27. FIG. 27 is a flow chart illustrating an image processing control routine. For the following processing, explanation is given of processing in a case in which the signal processor 54 and the configuration downstream thereof (including the frame memory 1112, the still image generation section 1114, the gradation signal analysis section 1116, the video image compilation section 1118, and the memory 1120) is provided in the image processing control unit 103.

After the radiographic image capture control described above has been performed, at step 1400, gradation data for one frame is sequentially acquired and processing transitions to step 1402. Namely, the gradation signals generated by the TFT substrate 30 of the electronic cassette 40 are sequentially input to the image processing control unit 103 under control of the panel controller 106. Prior to being input to the image processing control unit 103, the gradation signals are sequentially input to by the cassette controller 58, and the gradation signals input to the cassette controller 58 are sequentially output to the image processing control unit 103 under control of the panel controller 106.

At step 1402, still image generation processing is performed and processing transitions to step 1404. Detailed explanation regarding the still image generation processing is given later.

At step 1404, video image compilation processing is performed and processing transitions to step 1406. The video image compilation processing compiles a video image by combining the still images generated at step 1402 frame by frame.

At step 1406, image display processing is performed and processing transitions to step 1408. In the image display processing, the video image generated by the video image compilation processing is output to the display driver 117, and the display driver 117 performs display on the display 111.

At step 1408, region-of-interest setting is performed and processing transitions to step 1410. The region of interest is set by, for example, performing pattern matching or detecting regions with a large movement amount. Or, the region of interest may be set by operation of a user.

At step 1410, gradation signals of the region of interest are extracted and processing transitions to step 1412

At step 1412, an average QL value of the gradation signals of the region of interest is computed and processing transitions to step 1414, where a pre-stored reference QL value is read. Then, processing transitions to step 1416.

At step 1416, the computed average QL value and the read reference QL value are compared, determination is made as to whether or not to perform correction, and processing transitions to step 1418. The determination as to whether or not to perform correction may be, for example, an ON/OFF determination, in which correction is performed with a predetermined correction amount if a difference in the comparison results is a specific difference or greater, and correction is not performed if the difference is smaller than the specific difference. Or, the determination may be made by a solution of a predetermined equation (for example, an equation based on PID control) based on the difference.

At step 1418, radiation dose correction data ΔX is generated based on the result of the comparison and the determination as to whether or not to perform correction in step 1416, and processing transitions to step 1420.

At step 1420, the generated radiation dose correction data ΔX is stored, and the image processing control is ended.

Figure 28:
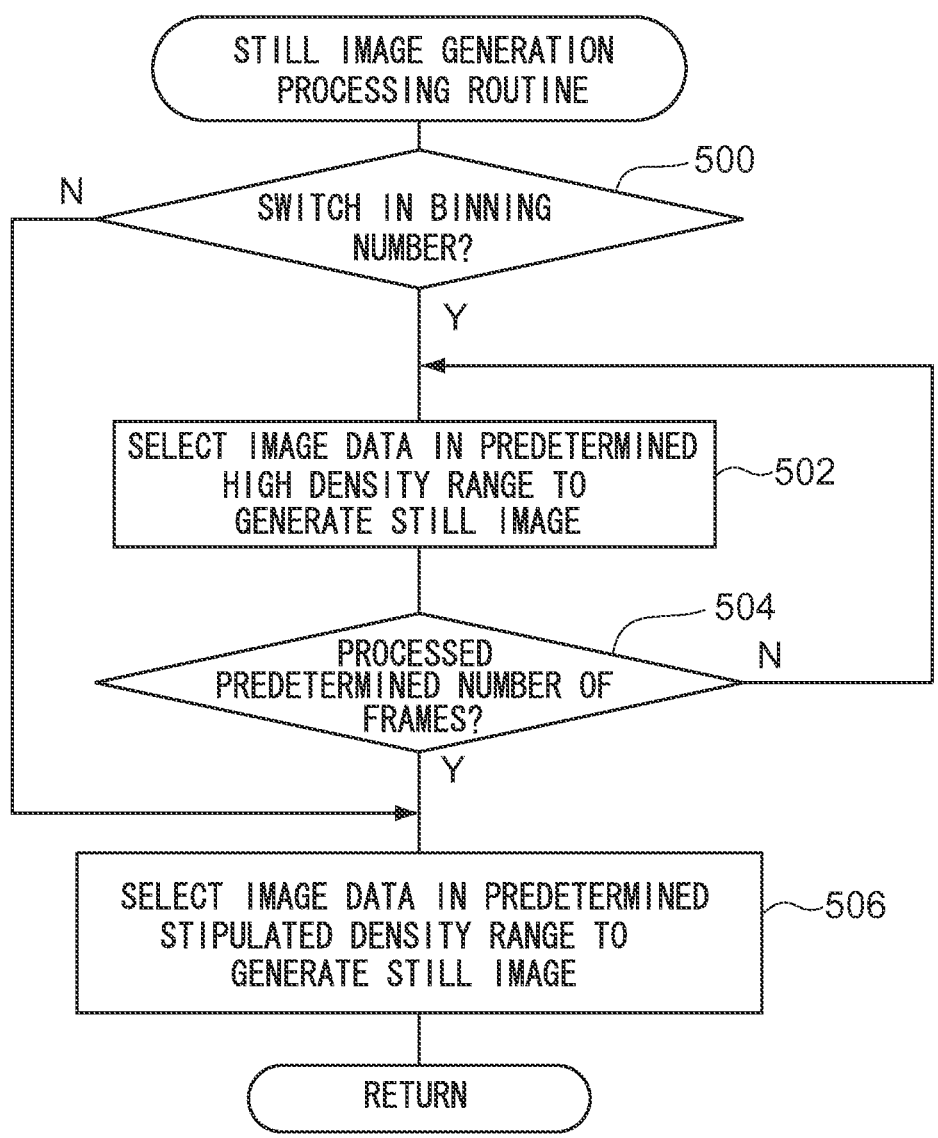
FIG. 28 is a flow chart illustrating a still image generation processing routine according to an exemplary embodiment.

Next, explanation follows regarding a flow of the still image generation processing mentioned above, with reference to the flow chart of FIG. 28. FIG. 28 is a flow chart illustrating a still image generation processing routine. In this case, FIG. 28 describes processing performed by the still image generation section 1114 and the gradation signal analysis section 1116 prior to video image compilation at the video image compilation section 1118. However, the processing of FIG. 28 may be performed at the same time as video image capture, or may be performed when the gradation signals obtained through image capture are temporarily stored in, for example, the memory 1120 and displayed after the image capture.

At step 500, determination is made as to whether or not the binning number has been switched. Here, it is determined as to whether or not the binning number has been increased. If the determination is affirmative, processing transitions to step 502, and if the determination is negative, processing transitions to step 506. In cases in which the binning number has been during the transition from still image to video image, this determination may be made based on whether or not a switch from still image to video image has been instructed using the operation panel 112, based on whether or not the read method has been switched, or based on whether or not an instruction to increase the binning number has been performed using the operation panel 112. In cases in which the binning number has changed depending on the frame rate, determination may be made as to whether or not the frame rate has been changed.

At step 502, image data within a predetermined high density range is selected to generate a still image and processing transitions to step 504. For example, only image data within the predetermined high density range may be selected, or image data within the predetermined high density range may be selected by compressing the dynamic range into the predetermined high density range. By employing as image data only gradation signals in a density range in the histogram where most of density distribution lies, image quality may be improved compared to a case in which gradation signals over the entire density range are employed as image data, and visual interpretability may also be improved.

At step 504, determination is made as to whether or not the predetermined frame has been reached, and if the determination is negative, processing returns to step 502 and the above processing is repeated. If the determination is affirmative, processing transitions to step 506.

At step 506, the image data of a predetermined density range is selected to generate a still image and then the still image generation processing returns to the invoker routine. That is, the density range is shifted toward a lower density range and only image data of the predetermined stipulated density range is selected as image data, or the dynamic range is compressed into the predetermined stipulated density range. Namely, image data is selected from the predetermined stipulated density range after the image quality has stabilized after binning number switching.

In this way, when there is a change in image capture conditions, such as immediately after switching to increase the number of lines that are binned, from a frame at this time until the predetermined frame, image data is selected from the predetermined high density range, and after stabilization, the density range for selecting image data is shifted toward the lower density range and image data is selected from the predetermined stipulated range. Thereby, visual interpretability may be improved even when image quality is unstable after switching of image capture conditions.

Figure 29:
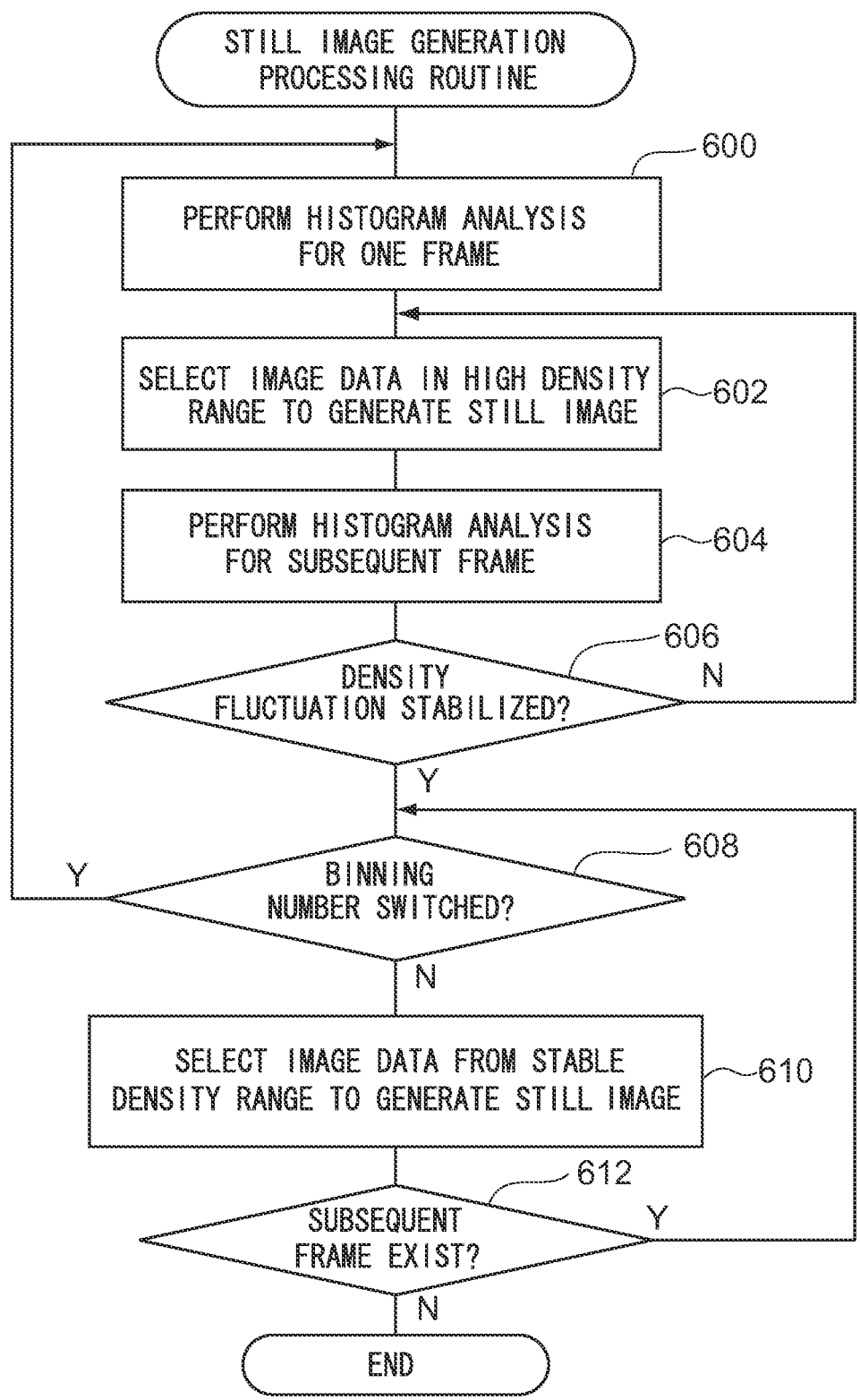
FIG. 29 is a flow chart illustrating a modified example of a still image generation processing routine according to an exemplary embodiment.

In the exemplary embodiment described above, in order to improve visual interpretability when image quality is unstable after switching to increase the binning number, the predetermined density range is selected when selecting image data from different density ranges between the predetermined number of frames after switching and the subsequent frames. However, the density range may be selected according to the actual density distribution. For example, it is possible to select image data according to the actual density distribution by temporarily storing in the memory 1120 all of the gradation signals obtained through image capture, and performing still image generation processing with post-processing. In this case, still image generation processing is performed as illustrated in the flow chart illustrated in FIG. 29. FIG. 29 is a flow chart illustrating a modified example of a still image generation processing routine.

Firstly, at step 600, histogram analysis is performed for one frame, and processing transitions to step 602. A histogram is generated for the occurrence frequency of the gradation signals as illustrated in (1) and (2) of FIG. 22, for example.

At step 602, image data of a high density range is selected to generate a still image, and processing transitions to step 604. For example, from the start of video frames, only image data of a higher density range than the density distribution of frames subsequent to the predetermined frame is selected to generate the still image, or the range of the dynamic range compression is set at the high density range to generate the still image.

At step 604, histogram analysis is performed for the next frame and processing transitions to step 606.

At step 606, determination is made as to whether or not density fluctuations have stabilized. This determination is made by determining whether or not fluctuations in the density range have stabilized and the range of the density distribution of the current histogram has shifted toward the lower density range than the density range that has been selected as image data. If the determination is negative, processing returns to step 602 and the processing described above is repeated, and if the determination is affirmative, processing transitions to step 608.

At step 608, determination is made as to whether or not the binning number has been switched, and if the determination is affirmative, processing returns to step 600 and the above processing is repeated. If the determination is negative, processing transitions to step 610. For this determination, when storing the gradation signals in the memory 1120, information on an instruction to switch the binning number or to switch from a still image to a video image may also be stored.

At step 610, since the density is stable and the binning number has not been switched, image data is selected from the stable density range to generate a still image and processing transitions to step 612. Specifically, only image data in the stable density range is selected, or dynamic range compression is performed to this stable density range.

At step 612, determination is made as to whether or not there is a next frame, and if the determination is affirmative, processing returns to step 608 and the above processing is repeated. If the determination is negative the processing routine is ended.

By processing in this way, similarly to the exemplary embodiments described above, the visual interpretability may be improved even when image quality is unstable after image capture conditions are switched.

In this modified example, since the gradation signals obtained through image capture are temporarily saved and the above processing is performed as post-processing, image data within the higher density range can be selected until the image quality stabilizes, and after the image quality stabilizes, image date can be selected from a normal density range (stable density range). Although visual interpretability may be improved to a greater extent in the present exemplary embodiment than in the preceding exemplary embodiment, since the processing is performed as post-processing, it is impossible to check the video image at the same time as image capture, as in the preceding exemplary embodiment. However, image quality may be improved further than in the preceding exemplary embodiment.

In the exemplary embodiments described above, gradation signals in the predetermined high density range are selected after there is a change in image capture conditions, such as immediately after switching to increase the binning number, and gradation signals in the predetermined stipulated range are selected after the predetermined frames by shifting the range toward the lower density side. However, image data may be selected from a density range by gradually shifting the density range from the predetermined high density side to the stipulated range. Thereby, a sudden change in image density during display may be prevented.

Although explanation has been given above regarding exemplary embodiments of the present invention, the technical scope of the present invention is not limited to the exemplary embodiments described above. Various modifications and improvements may be made to the above exemplary embodiments within a range not departing from the spirit of the invention, and such changes or improvements also fall within the technical scope of the present invention.

The above exemplary embodiments do not limit the invention according to the claims, and not all of the combinations of features explained in the exemplary embodiments are essential for the solution of the invention. The exemplary embodiments described above include various stages of the invention, and various implementations of the invention may be arrived at through appropriate combination of the plural configuration elements disclosed herein. The invention may be implemented by a configuration in which certain configuration elements have been omitted from the overall configuration disclosed in the exemplary embodiments provided that the advantageous effect can be obtained.

For example, in the first exemplary embodiment to the fourth exemplary embodiment, explanation has been given of cases in which the combined display function is realized by processing of the console 110. However, embodiments are not limited thereto and, for example, the combined display function may be realized by processing of the electronic cassette 40. In such case, after the binning number has been increased in the electronic cassette 40, the CPU 58A of the cassette controller 58 may perform processing to generate image data expressing a combined radiographic image of a still image and video image, similarly to the respective exemplary embodiments described above.

In the first exemplary embodiment to the fourth exemplary embodiment, explanation has been given in which the binning number for performing binning is set at two. However, embodiments are not limited thereto, and, for example, the binning number may be set at three or more. In such cases, similarly to the respective exemplary embodiments described above, processing of displaying a radiographic image that is a combination a still image and video image is executed if the state is transitioned from not performing binning to performing binning, or if the binning number is increased in a state in which binning is performed.

In each of the exemplary embodiments described above, explanation has been given in which an indirect conversion method device is employed for the radiographic image capture device. However, embodiments are not limited thereto, and a direct conversion method device may be employed.

In the first exemplary embodiment to the fourth exemplary embodiment, explanation has been given in which the processing target frame number is set by an user. However, embodiments are not limited thereto. For the processing target frame number, for example, a statistical number of frames at which disruption to the display image is not perceivable, or is not distracting even if it is perceivable, may be derived in advance by sensory testing, and this number may be employed as a fixed processing target frame number.

In each of the exemplary embodiments described above, explanation has been given in which the electronic cassette 40 has a built-in battery, and the battery is charged through the cradle 130 when not in use. However, embodiments are not limited thereto. For example, the electronic cassette 40 may be provided with two batteries including a replaceable main battery and a back-up battery built into the housing, and the electronic cassette 40 may operate with power supplied from the back-up battery during replacement of the main battery, thereby enabling battery replacement during operation, i.e., a "hot swap" (battery hot plug). Since the power source of the electronic cassette does not need to be turned off during battery replacement, restart of the electronic cassette is unnecessary and quick battery replacement is possible. Such a configuration is beneficial in cases of performing repeated image capture such as in the exemplary embodiments described above.

In each of the exemplary embodiments described above, explanation has been given in which the sensor portions 13 are configured including an organic photoelectric conversion material that generates charges on receipt of light that has been generated by the scintillator 8. However, embodiments are not limited thereto, and the sensor portions 13 without including an organic photoelectric conversion material may be applied.

In each of the exemplary embodiments described above, the case 42 in which the cassette controller 58 and the power source section 70 are housed and the radiation detector 20 are disposed inside the casing 41 of the electronic cassette 40 so as to not overlap with each other. However, embodiments are not limited thereto and, for example, the radiation detector 20 and the cassette controller 58 and/or the power source section 70 may be disposed so as to overlap with each other.

In each of the exemplary embodiments described above, explanation has been given in which wireless communication is performed between the electronic cassette 40 and the console 110, and between the radiation generator 120 and the console 110. However, embodiments are not limited thereto and, for example, at least one of these communications may be performed by wired communication.

In each of the exemplary embodiments described above, explanation has been given wherein X-rays are employed for the radiation; however, embodiments are not limited thereto, and other types of radiation such as gamma ($\gamma$) rays may be employed.

The configuration of the RIS 100 (see FIG. 1), the radiographic imaging room (see FIG. 2), the electronic cassette 40 (see FIG. 3 to FIG. 7, FIG. 9, FIG. 17, FIG. 18), and the imaging system 104 (see FIG. 8, FIG. 19) explained in each of the exemplary embodiments described above are merely examples thereof, and portions that are not required may be omitted, new portions may be added, and connection states and the like may be modified within a range not departing from the spirit of the present invention.

The configurations of the initial data in each of the exemplary embodiments described above are also merely examples thereof, and data that is not required may be omitted and new data may be added within a range not departing from the spirit of the present invention.

The processing flows of each of the programs in each of the exemplary embodiments (see FIG. 10, FIG. 12, FIG. 14 to FIG. 16, FIG. 25 to FIG. 29) are also merely examples thereof, and steps that are not required may be omitted, new steps may be added, and the sequence of processing may be varied within a range not departing from the spirit of the present invention.

The configurations of the initial data input screens (see FIG. 11) in each of the exemplary embodiments described above are also merely examples thereof, and data that is not required may be omitted and new data may be added within a range not departing from the spirit of the present invention.

The processing illustrated in each of the flow charts for each of the exemplary embodiments described above may be distributed as a program stored on various non-transitory computer-readable storage media.

What is claimed is:

1. A radiographic video processing device, comprising:
an acquisition section that acquires gradation signals expressing charges from a radiation detector in which a plurality of pixels are disposed in a matrix formation, each pixel including a sensor portion that generates charges according to irradiated radiation and a switching element that reads charges generated at the sensor portion; and
a control section that, if capture of a video image formed from a plurality of frames is being performed with the radiation detector by switching the switching elements ON and OFF to read the charges and converting the read charges to voltage, and a number of the pixels, from which charges are combined and read by the switching elements included in adjacent pixels, has been increased, effects control such that, from a frame at a time of the increase up until a predetermined frame, the gradation signals distributed in a higher density range than that for frames subsequent to the predetermined frame are used as image data.

2. The radiographic video processing device of claim 1, wherein if the number of pixels has been increased, the control section effects control such that, from the frame at the time of the increase up until the predetermined frame, dynamic range compression is performed with respect to the gradation signals distributed in the higher density range than that for the frames subsequent to the predetermined frame.

3. The radiographic video processing device of claim 1, wherein the control section further effects control such that, for the frames subsequent to the predetermined frame, a range of the gradation signals used as image data is gradually shifted to a range lower than the higher density range.

4. The radiographic video processing device of claim 1, wherein the predetermined frame is a frame at a time immediately before density fluctuations in the gradation signals, due to switching of the number of pixels, stabilize.

5. The radiographic video processing device of claim 1, wherein detection of whether or not the number of pixels has been increased is detection of satisfaction of a condition of:

a transition from a state in which still image capture is performed by the radiation detector to a state in which video image capture is performed by the radiation detector;
a frame rate of the video image capture has been increased while performing video image capture by the radiation detector; or
a transition from a sequential scanning method in which charges generated in the pixels are read sequentially to a skip scanning method in which charges generated in each of the pixels are read from every other line, per every one line of odd numbered rows or even numbered rows.

6. A radiographic video image capture device, comprising:
a radiation detector in which a plurality of pixels are disposed in a matrix formation, each pixel including a sensor portion that generates charges according to irradiated radiation and a switching element that reads charges generated at the sensor portion; and
the radiographic video processing device of claim 1.

7. A radiographic video image capture system, comprising:
the radiographic video image capture device of claim 6; and
a radiation irradiation section that irradiates radiation through a subject and onto the radiation detector.

8. A radiographic video processing method, comprising:
detecting whether or not a video image formed from a plurality of frames is being captured using a radiation detector in which a plurality of pixels are disposed in a matrix formation, each pixel including a sensor portion that generates charges according to irradiated radiation and a switching element that reads charges generated at the sensor portion, by switching the switching elements ON and OFF to read the charges and converting the read charges to voltage, and detecting whether or not a number of the pixels, from which charges are combined and read by the switching elements included in adjacent pixels, has been increased; and
controlling such that, if it is detected that the number of pixels has been increased, the gradation signals expressing the charges distributed in a higher density range than that for frames subsequent to a predetermined frame are used as image data, from a frame at a time of the increase up until the predetermined frame.

9. The radiographic video processing method of claim 8, wherein if the number of pixels has been increased, the controlling includes performing dynamic range compression with respect to the gradation signals distributed in the higher density range than that for frames subsequent to the predetermined frame, from the frame at the time of the increase up until the predetermined frame.

10. The radiographic video processing method of claim 8, wherein the controlling further effects control such that, for the frames subsequent to the predetermined frame, a range of the gradation signals used as image data is gradually shifted to a range lower than the higher density range.

11. The radiographic video processing method of claim 8, wherein the predetermined frame is a frame at a time immediately before density fluctuations in the gradation signals, due to switching of the number of pixels, stabilize.

12. The radiographic video processing method of claim 8, wherein the detecting whether or not the number of pixels has been increased includes detecting satisfaction of a condition of:

a transition from a state in which still image capture is performed by the radiation detector to a state in which video image capture is performed by the radiation detector; or a frame rate of the video image capture has been increased while performing video image capture by the radiation detector; or a transition from a sequential scanning method in which charges generated in the pixels are read sequentially to a skip scanning method in which charges generated in each of the pixels are read from every other line, per every one line of odd numbered rows or even numbered rows.

13. A non-transitory storage medium storing a program that causes a computer to execute radiographic video processing, the processing comprising:

detecting whether or not a video image formed from a plurality of frames is being captured using a radiation detector in which a plurality of pixels are disposed in a matrix formation, each pixel including a sensor portion that generates charges according to irradiated radiation and a switching element that reads charges generated at the sensor portion, by switching the switching elements ON and OFF to read the charges and converting the read charges to voltage, and detecting whether or not a number of the pixels, from which charges are combined and read by the switching elements included in adjacent pixels, has been increased; and controlling such that, if it is detected that the number of pixels has been increased, the gradation signals expressing the charges distributed in a higher density range than that for frames subsequent to a predetermined frame are used as image data, from a frame at a time of the increase up until the predetermined frame.

14. The non-transitory storage medium of claim 13, wherein if the number of pixels has been increased, the controlling includes performing dynamic range compression with respect to the gradation signals distributed in the higher density range than that for frames subsequent to the predetermined frame, from the frame at the time of the increase up until the predetermined frame.

15. The non-transitory storage medium of claim 13, wherein the controlling further effects control such that, for the frames subsequent to the predetermined frame, a range of the gradation signals used as image data is gradually shifted to a range lower than the higher density range.

16. The non-transitory storage medium of claim 13, wherein the predetermined frame is a frame at a time immediately before density fluctuations in the gradation signals, due to switching of the number of pixels, stabilize.

17. The non-transitory storage medium of claim 13, wherein the detecting whether or not the number of pixels has been increased includes detecting satisfaction of a condition of:

a transition from a state in which still image capture is performed by the radiation detector to a state in which video image capture is performed by the radiation detector; or a frame rate of the video image capture has been increased while performing video image capture by the radiation detector; or a transition from a sequential scanning method in which charges generated in the pixels are read sequentially to a skip scanning method in which charges generated in each of the pixels are read from every other line, per every one line of odd numbered rows or even numbered rows.

* * * * *